(12) United States Patent
Narimatsu et al.

(10) Patent No.: US 7,262,039 B1
(45) Date of Patent: Aug. 28, 2007

(54) POLYPEPTIDE

(75) Inventors: Hisashi Narimatsu, Higashiyamato (JP); Takashi Kudo, Hachioji (JP); Katsutoshi Sasaki, Sagamihara (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/744,748

(22) PCT Filed: Jul. 29, 1999

(86) PCT No.: PCT/JP99/04092

§ 371 (c)(1),
(2), (4) Date: Jan. 29, 2001

(87) PCT Pub. No.: WO00/06708

PCT Pub. Date: Feb. 10, 2000

(30) Foreign Application Priority Data

Jul. 29, 1998 (JP) ................................ 10/213823

(51) Int. Cl.
*C12N 9/10* (2006.01)
*C12P 21/06* (2006.01)
*C12P 19/18* (2006.01)
*C07H 21/04* (2006.01)
*C12N 9/00* (2006.01)

(52) U.S. Cl. .............................. 435/193; 435/4; 435/6; 435/69.1; 435/183; 435/252.3; 435/320.1; 435/325; 435/348; 435/254.1; 435/358; 435/410; 536/23.2; 536/23.5; 536/23.7

(58) Field of Classification Search ............... 435/69.1, 435/183, 193, 41, 70.1, 70.3, 72, 252.3, 252.8, 435/254.11, 320.1, 419, 358, 366, 4, 6, 252.37, 435/325; 800/8.7, 295; 536/23.2, 23.5, 536/23.4; 530/350
See application file for complete search history.

(56) References Cited

U.S. PATENT DOCUMENTS 5,384,249 A * 1/1995 Sasaki et al. ............... 435/68.1
5,625,124 A 4/1997 Falk et al. ..................... 800/2

FOREIGN PATENT DOCUMENTS

| WO | 93/16178 | 8/1993 |
| WO | WO94/02616 | 2/1994 |
| WO | 96/40881 | 12/1996 |
| WO | WO97/09421 | 3/1997 |

OTHER PUBLICATIONS

Ge et al. (J. Biol. Chem. vol. 272(34):21357-21363, Aug. 1997).*
Lowe et al. (J. Biol. Chem. vol. 266(26):17467-17477, Sep. 1991).*
Sasaki et al. Journal of Biological Chemistry., 268, 22782 (1993).*
Wang, et al., "Sequence Analysis of a *Staphylococcus aureus* Gene Encoding . . . ", Gene, vol. 102 (1991), pp. 105-109.
Mahairas, G.G., et al., "CIT Human Genomic Sperm Library C. *Homo sapiens* . . . " GenBank Accession, No. B41073 (1997).
Kageyama, et al., "Molecular Cloning and Characterization of Two . . . ", J. Biochem., vol. 125, (1999), pp. 838-845.
Kudo, et al., "Expression Cloning and Characterization of a Novel Murine . . . ", The Journal of Biological Chemistry, vol. 273, No. 41, (1998), pp. 26729-26738.
Kaneko, et al., "α1,3-Fucoslytransferase IX (Fuc-TIX) is very highly conserved", FEBS Letters, vol. 452 (1999), pp. 237-242.
Costache, et al., "Evolution of Fucoslytransferase Genes in Vertebrates", The Journal of Biological Chemistry, vol. 272, No. 47 (1997), pp. 29721-29728.
Cameron, et al., "Expression of Human Chromosome 19p α(1,3)-Fucoslytransferase . . . ", The Journal of Biological Chemistry, vol. 270, No. 34 (1995), pp. 20112-20122.
Weston, et al., "Isolation of a Novel Human α(1,3)Fucoslytransferase Gene . . . ", The Journal of Biological Chemistry, vol. 267, No. 6 (1992), pp. 4152-4160.

* cited by examiner

*Primary Examiner*—Manjunath Rao
(74) *Attorney, Agent, or Firm*—Fitzpatrick, Cella, Harper & Scinto

(57) ABSTRACT

This invention relates to a novel polypeptide having an α1,3-fucosyltransferase activity, a method for producing the polypeptide, a DNA encoding the polypeptide, a method for producing the DNA, a recombinant vector obtained by inserting the DNA thereinto, a transformant having the recombinant vector, an antibody recognizing the polypeptide, a method for determining or immunostaining the polypeptide of the present invention using the antibody, a method for producing a fucose-containing sugar chain using the polypeptide or the transformant, a method for screening a substance that changes the expression of a gene encoding the polypeptide, a method for screening a substance that changes the activity of the polypeptide, and a method for diagnosing diseases such as encephalopathy, renal diseases and cancers.

16 Claims, 16 Drawing Sheets

A

B

POLYPEPTIDE

TECHNICAL FIELD

The present invention relates to a novel polypeptide having α1,3-fucosyltransferase activity, a method for producing the polypeptide, a DNA encoding the polypeptide, a recombinant vector into which the DNA is integrated, a transformant having the recombinant vector, an antibody recognizing the polypeptide, a method for producing a fucose-containing sugar chain and a complex carbohydrate containing the sugar chain using the polypeptide, and a method for producing a fucose-containing sugar chain and a complex carbohydrate containing the sugar chain using a transformant having the recombinant vector.

BACKGROUND ART

It is thought that fucose-containing sugar chains are not only associated with such vital phenomena as development, differentiation and cell recognition, but are also associated with the onset and progression of inflammations, cancers, autoimmune diseases and many other diseases (Edited by Akira KOHATA, Senichiro HAKOMORI, Katsutaka NAGAI, *Glycobiology Series* 1–6, Kodansya, (1993), *Glycobiology*, 3, 97 (1993)).

Fucose-containing sugar chains are bound to proteins or lipids, and thus exist not only in the form of glycoproteins, proteoglycans and glycolipids, but also in the form of oligosaccharides.

The Lewis x sugar chain [Galβ1-4(Fucα1-3)GlcNAc], one of the fucose-containing sugar chains, appears regularly in each developmental stage of the early embryo, brain and kidney. For the reasons that the Lewis x sugar chains have affinity with one another and that they are associated with the cell compaction which occurs in the developmental stage of mouse early embryos, it is considered that the Lewis x sugar chain plays an important role in the development of early embryo, brain and kidney, acting as an adhesion molecule or a sugar chain signal.

For this reason, by cloning a gene of α1,3-fucosyltransferase involved in the synthesis of the Lewis x sugar chain appearing in the developmental stage of those organs, and analyzing its role, it is possible to clarify the relation between the gene and hereditary diseases.

The sialyl Lewis x sugar chain [NeuAcα2-3Galβ1 1-4(Fucα1-3)GlcNAc], the sialyl Lewis a sugar chain [NeuAcα2-3Galβ1-3(Fucα1-4)GlcNAc], the Lewis x sugar chain and the Lewis y sugar chain [Fucα1-2Galβ1-4(Fucα1-3)GlcNAc] are known as cancer-associated sugar chains.

The sialyl Lewis a sugar chain is detected mainly in cancers developing in the digestive system such as colon cancer and pancreatic cancer with high frequency. On the other hand, the sialyl Lewis x sugar chain, the Lewis x sugar chain and the Lewis y sugar chain are detected in lung cancer, ovarian cancer and renal cancer as well as the cancers developing in the digestive system.

Since it is clear that, even if the same sugar chain appears, glycosyltransferase involved in the synthesis of the sugar chain varies depending on the cell, it is considered possible to diagnose cancers more correctly, for example, by identifying α1,3-fucosyltransferase involved in the biosynthesis of the Lewis x sugar chains in each cancer cell and clarifying the correlation between the transferase and the specific cancer.

The Lewis x sugar chain is also involved in both the clearance in the blood and targeting to the organ of interest in respect of the glycoprotein containing the sugar chain. It is considered possible to control the clearance rate of any protein in the blood or to target to the liver by artificially adding the Lewis x sugar chain to any protein (*J. Biol. Chem.*, 270, 24024–24031 (1995)).

Furthermore, since the Lewis x sugar chain is known to have an activity to adhere reciprocally among the sugar chains (*Glycoconjugate J.*, 11, 238–248 (1994), *Glycobiology*, 8,139–146 (1998)), after adding the Lewis x sugar chain to any protein, it is also possible to make the protein target to a cancer organ which highly expresses the Lewis x sugar chain.

In the case where the sialyl Lewis x sugar chain is added to a protein, it is thought that the protein targets a cell expressing selectin (e.g. vascular endothelial cell in inflammatory site).

Hence, in order to make any protein target to the liver or cancer tissues effectively, it is desirable that the Lewis x sugar chain is effectively added to the protein, while the sialyl Lewis x sugar chain is not added thereto. It is an industrially important object to develop a method for effectively adding the Lewis x sugar chain to any recombinant glycoprotein, without adding the sialyl Lewis x sugar chain thereto, in a host cell suitable for producing the recombinant glycoprotein (e.g. Namalwa cell, Namalwa KJM-1 cell, CHO cell etc.)

It has been reported that, when an α1,3-fucosyltransferase (Fuc-TIV) is expressed in a specific CHO cell line, the Lewis x sugar chain is expressed without expression of sialyl Lewis x sugar chain (*J. Biol. Chem.*, 266, 17467–17477(1991), *J. Biol. Chem.*, 266, 21777–21783 (1991)). However, since Fuc-TIV originally has an activity to synthesize the sialyl Lewis x sugar chain, when Fuc-TIV is expressed in other cells (e.g. other types of CHO cell lines or Namalwa KJM-1 cell), the sialyl Lewis x sugar chain is expressed in addition to the Lewis x sugar chain (*Cell.*, 63, 1349–1356, *J. Biol. Chem.*, 269, 14730–14737(1994)).

Some reasons why the amount of the sialyl Lewis x sugar chain synthesized by Fuc-TIV is different depending on the cells into which Fuc-TIV is introduced may be that the amount and kind of sugar chain acting as a substrate in these cells is different, and that the expression level of the expressed Fuc-TIV or other glycosyltransferases (e.g. α2,3-siaryltransferase) is different among these cells.

It is thought that, for example, α2,3-siaryltransferase (ST3Gal III or ST3Gal IV) and Fuc-TIV compete for the same substrate (a sugar chain having an N-acetyllactosamine structure).

When the activity of α2,3-siaryltransferase is relatively stronger than that of Fuc-TIV, an α2,3-sialyl-N-acetyllactosamine sugar chain is generated with higher priority, and then fucose is added to the sugar chain by Fuc-TIV to synthesize the sialyl Lewis x sugar chain. In contrast, when the activity of Fuc-TIV is relatively stronger than that of α2,3-siaryltransferase, fucosyl-N-acetyllactosamine sugar chain (the Lewis x sugar chain) is synthesized with higher priority. Since α2,3-siaryltransferase has low activity to add sialic acid to the Lewis x sugar chain, it is difficult to synthesize sialyl Lewis x sugar chain with α2,3-siaryltransferase.

Thus, it is considered that, if a novel α1,3-fucosyltransferase, which has an activity to synthesize the Lewis x sugar chain but does not have an activity to synthesize the sialyl Lewis x sugar chain, can be obtained, it is possible to effectively synthesize the Lewis x sugar chain without synthesizing the sialyl Lewis x sugar chain by expressing the transferase in a host cell. Many cells including cells suitable for substance production have N-acetyllactosamine structure which is a precursor of the Lewis x sugar chain. Accordingly, the isolation of the above-stated novel enzyme will make it possible to effectively synthesize the Lewis x sugar chain by using various kinds of cells as host cells, without synthesizing the sialyl Lewis x sugar chain. However, such an enzyme is still unknown.

Since anti-CD15 antibody which recognizes the Lewis x sugar chain binds to human sperm after acrosome reaction and inhibits the interaction between the sperm and an egg, it is assumed that the Lewis x sugar chain is deeply involved in fertilization (*American Journal of Reproductive Immunology*, 37, 172–183 (1997)). So, for the diagnosis and treatment of infertility disease, it is useful to identify an a α1,3-fucosyltransferase involved in the biosynthesis of the Lewis x sugar chain existing in a human sperm and clarify the relation between the transferase and infertility desease. Also, there is a possibility of establishing a safe and reliable contraception method, using a protein to which the Lewis x sugar chain or the Lewis y sugar chain is added.

Therefore, for these purposes also, the development of a method for effectively adding the Lewis x sugar chain to any protein is very important.

It has been found that the binding between selectins (E-, P- and L-selectin), an adhesive molecules and their sugar chain ligand (the sialyl Lewis x sugar chain or its relative sugar chains) is involved in the accumulation of leukocytes into inflammatory sites or homing of lymphocytes to a lymph nodes.

The sialyl Lewis x sugar chain and its stereo isomer, the sialyl Lewis a sugar chain are known as cancer-associated antigens whose expression level increases with canceration, and the antibodies recognizing these sugar chains are used for the serodiagnosis of cancers.

Since these sugar chains bind to selecting, it is assumed that these sugar chains are also involved in the metastasis of cancers. Recently, it has been discovered that glycolipid containing the Lewis x sugar chains existing in mouse kidney strongly bind to E-selectin (Biochem. Biophys. Res. Commun., 218, 610–615 (1996)).

A sugar chain having a strong binding acitivity to selectins is useful for the treatment and prevention of inflammation and metastasis of cancers, acting as a selectin antagonist. α1,3-fucosyltransferases expressed in a mouse kidney are assumed to be useful in the effective synthesis of selectin antagonists, and identification and production of the above enzymes are considered to be significant. Nevertheless, the above enzymes have not been identified yet.

To date, genes for 5 types of α1,3-fucosyltransferases (Fuc-TIII, Fuc-TIV, Fuc-TV, Fuc-TVI and Fuc-TVII) have been cloned, and acceptor substrate specifity of each enzyme has been analyzed (Kukowska-Latallo et al., *Genes &Dev.* 4, 1288–1303 (1990), Goelz et al., *Cell* 63, 1349–1356(1990), Lowe et al., *J. Biol. Chem.* 266, 17467–17477(1991), Kumar et al., *J. Biol. Chem.* 266, 21777–21783(1991), Weston et al., *J. Biol. Chem.* 267, 4152–4160(1992), Weston et al., *J. Biol. Chem.* 267, 24575–24584(1992), Koszdin et al., *Biochem. Biophys. Res. Commun.* 187, 152–157(1992), Sasaki et al., *J. Biol. Chem.* 269, 14730–14737(1994), Natsuka et al., *J. Biol. Chem.* 269, 16789–16794(1994)).

Fuc-TIII has both α1,3-fucosyltransferase activity and α1,4-fucosyltransferase activity and is capable of synthesizing the sialyl Lewis x sugar chain, the Lewis x sugar chain, the Lewis y sugar chain, the sialyl Lewis a sugar chain, the Lewis a sugar chain [Galβ1-3 (Fucα1-4) GlcNAc] and the Lewis b sugar chain [Fuc α1-2Galβ1-3 (Fucα1-4) GlcNAc] (Fuc-TIII has a strong acitivity to synthesize the Lewis a sugar chain and Lewis b sugar chains).

Fuc-TIV is capable of synthesizing the sialyl Lewis x sugar chain, the Lewis x sugar chain and the Lewis y sugar chain (Fuc-TIV has a strong activity to synthesize the Lewis x sugar chain and the Lewis y sugar chain).

Fuc-TV is capable of synthesizing the sialyl Lewis x sugar chain, the Lewis x sugar chain and the Lewis y sugar chain.

Fuc-TVI is capable of synthesizing the sialyl Lewis x sugar chain, the Lewis x sugar chain and the Lewis y sugar chain.

Fuc-TVII is capable of synthesizing only the sialyl Lewis x sugar chain.

As described above, each of the cloned 5 types of α1,3-fucosyltransferases seems to have a somewhat-similar acceptor substrate specificity, but in the strict sense, each enzyme has a distinct acceptor substrate specificity. Furthermore, it is clear that the expression of each enzyme is specific for a cell or stage and that multiple enzymes may be expressed in one cell simultaneously. Even though the above enzymes can synthesize fucose-containing sugar chains having similar structure, it is thought that respective enzyme has a distinct function, because of the difference in cells or stages of their expression.

By an enzymological analysis using the extracts from cells or tissues as an enzyme source, it is possible, to a certain extent, to identify an α1,3-fucosyltransferase which expresses in a tissue or cell (Mollicone et al., *Carbohydrate Research*, 228, 265–276 (1992), Weston et al., *J. Biol. Chem.*, 267, 24575–24584 (1992)). However, with the enzymological analysis, it is impossible to identify respective α1,3-fucosyltransferases expressed in a cell or tissue expressing multiple α1,3-fucosyltransferase, and to clarify the enzymologic characteristic of each α1,3-fucosyltransferase.

In order to detect the expression of a specific α1,3-fucosyltransferase, it is necessary to use an immunological detection method using a specific antibody or a detection method based on the nucleotide sequence of genes (e.g. Northern hybridization or PCR).

DISCLOSURE OF THE INVENTION

The object of the present invention is to provide medical agents such as anti-inflammatory agents, anti-infective agents or antimetastatic agents; food such as dairy products, a method for improving proteins, and a method for diagnosing diseases such as encephalopathy, renal diseases and cancers, using a polypeptide having a novel α1,3-fucosyltransferase activity.

The present invention relates to the following inventions 1 to 50.

1. A polypeptide having an activity to transfer fucose to an N-acetylglucosamine residue in an N-acetyllactosamine (Galβ1-4GlcNAc) structure existing in a nonreducing terminus of a sugar chain via an α1,3-linkage, but not having an activity to transfer fucose to an N-acetylglucosamine residue in an α2,3-sialyl N-acetyllactosamine (NeuAcα2-3Galβ1-4GlcNAc) structure existing in a nonreducing terminus of a sugar chain via an α1,3-linkage.

2. A polypeptide selected from the following (a), (b) and (c):
   (a) a polypeptide comprising the amino acid sequence represented by SEQ ID NO: 1 or 2,
   (b) a polypeptide comprising amino acid sequence of residues 56 to 359 represented by SEQ ID NO: 1 or 2,
   (c) a polypeptide comprising an amino acid sequence wherein one or more amino acids are deleted, substituted, or added in the amino acid sequence of the polypeptide of (a) or (b), having an activity to transfer fucose to an N-acetylglucosamine residue in an N-acetyllactosamine (Galβ1-4GlcNAc) structure existing in a nonreducing terminus of a sugar chain via an α1,3-linkage, but not having an activity to transfer fucose to the α2,3-sialyl N-acetyllactosamine (NeuAcα2-3Galβ1-4GlcNAc) structure existing in a nonreducing terminus of a sugar chain via an α1,3-linkage.

The deletion, substitution or addition of the above amino acid(s) can be performed by site-directed mutagenisis which was known prior to the filing date of the present application, and "one or more amino acids" means amino acid(s) which can be deleted, substituted or added by site-directed mutagenisis.

A polypeptide comprising an amino acid sequence wherein one or more amino acids are deleted, substituted or added, and having a novel α1,3-fucosyltransferase activity can be prepared according to methods described in *Molecular Cloning, The Second Edition, Current Protocols in Molecular Biology Supplement 1–38, Nucleic Acids Research,* 10, 6487 (1982), *Proc. Natl. Acad. Sci., USA,* 79, 6409(1982), *Gene,* 34, 315 (1985), *Nucleic Acids Research,* 13, 4431 (1985), *Proc. Natl. Acad. Sci USA,* 82, 488 (1985), *Proc. Natl. Acad. Sci., USA,* 81, 5662 (1984), *Science,* 224, 1431 (1984), PCT WO85/00817(1985), *Nature,* 316, 601 (1985) etc.

3. The polypeptide according to the above 1 or 2, wherein the activity of transferring fucose to an N-acetylglucosamine residue in the Galβ1-4GlcNAc structure existing in a nonreducing terminus of a sugar chain via an α1,3-linkage is the Lewis x sugar chain [Galβ1-4(Fucα1-3)GlcNAc] and the Lewis y sugar chain [Fucα1-2Galβ1-4(Fucα1-3)GlcNAc] synthesizing activity, and the activity of transferring fucose to an N-acetylglucosamine residue in the NeuAcα2-3Galβ1-4GlcNAc structure existing in a nonreducing terminus of a sugar chain via an α1,3-linkage is the sialyl Lewis x sugar chain [NeuAcα2-3Galβ1-4(Fucα1-3)GlcNAc] synthesizing activity.

4. A DNA selected from the following (a), (b), (c), (d), (e), (f), (g) and (h):
   (a) a DNA encoding the polypeptide selected from the polypeptides according to the above 1, 2 and 3,
   (b) a DNA having nucleotides 280 to 1194 of a nucleotide sequence represented by SEQ ID NO: 3,
   (c) a DNA having nucleotides 115 to 1194 of a nucleotide sequence represented by SEQ ID NO: 3,
   (d) a DNA having nucleotides 1454 to 2368 of a nucleotide sequence represented by SEQ ID NO: 4,
   (e) a DNA having nucleotides 1289 to 2368 of a nucleotide sequence represented by SEQ ID NO: 4,
   (f) a DNA having nucleotides 460 to 1374 of a nucleotide sequence represented by SEQ ID NO: 5,
   (g) a DNA having nucleotides 295 to 1374 of a nucleotide sequence represented by SEQ ID NO: 5, and
   (h) a DNA hybridizing under stringent conditions with DNA selected from (a), (b), (c), (d), (e), (f) and (g); and the DNA encodes a polypeptide having an activity to transfer fucose to an N-acetylglucosamine residue in an N-acetyllactosamine (Galβ1-4GlcNAc) structure existing in a nonreducing terminus of a sugar chain via an α1,3-linkage, but not having an activity to transfer fucose to an α2,3-sialyl N-acetyllactosamine (NeuAcα2-3Galβ1-4GlcNAc) structure existing in a nonreducing terminus of a sugar chain via an α1,3-linkage.

The above stated "a DNA hybridizing under stringent conditions" means a DNA obtained by colony hybridization, plaque hybridization, Southern blot hybridization or the like, using as a probe, DNA selected from the above (a), (b), (c), (d), (e), (f) and (g). Specifically, it means a DNA identified by subjecting a filter to which DNAs derived from colonies or plaques are immobilized, hybridizing at 65° C. in the presence of 0.7–1.0 M of NaCl, followed by washing the filter at 65° C. with 0.1–2.0 standard concentration of SSC (saline-sodium citrate) solution (one standard concentration of SSC solution consists of 150 mM sodium chloride and 15 mM sodium citrate).

The hybridization can be carried out according to methods described in the following protocols: *Molecular Cloning, A Laboratory Manual*, Second Edition, Cold Spring Harbor Laboratory Press (1989) (hereinafter, referred to as "*Molecular Cloning 2nd Edit*."), *Current Protocols in Molecular Biology Supplement 1–38*, John Wiley & Sons (1987–1997) (hereinafter, referred to as "*Current Protocols in Molecular Biology, Supplement 1–38*"), *DNA Cloning 1: Core Techniques, A Practical Approach*, Second Edition, Oxford University Press (1995) etc.

Examples of the DNAs capable of hybridizing include a DNA having at least 60% homology with the nucleotide sequence of a DNA encoding the polypeptide having an amino acid sequence represented by SEQ ID NO: 1 or 2, preferably a DNA having more than 80% homology, and more preferably a DNA having more than 95% homology.

5. A recombinant DNA obtained by integrating the DNA according to the above 4 into a vector.

6. The recombinant DNA according to the above 5 wherein it is plasmid pAMo-mFT9 or plasmid pBS-hFT9 (S2).

7. A transformant having the recombinant DNA according to the above 5 or 6.

8. The transformant according to the above 7 wherein it is a transformant selected from microorganisms, animal cells, plant cells, insect cells, non-human transgenic animals, and transgenic plants.

9. The transformant according to the above 8 wherein the microorganism belongs to *Escherichia*.

10. The transformant according to the above 8 wherein the animal cell is selected from mouse myeloma cells, rat myeloma cells, mouse hybridoma cells, CHO cell, BHK cell, African green monkey kidney cells, Namalwa cell, Namalwa KJM-1 cell, human fetal kidney cells, and human leukemia cells.

11. The transformant according to the above 8 wherein the insect cell is selected from *Spodoptera frugiperda* ovarian cells, *Trichoplusia ni* ovarian cells, and silkworm ovarian cells.

12. A method for producing a polypeptide selected from the polypeptides according to the above 1, 2 and 3, which comprises culturing in a medium a transformant having a recombinant DNA obtained by inserting a DNA encoding the polypeptide into a vector; producing and accumulating the polypeptide in the medium; and collecting the polypeptide from the medium.

13. A method for producing a polypeptide selected from the polypeptides according to the above 1, 2 and 3, which comprises feeding a non-human transgenic animal having a recombinant DNA obtained by inserting a DNA encoding the polypeptide into a vector; producing and accumulating the polypeptide in the non-human transgenic animal; and collecting the polypeptide from the non-human transgenic animal.

14. The method for producing the polypeptide according to the above 13, wherein the production and accumulation of the polypeptide is carried out in the milk of the non-human transgenic animal.
15. A method for producing a polypeptide selected from the polypeptides according to the above 1, 2 and 3, which comprises growing a transgenic plant having a recombinant DNA obtained by inserting a DNA encoding the polypeptide into a vector; producing and accumulating the polypeptide in the transgenic plant; and collecting the polypeptide from the transgenic plant.
16. A method for producing a polypeptide selected from the polypeptides according to the above 1, 2 and 3, which comprises using a DNA encoding the polypeptide, and synthesizing the polypeptide by an in vitro transcription-translation system.
17. A method for producing a reaction product wherein Fuc is added to an N-acetylglucosamine residue in the N-acetyllactosamine structure of an acceptor substrate via an α1,3-linkage, using a polypeptide selected from the polypeptides according to the above 1, 2 and 3 as an enzyme source; which comprises placing the following (a), (b) and (c) in an aqueous medium:
    (a) the enzyme source,
    (b) an acceptor substrate selected from: (i) N-acetyllactosamine(Galβ1-4GlcNAc), (ii) oligosaccharides having the N-acetyllactosamine structure in a nonreducing terminus thereof, (iii) complex carbohydrates having the N-acetyllactosamine structure in a nonreducing terminus of sugar chains, (iv) derivatives wherein the N-acetyllactosamine structure is modified by sulfate group, and (v) their derivatives wherein the N-acetyllactosamine structure is modified by sugar, but a galactose residue in the N-acetyllactosamine structure is not modified by sialic acid via an α2,3-linkage, and
    (c) guanosine-5'-diphosphate fucose;
    producing and accumulating the reaction product, in the aqueous medium; and collecting the reaction product from the aqueous medium.
18. The method for producing the reaction product according to the above 17 wherein a derivative is selected from sugar chains having, in a nonreducing terminus thereof, any one of the following oligosaccharide structures: Fucα1-2Galβ1-4GlcNAc, Galα1-3Galβ1-4GlcNAc, Galα1-3(Fucα1-2)Galβ1-4GlcNAc, GalNAcα1-3(Fucα1-2)Galβ1-4GlcNAc, Galα1-4Galβ1-4GlcNAc, Galβ1-4GlcNAc(6SO$_3^-$); and complex carbohydrates containing the sugar chains.
19. A method for producing a reaction product wherein fucose is added to a glucose residue in a lactose structure of an acceptor substrate via an α1,3-linkage, using a polypeptide selected from the polypeptides according to the above 1, 2 and 3 as an enzyme source; which comprises placing the following (a), (b) and (c) in an aqueous medium:
    (a) the enzyme source,
    (b) an acceptor substrate selected from (i) lactose (Galβ1-4Glc), (ii) oligosaccharides having a lactose structure in a nonreducing terminus thereof, (iii) complex carbohydrates having a lactose structure in a nonreducing terminus of sugar chains, (iv) their derivatives wherein a lactose structure is modified by sulfate group, and (v) their derivatives wherein a lactose structure is modified by sugar(s), but a galactose residue in the lactose structure is not modified by sialic acid via an α2,3-linkage, and
    (c) guanosine-5'-diphosphate fucose;
    producing and accumulating the reaction product, in the aqueous medium; and collecting the reaction product from the aqueous medium.
20. The method for producing the reaction product according to the above 19 wherein a derivative is selected from sugar chains having, in a nonreducing terminus thereof, any one of the following oligosaccharide structures: Galα1-3Galβ1-4Glc, Galα1-3(Fucα1-2)Galβ1-4Glc, GalNAcα1-3(Fucα1-2)Galβ1-4Glc, Galα1-4Galβ1-4Glc, Galβ1-4Glc(6SO$_3^-$); and complex carbohydrates containing the sugar chains.
21. A method for producing a sugar chain having a structure wherein fucose is added to an N-acetylglucosamine residue or a glucose residue via an α1,3-linkage, or a complex carbohydrate containing the sugar chain; which comprises, culturing in a medium a transformant selected from the transformants derived from microorganisms, animal cells, plant cells, and insect cells according to the above 8;
    producing and accumulating the sugar chain or the complex carbohydrate in the medium; and
    collecting the sugar chain or the complex carbohydrate from the medium.
22. A method for producing a sugar chain having structure wherein fucose is added to an N-acetylglucosamine residue or a glucose residue via an α1,3-linkage, or a complex carbohydrate containing the sugar chain; which comprises, feeding a non-transgenic animal according to the above 8;
    producing and accumulating the sugar chain or the complex carbohydrate in the non-transgenic animal; and
    collecting the sugar chain or the complex carbohydrate from the non-transgenic animal.
23. A method for producing a sugar chain having a structure wherein fucose is added to an N-acetylglucosamine residue or a glucose residue via an α1,3-linkage, or a complex carbohydrate containing the sugar chain; which comprises, growing a transgenic plant according to the above 8;
    producing and accumulating the sugar chain or the complex carbohydrate in the transgenic plant; and
    collecting the sugar chain or the complex carbohydrate from the transgenic plant.
24. The production method according to any one of the above 17 to 23 wherein the complex carbohydrate is selected from glycoproteins, glycolipids, proteoglycans, glycopeptides, lipopolysaccharides, peptideglycans and glycosides wherein a sugar chain binds to compounds such as steroids.
25. The method for producing the sugar chain or the complex carbohydrate according to the above 22 wherein the generation and accumulation of the sugar chain or the complex carbohydrate is carried out in the milk of the non-human transgenic animal.
26. A method for determining the expression level of a gene encoding a polypeptide selected from the polypeptides according to the above 1, 2 and 3, by hybridization using DNA encoding the polypeptide.
27. An oligonucleotide selected from the following oligonucleotides:
    an oligonucleotide having an identicel sequence to 10 to 50 contiguous nucleotides in a nucleotide sequence of DNA selected from a DNA encoding the polypeptide selected from the polypeptides according to the above 1, 2 and 3; a DNA having the nucleotide sequence represented by SEQ ID NO: 3; a DNA having the nucleotide sequence represented by SEQ ID NO: 4; and a DNA having the nucleotide sequence represented by SEQ ID NO: 5; and, an oligonucleotide having a complementary sequence to the oligonucleotide and a derivative of each of the oligonucleotides.

28. The oligonucleotide according to the above 27, wherein the oligonucleotide derivative is selected from the following oligonucleotide derivatives: an oligonucleotide derivative obtained by converting a phosphodiester bond into a phosphorothioate bond in an oligonucleotide; an oligonucleotide derivative obtained by converting a phosphodiester bond into a N3'-P5' phosphoamidate bond in an oligonucleotide; an oligonucleotide derivative obtained by converting a ribose and phosphodiester bond into a peptide nucleic acid bond in an oligonucleotide; an oligonucleotide derivative obtained by substituting uracil with C-5 propynyl uracil in an oligonucleotide; an oligonucleotide derivative obtained by substituting uracil with C-5 thiazolyl uracil in an oligonucleotide; an oligonucleotide derivative obtained by substituting cytosine with C-5 propynylcytosine in an oligonucleotide; an oligonucleotide derivative obtained by substituting cytosine with phenoxazine-modified cytosine in an oligonucleotide; an oligonucleotide derivative obtained by substituting ribose with 2'-O-propylribose in a DNA; and an oligonucleotide derivative obtained by substituting ribose with 2'-methoxyethoxyribose in the oligonucleotide.

29. A method for determining the expression level of a gene encoding a polypeptide selected from the polypeptides according to the above 1, 2 and 3 by polymerase chain reaction, using the oligonucleotide according to the above 27 or 28.

30. A method for detecting encephalopathy, renal diseases and cancers, using the method according to the above 26 or 29.

31. A method for supressing the transcription of a DNA encoding a polypeptide selected from the polypeptides according to the above 1, 2 and 3, using a DNA selected from a DNA encoding the polypeptide, a DNA having the nucleotide sequence represented by SEQ ID NO: 3, a DNA having the nucleotide sequence represented by SEQ ID NO: 4, and a DNA having the nucleotide sequence represented by SEQ ID NO: 5.

32. A method for supressing the translation of an mRNA encoding a polypeptide selected from the polypeptides according to the above 1, 2 and 3, using a DNA selected from a DNA encoding the polypeptide, a DNA having the nucleotide sequence represented by SEQ ID NO: 3, a DNA having the nucleotide sequence represented by SEQ ID NO: 4, and a DNA having the nucleotide sequence represented by SEQ ID NO: 5.

33. A method for supressing the transcription of a DNA encoding the polypeptide according to the above 1, 2 or 3, using the oligonucleotide according to the above 27 or 28.

34. A method for supressing the translation of an mRNA encoding the polypeptide according to the above 1, 2 or 3, using the oligonucleotide according to the above 27 or 28.

35. A method for treating renal diseases or cancers using a method of any one of the above 31 to 34.

36. An antibody recognizing a polypeptide selected from the polypeptides of the above 1, 2 and 3.

37. An immunoassay which detects a polypeptide selected from the polypeptides of the above 1, 2, and 3 using the antibody of the above 36.

38. An immunohistological staining method which detects a polypeptide selected from the polypeptides according to the above 1, 2 and 3 using the antibody according to the above 36.

39. A reagent for immunohistological staining which contains the antibody of the above 36.

40. An agent for diagnosing encephalopathy, renal diseases and cancers, which contains the antibody of the above 36.

41. A method for screening a substance that changes the activity of a polypeptide selected from the polypeptides according to the above 1, 2 and 3, which comprises contacting the polypeptide with test samples.

42. A method for screening a substance that changes the expression of a gene encoding a polypeptide selected from the polypeptides according to the above 1, 2 and 3, which comprises contacting a cell expressing the polypeptide with test samples, and measuring the amount of the Lewis x or Lewis y sugar chain using an anti-Lewis x or anti-Lewis y antibody.

43. A method for screening a substance that changes the expression of a gene encoding a polypeptide selected from the polypeptides according to the above 1, 2 and 3, which comprises contacting a cell expressing the polypeptide with test samples, and measuring the amount of the polypeptide using the antibody of the above 36.

44. A promoter DNA for the transcription of a gene encoding a polypeptide selected from the polypeptides according to the above 1, 2 and 3.

45. A promoter DNA according to above 44 which functions in a cell selected from neurons, kidney cells, gastric epithelium cells, leukocyte cells, cerebral tumor cells, neuroblastoma cells, melanoma cells, renal cancer cells, stomach cancer cells, colon cancer cells, and pancreatic cancer cells.

46. A promoter DNA according to the above 44 or 45 which is derived from human or mouse.

47. A method for screening a substance that changes the efficiency of transcription by a promoter DNA selected from the promoter DNAs according to the above 44, 45, and 46, which comprises transforming an animal cell with a plasmid comprising the promoter DNA and a reporter gene ligated downstream of the promoter DNA; contacting transformant with a test sample; and measuring the amount of the translation product of the reporter gene.

48. The screening method according to the above 47 wherein a reporter gene is a gene selected from chloramphenicol acetyltransferase genes, β-galactosidase genes, luciferase genes and green fluorescent protein genes.

49. A non-human knockout animal wherein a DNA encoding the polypeptide selected from the polypeptides according to the above 1, 2 and 3 is deleted or mutated.

50. A non-human knockout animal according to the above 49 wherein the non-human knockout animal is a mouse.

The present invention will be described in more detail below.

(1) Obtaining a Novel DNA Encoding the Polypeptide Having α1,3-fucosyltransferase Activity, Hereinafter also called a Novel α1,3-fucosyltransferase Gene, and Production of the DNA and Oligonucleotide A cDNA library is constructed from cells expressing the Lewis x or Lewis y sugar chains by a conventional method.

The cDNA library may be constructed by methods as described in Molecular Cloning, Second Edition and Current Protocols in Molecular Biology Supplement 1–38, or by using commercially available kits such as SuperScript Plasmid System for cDNA Synthesis and Plasmid Cloning (manufactured by Gibco BRL) and ZAP-cDNA Synthesis Kit (manufactured by Stratagene).

For this purpose, any cells expressing the Lewis x or the Lewis y sugar chains may be used, including mouse or human tissues such as brain, kidney, stomach, bladder, or testis; mouse F9 cells; and a human neuroblastoma cell line.

To construct the cDNA library, any cloning vectors capable of autonomously replicating in *E. coli* K12 may be used, including a phage vector and plasmid vector. Specific examples include ZAP Express [manufactured by Stratagene, Strategies, 5, 58 (1992)], pBluescript II SK(+) [Nucleic Acids Research, 17, 9494 (1989)], λzap II (manufactured by Strategene), λgt10, λgt11 [DNA Cloning, A Practical Approach, 1, 49 (1985)], λTriplEx (CloneTech), λExCell (manufactured by Pharmacia), pT7T3 18U (manufactured by Pharmacia), pcD2 [Mol. Cell. Biol., 3, 280 (1983)], pUC 18 [Gene, 33, 103 (1985)], and pAMo [J. Biol. Chem., 268, 22782–22787 (1993); also called pAMoPRC3Sc (Japanese Patent Laid-Open Publication No. 05-336963)].

As a host microorganism, any microorganisms belonging to *E. coli* may be used. Specific examples include *Escherichia coli* XL1-Blue MRF' [manufactured by Stratagene, Strategies, 5, 81 (1992)], *Escherichia coli* C600 [Genetics, 39, 440 (1954)], *Escherichia coli* Y1088 [Science, 222, 778 (1983)], *Escherichia coli* Y1090 [Science, 222, 778 (1983)], *Escherichia coli* NM522 [J. Mol. Biol., 166, 1 (1983)], *Escherichia coli* K802 [J. Mol. Biol., 16, 118 (1966)], *Escherichia coli* JM105 [Gene, 38, 275 (1985)], *Escherichia coli* SOLR™ Strain (manufactured by Stratagene), and *E. coli* LE392 (Molecular Cloning, Second Edition).

For example, the cDNA library may be constructed as follows.

cDNAs are synthesized from mRNAs derived from mouse brain using a cDNA Synthesis System kit commercially available from Gibco BRL.

After addition of a Sfi I linker to each terminus of the cDNAs, the cDNAs are inserted into Sfi I sites of cloning vector pAMo to prepare plasmids.

The above plasmids are then used to transform *E. coli* LE392 to construct a cDNA library.

A clone containing the DNA of interest may be selected from the constructed cDNA library as follows.

Plasmids are prepared from the above cDNA library by a conventional method or by using a plasmid preparation kit such as /plasmid/maxi kit (manufacutred by Qiagen, product No. 41031).

Since pAMo is an expression vector for animal cells, a cDNA library constructed using this plasmid may be used in the subsequent manipulations without any modification.

If a cDNA library is constructed using any vectors other than expression vectors, there is a need to excise inserted cDNAs from the cDNA library and then insert them again into an expression vector capable of expressing in animal or insect cells.

For this purpose, any expression vectors capable of expressing the cDNA inserted therein may be used, including pcDNAI/Amp, pcDNAI, pCDM8 (commercially available from Funakoshi, respectively), pAGE107 [Japanese Patent Laid-Open Publication No. 3-22979; Cytotechnology, 3, 133 (1990)], pREP4 (manufactured by Invitrogen), pAGE103 [J. Biochem., 101, 1307 (1987)], pAMo, pAMoA [J. Biol. Chem., 268, 22782–22787 (1993); also called pAMoPRSA (Japanese Patent Laid-Open Publication No. 05-336963)], pAS3-3 (Japanese Patent Laid-Open Publication No. 2-227075), pVL1392 (manufactured by Invitrogen), pVL1393 (manufactured by Invitrogen), and pBlueBacIII (manufactured by Invitrogen).

The expression vector containing the inserted cDNA is introduced into animal or insect cells capable of being screened for the cDNA of interest, thereby obtaining transformed cells.

The expression vector may be introduced by any methods for introducing DNA into animal or insect cells, for example, electroporation method [Cytotechnology, 3, 133 (1990)], calcium phosphate method (Japanese Patent Laid-Open Publication No. 2-227075), lipofection method [Proc. Natl. Acad. Sci. USA, 84, 7413 (1987)] and methods as described in Baculovirus Expression Vectors, W.H. Freeman and Company, New York (1992); Molecular Biology, A Laboratory Manual, Current Protocols in Molecular Biology; Bio/Technology, 6, 47 (1988) and Virology, 52, 456 (1973).

The animal cells include human Namalwa cells, Namalwa KJM-1 cells (subline of Namalwa cell), monkey COS cells, chinese hamster CHO cells, and HBT5637 (Japanese Patent Laid-Open Publication No. 63-299), with Namalwa cells or Namalwa KJM-1 cells being preferred.

As an insect cell, Sf9 or Sf21 cell [ovarian cells of *Spodoptera frugiperda*; Baculovirus Expression Vectors (1992)], High 5 cell (ovarian cells of *Trichoplusia ni*; manufactured by Invitrogen) and the like may be used.

The resulting transformed cells are cultured by a conventional method.

Specifically, the culturing may be carried out according to the following procedure for culturing transformants.

When the transformant is an animal cell, the cell may be cultured in a conventional medium such as RPMI 1640 medium [The Journal of the American Medical Association, 199, 519 (1967)], Eagle's MEM medium [Science, 122, 501 (1952)], DMEM medium [Virology, 8, 396 (1959)], 199 medium [Proceeding of the Society for the Biological Medicine, 73, 1 (1950)] or these media supplemented with fetal calf serum etc.

The culturing may generally be carried out for 1 to 7 days under the following conditions: at pH 6 to 8, at 30° C. to 40° C., under 5% $CO_2$ etc.

An antibiotic such as kanamycin or penicillin may be added to the medium during the culturing, if necessary.

When an insect cell is used as a host cell for transformation, the resulting transformants may be cultured in a conventional medium such as TNM-FH medium (manufactured by Pharmingen), Sf-900 II SFM medium (manufactured by Gibco BRL), ExCell 400 (manufactured by JRH Biosciences), ExCell 405 (manufactured by JRH Biosciences), and Grace's Insect Medium [Grace, T. C. C., Nature, 195, 788 (1962)].

The culturing may be carried out preferably at pH 6 to 7, at 25° C. to 30° C., generally for 1 to 5 days.

An antibiotic such as gentamicin may be added to the medium during the culturing, if necessary.

The resulting cultured cells are fluorescently stained with antibodies against the Lewis x or Lewis y sugar chains so as to concentrate and isolate cells having an increased binding capacity toward the above antibodies using a Fluorescence Activated Cell Sorter (FACS).

As an antibody against the Lewis x or Lewis y sugar chains, any antibodies reacting with the Lewis x or Lewis y sugar chains may be used, including the anti-Lewis x sugar chain antibody 73-30 (manufactured by Seikagaku Corporation) or PM-81, or the anti-Lewis y sugar chain antibody AH-6 (manufactured by Otsuka Pharmaceutical Co., Ltd).

SSEA-1 antibody may also be used that recognizes the Lewis x sugar chains on poly-N-acetyllactosamine sugar chains.

From the cells thus concentrated and isolated, a plasmid containing the DNA of the present invention may be collected by a known method such as Hirt method [Mol. Cell. Biol., 8, 2837 (1988)], thereby obtaining a DNA fragment containing the DNA.

For example, a plasmid containing the DNA of the present invention may be pAMo-mFT9.

Nucleotide sequence of the obtained DNA is determined by: integrating into a vector the obtained DNA, after cleaving with a suitable restriction enzyme, or without any treatment, according to a conventional method; and then analyzing it according to a conventional sequencing method such as dideoxy method described by Sanger [Proc. Natl. Acad. Sci. USA, 74, 5463 (1977)] or using a sequencer such as a 373A DNA sequencer (manufactured by Perkin Elmer).

DNAs obtainable by the above procedure include a DNA encoding the peptide represented by SEQ ID NO: 1, more specifically a DNA having the nucleotide sequence represented by SEQ ID NO: 3.

In addition, selection of DNAs hybridizing under stringent conditions with the DNA obtained by the above procedure may provide DNAs of interest derived from other tissues or animals, such as human.

Such DNAs include a DNA encoding the peptide represented by SEQ ID NO: 2, more specifically a DNA having the nucleotide sequence represented by SEQ ID NO: 4 or 5.

For example, a plasmid containing the DNA represented by SEQ ID NO: 5 may be pBS-hFT9(S2).

The DNA of interest may also be prepared by chemical synthesis using a DNA synthesizer based on the nucleotide sequence of the sequenced DNA. Examples of the DNA synthesizer include a DNA synthesizer based on thiophosphite method (manufactured by Shimadzu Corporation) and a DNA synthesizer model 392 based on phosphoramidite method (manufactured by Perkin Elmer).

Alternatively, the DNA of interest may also be prepared by Polymerase Chain Reaction (PCR) using the below-mentioned oligonucleotides as sense and antisense primers and using as a template cDNAs prepared from cells expressing mRNAs complementary to the DNA of interest [Molecular Cloning, Second Edition; PCR Protocols Academic Press (1990)].

The DNA or DNA fragments obtained by the above procedure may be used to prepare oligonucleotides, such as antisense and sense oligonucleotides, containing a partial sequence of the DNA of the present invention according to a conventional method as described in Molecular Cloning, Second Edition or using a DNA synthesizer.

The above oligonucleotides comprise a sequence identical or complementary to 10–50 successive nucleotides in the nucleotide sequence of the above DNA. Specifically, the oligonucleotides comprise a sequence identical or complementary to 10–50 successive nucleotides in the nucleotide sequence represented by SEQ ID NO: 3, 4 or 5. For sense and antisense primers, it is preferable to use the oligonucleotides whose melting temperatures (Tm) and nucleotide numbers are not extremely different from each other.

Further, derivatives of these oligonucleotides may also be used as the oligonucleotides of the present invention.

The oligonucleotide derivatives include an oligonucleotide derivative obtained by converting a phosphodiester bond in the oligonucleotide into a phosphorothioate bond; an oligonucleotide derivative obtained by converting a phosphodiester bond in the oligonucleotide into a N3'-P5' phosphoramidate bond; an oligonucleotide derivative obtained by converting a ribose and a phosphodiester bond in the oligonucleotide into a peptide-nucleic-acid bond; an oligonucleotide derivative obtained by replacing uracil in the oligonucleotide with C-5 propynyl uracil; an oligonucleotide derivative obtained by replacing uracil in the oligonucleotide with C-5 thiazolyl uracil; an oligonucleotide derivative obtained by replacing cytosine in the oligonucleotide with C-5 propynylcytosine; an oligonucleotide derivative obtained by replacing cytosine in the oligonucleotide with phenoxazine-modified cytosine; an oligonucleotide derivative obtained by replacing ribose in the oligonucleotide with 2'-O-propylribose; or the oligonucleotide derivative obtained by replacing ribose in the oligonucleotide with 2'-methoxyethoxyribose [Cell Technology, 16, 1463 (1997)].

(2) Preparation of a Novel Polypeptide Having an α1,3-fucosyltransferase Activity The DNA of the present invention obtained by the above procedure may be expressed in a host cell to produce the polypeptide of the present invention using a method as described in Molecular Cloning, Second Edition or Current Protocols in Molecular Biology Supplement 1–38.

Namely, the DNA of the present invention may be inserted into an appropriate expression vector downstream of a promoter, thereby constructing a recombinant vector. The recombinant vector may be introduced into a host cell to obtain a transformant expressing the polypeptide of the present invention, which may then be cultured for production of the polypeptide of the present invention.

As a host cell, any cells capable of expressing the gene of interest may be used, including prokaryotic cells, yeast cells, animal cells, insect cells, and plant cells. An animal or plant individual may also be used.

As an expression vector, it is possible to use any vectors that can autonomously replicate in the above host cells or can be integrated into chromosomes thereof and that contain a promoter at a suitable site for transcription of the novel α1,3-fucosyltransferase gene.

When a prokaryotic cell (e.g., a bacterial cell) is used as a host cell, a preferable expression vector for the novel α1,3-fucosyltransferase gene may be autonomously replicative in prokaryotic organisms and may comprise a promoter, a ribosome-binding sequence, the novel α1,3-fucosyltransferase gene and a terminator. The vector may further comprise a gene regulating the promoter.

The preferable expression vectors include pBTrp2, pBTac1, pBTac2 (commercially available from Boehringer Mannheim, respectively), pSE280 (Invitrogen), pGEMEX-1 (manufactured by Promega), pQE-8 (manufactured by QIAGEN), pKYP10 (Japanese Patent Laid-Open Publication No. 58-110600), pKYP200 [Agric. Biol. Chem., 48, 669 (1984)], pLSA1 [Agric. Biol. Chem., 53, 277 (1989)], pGEL1 [Proc. Natl. Acad. Sci., USA, 82, 4306 (1985)], pBluescript II SK(−) (manufactured by Stratagene), pTrs30 (FERM BP-5407), pTrs32 (FERM BP-5408), pGHA2 (FERM BP-400), pGKA2 (FERM B-6798), pTerm2 (Japanese Patent Laid-Open Publication No. 3-22979, US4686191, US4939094, US5160735), pKK233-2 (manufactured by Pharmacia), pGEX (manufactured by Pharmacia), pET system (manufactured by Novagen), pSupex, pUB110, pTP5, pC194, pTrxFus (manufactured by Invitrogen), and pMAL-c2 (manufactured by New England Biolabs).

As a promoter, any promoters capable of expressing in host cells, such as *E. coli*, may be used, including promoters derived from *E. coli* or a phage such as trp promoter (Ptrp), lac promoter (Plac), $P_L$ promoter, $P_R$ promoter and $P_{SE}$ promoter, SPO1 promoter, SPO2 promoter, and penP promoter. An artificially designed, modified promoter may also be used, including a promoter obtained by binding two Ptrp promoters in series (Ptrp×2), tac promoter, lac T7 promoter, and let I promoter.

As a ribosome-binding sequence, it is preferable to use a plasmid having an appropriate interval (e.g., 6–18 nucleotides) between Shine-Dalgarno sequence and an initiation codon.

A terminator is not necessarily required for expression of the DNA of the present invention, but it is desirably located immediately downstream of a structural gene.

The host cells include microorganisms belonging to *Escherichia, Serratia, Bacillus, Brevibacterium, Corynebacterium, Microbacterium, Pseudomonas*, and the like: for example, *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No.49, *Escherichia coli* W3110, *Escherichia coli* NY49, *Serratia ficaria, Serratia fonticola, Serratia liquefaciens, Serratia marcescens, Bacillus subtilis, Bacillus amyloliquefaciens, Brevibacterium ammoniagenes, Brevibacterium immariophilum* ATCC14068, *Brevibacterium saccharolyticum* ATCC 14066, *Corynebacterium glutanicum* ATCC13032, *Corynebacterium glutamicum* ATCC14067, *Corynebacterium glutamicum* ATCC13869, *Corynebacterium acetoacidophilum* ATCC13870, *Microbacterium ammoniaphilum* ATCC15354, and *Pseudomonas* sp. D-0110.

The recombinant vector may be introduced by any methods for introducing DNAs into these host cells: for example, electroporation method [Nucleic Acids Res., 16, 6127 (1988)], calcium ion-based method [Proc. Natl. Acad. Sci. USA, 69, 2110 (1972)], protoplast method (Japanese Patent Laid-Open Publication No. 63-248394) and the methods described in Gene, 17, 107 (1982) and Molecular & General Genetics, 168, 111 (1979).

When a yeast cell is used as a host cell, expression vectors include YEp13 (ATCC37115), YEp24 (ATCC37051), YCp50 (ATCC37419), pHS19, and pHS15.

As a promoter, any promoters capable of expressing in yeast cells may be used, including PHO5 promoter, PGK promoter, GAP promoter, ADH promoter, gal 1 promoter, gal 10 promoter, heat shock protein promoter, MF α 1 promoter, and CUP 1 promoter.

The host cells include yeast strains belonging to *Saccharomyces, Schizosaccharomyces, Kluyveromyces, Trichosporon, Schwanniomyces*, and the like: for example, *Saccharomyces cerevisiae, Schizosaccharomyces pombe, Kluyveromyces lactis, Trichosporon pullulans*, and *Schwanniomyces alluvius*.

The recombinant vectors may be introduced by any methods for introducing DNAs into yeast cells: for example, electroporation method [Methods. Enzymol., 194, 182 (1990)], spheroplast method [Proc. Natl. Acad. Sci. USA, 84, 1929 (1978)], lithium acetate method [J. Bacteriol., 153, 163 (1983)] and the method described in Proc. Natl. Acad. Sci. USA, 75, 1929 (1978).

When an animal cell is used as a host cell, expression vectors include pcDNAI/Amp, pcDNAI, pCDM8, pAGE107, pREP4, pAGE103, pAMo, pAMoA, and pAS3-3.

As a promoter, any promoters capable of expressing in animal cells may be used, including a promoter for immediate early (IE) gene of human cytomegalovirus (human CMV), SV40 early promoter, long terminal repeat promoter of moloney murine leukemia virus, retroviral promoter, heat shock promoter, SRα promoter, and metallothionein promoter. An enhancer for IE gene of Human CMV may also be used together with such a promoter.

The host cells include mouse myeloma cells, rat myeloma cells, mouse hybridoma cells, chinese hamster CHO cells, BHK cells, African green monkey kidney cells, human Namalwa or Namalwa KJM-1 cells, human fetal kidney cells, human leukemia cells, and HBT5637 (Japanese Patent Laid-Open Publication No. 63-299).

Specific examples may be SP2/O and NSO for the mouse myeloma cells, YB2/O for the rat myeloma cells, HEK293 and 293 for human fetal kidney cells, BALL-1 for human leukemia cells, and COS-1 and COS-7 for African green monkey kidney cells.

The recombinant vectors may be introduced by any methods for introducing DNAs into animal cells: for example, electroporation method [Cytotechnology, 3, 133 (1990)], calcium phosphate method (Japanese Patent Laid-Open Publication No. 2-227075), lipofection method [Proc. Natl. Acad. Sci. USA, 84, 7413 (1987)] and the method described in Virology, 52, 456 (1973). The transformants may be obtained and cultured according to the method described in Japanese Patent Laid-Open Publication No. 2-227075 or 2-257891.

When an insect cell is used as a host cell, polypeptides may be expressed by methods as described in Baculovirus Expression Vectors, A Laboratory Manual, W.H. Freeman and Company, New York (1992); Molecular Biology, A Laboratory Manual; Current Protocols in Molecular Biology Supplement 1–38; and Bio/Technology, 6, 47 (1988).

Namely, the recombinant vector for gene transfer and a baculovirus may be co-introduced into insect cells to obtain recombinant viruses in the supernatant from the cultured insect cells. Thereafter, insect cells may be infected with the resulting recombinant viruses to express the polypeptides.

The vectors for gene transfer to be used in the above procedure include pVL1392, pVL1393 and pBlueBacIII (commercially available from Invitrogen, respectively).

As a baculovirus, for example, *Autographa californica* nuclear polyhedrosis virus may be used, which infects *Noctuidae* insects.

The insect cells include *Spodoptera frugiperda* ovarian cells, *Trichoplusia ni* ovarian cells, and cultured cells derived from silk worm ovary.

Specific examples may be Sf9 and Sf21 (Baculovirus Expression Vectors, A Laboratory Manual) for *Spodoptera frugiperda* ovarian cells, High 5 and BTI-TN-5B1-4 (manufactured by Invitrogen) for *Trichoplusia ni* ovarian cells, and *Bombyx mori* N4 for the cultured cells derived from silk worm ovary.

The recombinant vector for gene transfer and the baculovirus may be co-introduced into insect cells by phosphate calcium method (Japanese Patent Laid-Open Publication No. 2-227075) or lipofection method [Proc. Natl. Acad. Sci. USA, 84, 7413 (1987)] in order to prepare the recombinant viruses.

Alternatively, DNAs may be introduced into insect cells using the same methods as described for DNA introduction into animal cells: for example, electroporation method [Cytotechnology, 3, 133 (1990)], calcium phosphate method (Japanese Patent Laid-Open Publication No. 2-227075), and lipofection method [Proc. Natl. Acad. Sci. USA, 84, 7413 (1987)].

When a plant cell or a plant individual is used as a host, polypeptides may be produced according to a known method as described in Tissue Culture, 20 (1994); Tissue Culture, 21 (1995); and Trends in Biotechnology, 15, 45 (1997).

As a promoter for gene expression, any promoters capable of expressing in plant cells may be used: including cauliflower mosaic virus (CaMV) 35S promoter and rice actin 1 promoter. Further, efficiency of gene expression can be improved by inserting Intron 1 of maize alcohol dehydrogenase gene between the promoter and the gene to be expressed.

The host cells include plant cells such as potato, tobacco, maize, rice, Brassica, soy bean, tomato, wheat, barley, rye, alfalfa, and flax.

The recombinant vectors may be introduced by any methods for introducing DNAs into plant cells: for example, Agrobacterium-based method, electroporation method [Cytotechnology, 3, 133 (1990)], and particle gun method.

Plant cells and organs having the transgene may be cultured on a large scale using a jar fermenter. Also, plant cells having the transgene may be redifferentiated to create a plant individual (transgenic plant) having the transgene.

Alternatively, an animal individual may be used to produce the polypeptide of the present invention. For example, the polypeptide of the present invention can be produced in an animal having the transgene according to a known method as described in American Journal of Clinical Nutrition, 63, 639S (1996); American Journal of Clinical Nutrition, 63, 627S (1996); and Bio/Technology, 9, 830 (1991).

As a promoter, any promoters capable of expressing within an animal may be used: for example, mammary gland cell-specific promoters such as α-casein promoter, β-casein promoter, β-lactoglobulin promoter and whey acidic protein promoter are preferred.

The polypeptide of the present invention may be obtained by culturing a microorganism-, animal cell-, or plant cell-derived transformant having a recombinant vector into which a DNA encoding the polypeptide has been introduced in accordance with a conventional culture method to produce and accumulate the polypeptide, and then collecting the polypeptide from the culture.

When the transformant is an animal or plant individual, the polypeptide may be obtained by feeding or cultivating the individual according to a conventional method to produce and accumulate the polypeptide, and then collecting the polypeptide from the individual.

Namely, in the case of an animal individual, for example, a non-human transgenic animal having the DNA of the present invention may be fed to produce and accumulate therein a novel polypeptide having an α1,3-fucosyltransferase activity, which is encoded by the recombinant DNA. The polypeptide may then be collected from the animal, thereby obtaining the polypeptide having an α1,3-fucosyltransferase activity. The polypeptide may be produced and accumulated in the animal's milk, egg, and the like.

In the case of a plant individual, for example, a transgenic plant having the DNA of the present invention may be cultivated to produce and accumulate therein a novel polypeptide having an α1,3-fucosyltransferase activity, which is encoded by the recombinant DNA. The polypeptide may then be collected from the plant, thereby obtaining the polypeptide having α1,3-fucosyltransferase activity.

If the transformants for producing the polypeptide of the present invention are prokaryotes such as E. coli etc. or eukaryotes such as yeast etc., the medium for culture of these organisms may be natural or synthetic mediun insofar as the medium contains a carbon source, a nitrogen source, inorganic salts etc. which can be assimilated by the said organisms and in which the transformants can be efficiently cultured.

Any carbon source can be used insofar as it can be assimilated by the microorganisms, and the following can be used: carbohydrates such as glucose, fructose, sucrose, molasses containing them, starch or starch hydrolysates; organic acids such as acetic acid, propionic acid; alcohols such as ethanol, propanol, and the like.

As a nitrogen source, the following can be used: ammonium salts of various inorganic acids and organic acids, such as ammonia, ammonium chloride, ammonium sulfate, ammonium acetate, and ammonium phosphate; other nitrogen-containing compounds; and peptone, meat extracts, yeast extracts, corn steep liquor, casein hydrolysates, soy bean meal, soy bean meal hydrolysates, various fermented cells and hydrolysates thereof and the like.

The inorganic salts used include potassium dihydrogen phosphate, dipotassium hydrogen phosphate, magnesium phosphate, magnesium sulfate, sodium chloride, ferrous sulfate, manganese sulfate, copper sulfate, calcium carbonate, and the like.

The culturing is conducted under aerobic conditions using e.g. shake culture or aeration stirring culture or the like means. The culturing temperature is preferably 15 to 40° C., and the culturing period is usually 16 to 96 hours. During culturing, pH is maintained at 3.0 to 9.0. Adjustment of the medium pH is conducted using an inorganic or organic acid, an alkaline solution, urea, calcium carbonate, ammonia and the like.

If necessary, additionally, antibiotics such as ampicillin and tetracycline may be added to the medium during the culturing.

For culturing a microorganism transformed with an expression vector using an inductive promoter as a promoter, an inducer may be added to the medium, if necessary. For example, for culturing a microorganism transformed with an expression vector using lac promoter, isopropyl-β-D-thiogalactopyranoside (IPTG) or the like may be added to the medium; for culturing a microorganism transformed with an expression vector using trp promoter, indole acrylic acid (IAA) or the like may satisfactorily be added to the medium.

If the transformants for producing the polypeptide of the present invention are animal cells, the medium for culturing the cells is a generally used medium such as RPMI1640 medium [The Journal of the American Medical Association, 199, 519 (1967)], Eagle's MEM medium [Science, 122, 501 (1952)], DMEM medium [Virology, 8, 396 (1959)], 199 medium [Proceeding of the Society for the Biological Medicine, 73, 1 (1950)] or any one of these media further supplemented with fetal calf serum.

The culturing is conducted usually for 1 to 7 days at pH 6 to 8, at 30 to 40° C. in the presence of 5% $CO_2$.

If necessary, antibiotics such as kanamycin and penicillin may be added to the medium during the culturing.

The medium for culturing the transformant obtained from insect cells as host may be a generally used medium such as TNM-FH medium (manufactured by Pharmingen), Sf-900 II SFM medium (manufactured by Gibco BRL), ExCell 400 and ExCell 405 [both are products of JRH Biosciences], Grace's Insect Medium [Grace, T. C. C., Nature, 195, 788 (1962)] or the like.

The culturing is conducted preferably at pH 6 to 7, at a temperature of 25 to 30° C. for a period of usually 1 to 5 days.

If necessary, antibiotics such as gentamycin may be added to the medium during the culturing.

The gene may be expressed not only as a full-length polypeptide, but also as a partial polypeptide containing a region having an α1,3-fucosyltransferase activity. In general, a glycosyltransferase has the topology of a type II transmembrane protein and comprises a cytoplasmic region of several to several tens of N-terminal amino acids, a transmembrane region with hydrophobic amino acids, a stem region of several to several tens of amino acids, and a C-terminal region, which is most of the remaining part including a catalytic region. The stem region and the C-terminal region, which is most of the remaining part including a catalytic region are thought to be exposed to the lumen of the Golgi body. The boundary between the stem region and the catalytic region can be experimentally determined by preparing various polypeptides which lack N-terminal regions with varying lengths, and then examining which polypeptide loses its activity. Alternatively, the stem region and the catalytic region can be predicted from amino-acid sequence comparison with a similar glycosyltransferase having the informations concerning the stem and catalytic regions.

The novel α1,3-fucosyltransferase of the present invention had a similar structure to that of other glycosyltransferases. That is, the novel α1,3-fucosyltransferase was thought to comprise a cytoplasmic region of 10 N-terminal amino acids, a hydrophobic transmembrane region of 20 amino acids following the cytoplasmic region, a stem region of at least 25 amino acids, and a C-terminal region, which is most of the remaining part including a catalytic region. The stem region was expected to contain at least 25 amino acids based on the amino-acid sequence homology with other α1,3-fucosyltransferases as well as the findings concerning the stem and catalytic regions of other α1,3-fucosyltransferases [J. Biol. Chem., 269, 14730–14737 (1994); J. Biol. Chem., 270, 8712–8722 (1995); Glycobiology, 7, 921–927 (1997)]. Accordingly, a polypeptide containing amino acids 56 to 359 is thought to include the catalytic region.

The above full-length polypeptide or a partial polypeptide containing a region having an α1,3-fucosyltransferase activity (catalytic region) may be either expressed directly, or expressed as a secreted protein or a fusion protein according to a method as described in Molecular Cloning, Second Edition. A protein to be fused with the polypeptide includes β-galactosidase, protein A, IgG-binding region of protein A, chloramphenicol acetyltransferase, poly(Arg), poly(Glu), protein G, maltose-binding protein, glutathione-S-transferase, polyhistidine chain (His-tag), S peptide, DNA-binding protein domain, Tac antigen, thioredoxin, green fluorescent protein, and an epitope of an antibody of interest [Akio Yamakawa, Experimental Medicine, 13, 469–474 (1995)].

The method of producing the polypeptide of the present invention includes intracellular production by host cells, extracellular secretion by host cells or production on outer membranes by host cells, and the method can be selected depending on the host cells used or on alternation of the structure of the polypeptide to be produced.

If the polypeptide of the present invention is produced in host cells or on outer membranes of host cells, the polypeptide can be efficiently secreted to extracellular portion from the host cells by use of the method of Paulson et al. [J. Biol. Chem., 264, 17619 (1989)], the method of Lowe et al. [Proc. Nat. Acad. Sci., USA, 86, 8227 (1989), Genes Develop., 4, 1288 (1990)] or methods described in e.g. Japanese Patent Laid-Open Publication Nos. 5-336963 and 6-823021.

That is, the polypeptide of the present invention can be efficiently secreted by expressing it as a form in which a signal peptide was added upstream of a polypeptide portion containing the active site of the polypeptide of the present invention, which can be achieved using gene manipulation techniques.

Specifically, the polypeptide of the present invention may be secreted efficiently from the host cells by expressing a polypeptide consisting of amino acids 56 to 359, which is thought to include the catalytic region, with a signal peptide added upstream of the polypeptide. Further, a tag for purification and detection may be inserted between the signal peptide and the polypeptide including the catalytic region, or added to C-terminus of the polypeptide including the catalytic region. As a tag for purification and detection, β-galactosidase, protein A, IgG-binding region of protein A, chloramphenicol acetyltransferase, poly(Arg), poly(Glu), protein G, maltose-binding protein, glutathione-S-transferase, polyhistidine chain (His-tag), S peptide, DNA-binding protein domain, Tac antigen, thioredoxin, green fluorescent protein, an epitope of an antibody of interest [Akio Yamakawa, Experimental Medicine, 13, 469–474 (1995)], or the like can be used.

The amount of the polypeptide produced can be increased by a gene amplification system using a dihydrofolate reductase gene or the like according to a method described in Japanese Patent Laid-Open Publication No. 2-227075.

For isolation and purification of the polypeptide of the present invention from a culture of the transformant for producing the polypeptide of the present invention, conventional methods for the isolation and purification of enzymes can be used.

For example, if the polypeptide of the present invention is accumulated as soluble forms in cells of the transformant for producing the polypeptide of the present invention, the cells are recovered from the culture by centrifuging the culture, then washed and disrupted with ultrasonic disrupter, French Press, Manton-Gaulin homogenizer, Dynomill or the like, to obtain a cell-free extract.

A purified preparation can be obtained by centrifuging the cell free extract to obtain the supernatant and then by subjecting the supernatant to solvent extraction, salting-out or desalting with sulfate ammonium etc., precipitation with organic solvent, anion-exchange chromatography on resin such as diethylaminoethyl (DEAE)-Sepharose, DIAION HPA-75 (manufactured by Mitsubishi Chemical Industries Ltd.) or the like, anion-exchange chromatography on resin such as S-Sepharose FF (manufactured by Pharmacia) or the like, hydrophobic chromatography on resin such as butyl Sepharose, phenyl Sepharose or the like, gel filtration using molecular sieve, affinity chromatography, chromatofocusing, and electrophoresis such as isoelectric focusing.

If said polypeptide is expressed as an inclusion body in cells, the cells are similarly recovered, disrupted and centrifuged to give a precipitated fraction. From the fraction the polypeptide is then recovered in a usual manner, and the inclusion body of the polypeptide is solubilized with a polypeptide denaturating agent. The solubilized solution is then diluted with or dialyzed against a solution not containing the polypeptide denaturating agent or a solution containing the polypeptide denaturating agent at the low concentration enough not to denature the polypeptide whereby the solubilized polypeptide is renatured to have normal tertiary structure, and its purified preparation can be obtained by use of the same isolation and purification methods as described above.

If said polypeptide is extracellularly secreted, the culture is subjected to means such as centrifugation to give a soluble fraction. From the soluble fraction, a purified preparation of said polypeptide can be obtained in the same manner as for isolation and purification from the cell-free extract as described above.

The polypeptide may also be purified according to conventional methods for purifying glycosyltransferases (J. Evan Sadler et al., Methods in Enzymology, 83, 458).

Furthermore, the polypeptide of the present invention may be produced as a fusion protein with another protein so that it can be purified by affinity chromatography using a substance having affinity for the fused protein [Akio Yamakawa, Experimental Medicine, 13, 469–474 (1995)]. For example, the polypeptide of the present invention is produced as a fusion protein with protein A so that it can be purified by affinity chromatography using immunoglobulin G, according to the method of Lowe et al. [Proc. Natl. Acad. Sci., USA, 86, 8227 (1989), Genes Develop., 4, 1288 (1990)] or methods described in Japanese Patent Laid-Open Publication Nos. 5-336963 and 6-823021/94. Furthermore, the polypeptide of the present invention is produced as a fusion protein with a FLAG peptide so that it can be purified by affinity chromatography using anti-FLAG antibody [Proc. Natl. Acad. Sci., USA, 86, 8227 (1989), Genes Develop., 4, 1288 (1990)]. Furthermore, the polypeptide can also be purified by affinity chromatography using an antibody against said polypeptide itself.

In addition, the α1,3-fucosyltransferase of the present invention may be produced using an in vitro transcription and translation system in a known manner [J. Biomolecular NMR, 6, 129–134; Science, 242, 1162–1164; J. Biochem., 110, 166–168 (1991)].

Further, the polypeptide of the present invention may also be produced by chemical synthesis methods including Fmoc method (fluorenyl methyloxy carbonyl method), tBoc method (t-butyloxy carbonyl method), and so on. Also, it may be chemically synthesized using a peptide synthesizer commercially available from Advanced ChemTech, Perkin Elmer, Pharmacia Biotech, Protein Technology Instrument, Synthecell-Vega, PerSeptive, or Shimadzu Corporation.

The structural analysis of the purified polypeptide may be carried out by a conventional method used in the field of protein chemistry: for example, the method described in "Protein Structural Analysis for Gene Cloning" (Hisashi Hirano, Tokyo Kagaku Dojin, 1993).

The novel polypeptide of the present invention having an α1,3-fucosyltransferase activity may be tested for its activity in a known manner [Methods in Enzymology, 83, 458; Methods in Enzymology, 179, 397; J. Biol. Chem., 269, 14730–14737 (1994); Japanese Patent Laid-Open Publication No. 06-823021].

(3) Production of a Sugar Chain Having Fuc Added to a GlcNAc or Glucose Residue via an α1,3-Linkage, and a Complex Carbohydrate Containing the Sugar Chain A sugar chain having Fuc added to a GlcNAc or glucose residue via an α1,3-linkage, or a complex carbohydrate containing the sugar chain may be produced by culturing in a medium a transformant selected from the transformants derived from microorganisms, animal cells, plant cells, and insect cells obtained in (2) above to produce and accumulate the sugar chain or the complex carbohydrate in the culture, and then collecting the sugar chain or the complex carbohydrate from the culture.

The sugar chains having Fuc added to a GlcNAc residue via an α1,3-linkage includes a sugar chain having the Lewis x or the Lewis y structure.

The culturing may be carried out according to the procedure mentioned in (2) above.

As for the above transformants, by coexpressing the polypeptide of the present invention and any recombinant glycoproteins (e.g. pharmaceutical recombinant glycoprotein) simultaneously in a transformant capable of synthesizing sugar chains, a sugar chain having Fuc attached to a GlcNAc or glucose residue via an α1,3-linkage may be added to the recombinant glycoprotein.

Also, the animal or plant individual obtained in (2) above may be used to produce the sugar chain having Fuc added to a GlcNAc or glucose residue via an α1,3-linkage, or the complex carbohydrate containing the sugar chain, according to the procedure mentioned in (2).

In the case of an animal individual, for example, a non-human transgenic animal having the DNA of the present invention may be fed to produce and accumulate therein the sugar chain having Fuc added to a GlcNAc or glucose residue via an α1,3-linkage, or the complex carbohydrate containing the sugar chain. The sugar chain or the complex carbohydrate may then be collected from the animal, thereby obtaining the sugar chain having Fuc added to a GlcNAc or glucose residue via an α1,3-linkage, or the complex carbohydrate containing the sugar chain.

The sugar chain or the complex carbohydrate may be produce and accumulated in the animal's milk, egg, and the like.

In the case of an plant individual, for example, a transgenic plant having the DNA of the present invention may be cultivated to produce and accumulate therein the sugar chain having Fuc added to a GlcNAc or glucose residue via an α1,3-linkage, or the complex carbohydrate containing the sugar chain. The sugar chain or the complex carbohydrate may then be collected from the plant, thereby obtaining the sugar chain having Fuc added to a GlcNAc or glucose residue via an α1,3-linkage, or the complex carbohydrate containing the sugar chain.

The polypeptide of the present invention obtained by the procedure mentioned in (2) above may be used as an enzyme source to produce, in an aqueous medium, a reaction product having Fuc added to a GlcNAc residue in the N-acetyllactosamine structure via an α1,3-linkage, as follows.

Namely, a reaction product having Fuc added to a GlcNAc residue in the N-acetyllactosamine structure of an acceptor substrate via an α1,3-linkage may be obtained by producing and accumulating the reaction product in an aqueous medium through an enzyme reaction using the polypeptide of the present invention obtained by the procedure mentioned in (2) as an enzyme source; GDP-Fuc; and the following acceptor substrate: N-acetyllactosamine (Galβ1-4GlcNAc), an oligosaccharide having the N-acetyllactosamine structure at the nonreducing terminus, a complex carbohydrate having a sugar chain with the N-acetyllactosamine structure at the nonreducing terminus, their derivatives having the N-acetyllactosamine structure modified with sulfate groups, or their derivatives having the N-acetyllactosamine structure modified with sugars and having no sialic acid added to a galactose residue in the N-acetyllactosamine structure via an α2,3-linkage; and then collecting the reaction product from the aqueous medium.

When the ability to produce 1 μmol Lacto-N-fucopentaose III (Galβ1-4(Fucα1-3)GlcNAcβ1-3Galβ1-4Glc) from Lacto-N-neotetraose (Galβ1-4GlcNAcβ1-3Galβ1-4Glc) as a substrate at 37° C. for 1 minute is set to 1 unit (U), the enzyme source may be used at a concentration of 0.1 mU/L to 10,000 U/L, preferably 1 mU/L to 1,000 U/L.

The aqueous medium includes water; a buffer such as phosphate buffer, carbonate buffer, acetate buffer, borate buffer, citrate buffer or Tris buffer; an alcohol such as methanol or ethanol; an ester such as ethyl acetate; a ketone such as acetone; and an amide such as acetamide. As an aqueous medium, it is also possible to use the medium for culturing microorganisms used as the enzyme source, the medium for culturing transformant mentioned in (2), and milk obtainable from a non-human transgenic animal mentioned in (2).

A surfactant or an organic solvent may be added to the aqueous medium, if necessary.

Any surfactant capable of promoting Fuc-containing carbohydrate production may be used, including a nonionic surfactant such as polyoxyethylene octadecylamine (e.g., Nimean S-215, manufactured by NOF Corporation); a cationic surfactant such as cetyltrimethylammonium bromide or alkyldimethyl benzylammonium chloride (e.g., Cation F2-40E, manufactured by NOF Corporation); an anionic surfactant such as lauroyl sarcosinate; and a tertiary amine such as alkyl dimethylamine (e.g., Tertiary Amine FB, manufactured by NOF Corporation). These surfactants may be used alone or in combination. They may be used generally at a concentration of 0.1 to 50 g/l.

The organic solvent includes xylene, toluene, fatty alcohol, acetone and ethyl acetate, which may be used generally at a concentration of 0.1 to 50 ml/l.

UDP-Fuc to be used may be commercially available; or produced through microorganism's action etc., which may be purified before use.

UDP-Fuc may be used at a concentration of 0.1 to 500 mM.

The derivative having the N-acetyllactosamine structure modified with sulfate groups or the derivative having an N-acetyllactosamine structure modified with saccharide and having no sialic acid added to a galactose residue in the N-acetyllactosamine structure via an α2,3-linkage includes Fucα1-2Galβ1-4GlcNAc, Galα1-3Galβ1-4GlcNAc, Galα1-3(Fucα1-2)Galβ1-4GlcNAc, GalNAcα1-3(Fucα1-2)Galβ1-4GlcNAc, Galα1-4Galβ1-4GlcNAc, Galβ1-4GlcNAc($6SO_3^-$), a sugar chain having one of these oligosaccharide structures at its nonreducing terminus, and a complex carbohydrate containing the sugar chain.

The acceptor substrate may be used at a concentration of 0.01 to 500 mM.

The reaction may be carried out in the presence of an inorganic salt such as $MnCl_2$; β-mercaptoethanol; or polyethylene glycol, if necessary.

The reaction may be carried out in an aqueous medium at pH 5 to 10, preferably pH 6 to 8, at 20° C. to 50° C. for 1 to 96 hours.

The polypeptide of the present invention obtainable by the procedure mentioned in (2) above may also be used as an enzyme source to produce, in an aqueous medium, a reaction product having Fuc added to a glucose residue in the lactose structure via an α1,3-linkage as follows.

Namely, a reaction product having Fuc added to a glucose residue in the lactose structure of an acceptor substrate via an α1,3-linkage may be obtained by producing and accumulating the reaction product in an aqueous medium through an enzyme reaction using the polypeptide of the present invention obtained by the procedure mentioned in (2) as an enzyme source; GDP-Fuc; and the following acceptor substrate: lactose (Galβ1-4Glc), an oligosaccharide having the lactose structure at the nonreducing terminus, a complex carbohydrate having a sugar chain with the lactose structure at the nonreducing terminus, their derivatives having the lactose structure modified with sulfate groups, or their derivatives having the lactose structure modified with sugars and having no sialic acid added to a galactose residue in the lactose structure via an α2,3-linkage; and then collecting the reaction product from the aqueous medium.

The derivative having the lactose structure modified with sulfate groups or the derivative having the lactose structure modified with sugars and having no sialic acid added to a galactose residue in the lactose structure via an α2,3-linkage includes Galα1-3Galβ1-4Glc, Galα1-3(Fucα1-2)Galβ1-4Glc, GalNAcα1-3(Fucα1-2)Galβ1-4Glc, Galα1-4Galβ1-4Glc, Galβ1-4Glc($6SO_3^-$); a sugar chain having one of these oligosaccharide structures at the nonreducing terminus, and a complex carbohydrate containing the sugar chain.

The reaction may be carried out under the same conditions as described for the reaction which provides the product having Fuc added to a GlcNAc residue in an N-acetyllactosamine structure of the receptive substrate via an α1,3-linkage, with the exception of replacing the acceptor substrate to be used.

The sugar chains or the complex carbohydrates produced by the above procedure may be cleaved using a known enzymatic or chemical technique to obtain a partial sugar chain [The Japanese Biochemical Society ed., "Continued Biochemical Experiment Course," vol. 4, Complex Carbohydrate Study I, II, Tokyo Kagaku Dojin (1986); Naoyuki Taniguchi, Akimi Suzuki, Kiyoshi Furukawa, Kazuyuki Sugawara, ed., "Glycobiology Experimental Protocols," Shujunsha Co., Ltd. (1996)].

(4) Application of the DNA or Oligonucleotide of the Present Invention to Treatment, Diagnosis of Diseases, or the like.

The DNA of the present invention can be used for treatment of diseases (e.g., brain diseases, renal diseases, or cancers) using an antisense RNA/DNA technique [Bioscience & Industry, 50, 322 (1992); Chemistry, 46, 681 (1991); Biotechnology, 9, 358 (1992); Trends in Biotechnology, 10, 87 (1992); Trends in Biotechnology, 10, 152 (1992); Cell Technology, 16, 1463 (1997)] or a triple helix technique [Trends in Biotechnology, 10, 132 (1992)], or can be used for diagnosis of these diseases using Northern hybridization or PCR.

For example, the DNAn oligonucleotide or derivatives thereof according to the present invention mentioned in (1) above may be administered to inhibit production of the polypeptide of the present invention.

Namely, the DNAn oligonucleotide or derivatives thereof according to the present invention may be used to suppress the transcription of a DNA encoding the polypeptide of the present invention and the translation of an mRNA encoding the polypeptide of the present invention.

Also, the DNA of the present invention or the oligonucleotide prepared therefrom may be used to determine the expression level of DNA encoding the polypeptide of the present invention by Northern hybridization or PCR.

Further, the DNA of the present invention may be used as a probe to obtain a promoter region for the gene in a known manner [Department of Oncology, The Institute of Medical Science, The university of Tokyo ed., "New Experimental Protocols in Cell Technology," Shujunsha Co., Ltd. (1993)].

The promoter region includes all promoter regions involved in the transcription of a gene encoding the polypeptide of the present invention in mammalian cells. Examples include promoter regions involved in the transcription of a gene encoding the polypeptide of the present invention in a human nerve cell, kidney cell, gastric epithelial cell, leukocyte, brain tumor cell, neuroblastoma cell, melanoma cell, renal cancer cell, gastric cancer cell, colon cancer cell or pancreatic cancer cell. The promoter can be used for the screening method mentioned below.

(5) Production of Antibodies for Recognizing the Polypeptide of the Present Invention (i) Preparation of Polyclonal Antibodies The purified full-length or partial polypeptide obtained by the procedure mentioned in (2) above or a peptide having a partial amino acid sequence of the protein of the present invention may be used as an antigen to prepare a polyclonal antibody by administering an animal with the antigen.

Examples of the animals used include rabbits, goats, 3- to 20-week-old rats, mice, hamsters and the like.

Preferable dosage of antigen is 50 to 100 µg per animal.

When a peptide is used as the antigen, it is preferred to use the peptide as the antigen after binding it covalently to a carrier protein, such as keyhole limpet haemocyanin, bovine thyroglobulin or the like.

Administration of the antigen is carried out 3 to 10 times at one- to two-week intervals after the first administration. A blood sample is recovered from the fundus of the eye 3 to 7 days after each administration, and the serum is tested, for example, by enzyme immunoassay [Enzyme-linked Immunosorbent Assay (ELISA), published by Igaku Shoin (1976); Antibodies—A Laboratory Manual, Cold Spring Harbor Laboratory (1988)] as to whether it is reactive with the antigen used for immunization.

A polyclonal antibody can be prepared by obtaining the serum from a non-human mammal whose serums shows a sufficient antibody titer against the antigen used for immunization, isolating and purifying it from the serum.

With regard to the method for the isolation and purification of the polyclonal antibody, centrifugation, salting-out method with 40 to 50% saturated ammonium sulfate, caprylic acid precipitation method [Antibodies, A Laboratory manual, Cold Spring Harbor Laboratory, (1988)], or chromatographic methods using a DEAE-Sepharose column, an anion exchange column, a protein A or G column, a gel filtration column and the like may be employed alone or in combination.

(ii) Preparation of a Monoclonal Antibody (a) Preparation of Antibody-Producing Cells The non-human mammal whose serum showed adequate antibody titer against a partial fragment of the polypeptide of the present invention used in immunization are used as a source of antibody-producing cells.

On day 3 to 7 after the final administering with the antigen to the non-human mammal with the antibody titer, the spleen is excised from the non-human mammal.

The spleen is cut into pieces in MEM medium (manufactured by Nissui Pharmaceuticals, Co.) and the pieces are then loosened with tweezers, followed by centrifugation at 1,200 rpm for 5 minutes, to discard the resulting supernatant.

The spleen cells in the resulting precipitated fraction are treated with a Tris-ammonium chloride buffer (pH 7.65) for 1 to 2 minutes to remove erythrocytes, followed by washing 3 times with MEM medium to give spleen cells as antibody-producing cells.

(b) Preparation of Myeloma Cells

As myeloma cells, cell lines obtained from mice or rats are used. For example, 8-azaguanine-resistant mice (BALB/c)-derived myeloma cell line P3-X63Ag8-U1 (hereinafter abbreviated to P3-U1) [Curr. Topics. Microbiol. Immunol., 81, 1 (1978), Europ. J. Immunol., 6, 511 (1976)], SP2/0-Ag14 (SP-2) [Nature, 276, 269 (1978)], P3-X63-Ag8653 (653) [J. Immunol., 123, 1548 (1979)], P3-X63-Ag8(X63) [Nature, 256, 495 (1975)] etc. can be used. These cell lines are further subjected to subculture in 8-azaguanine medium [medium prepared by adding 8-azaguanine (15 µg/ml) to a medium (referred to hereinafter as normal medium) having glutamine (1.5 mM), 2-mercaptoethanol ($5 \times 10^{-5}$ M), gentamicin (10 µg/ml) and fetal calf serum (FCS)(a product of CSL Ltd.; 10%) added to RPMI-1640 medium], and 3 to 4 days before cell fusion, they are cultured in the normal medium and at least $2 \times 10^7$ cells are used for fusion.

(c) Preparation of Hybridoma

The antibody-producing cells obtained in item (a) above and myeloma cells obtained in item (b) above are washed well with MEM medium or PBS (1.83 g of disodium phosphate, 0.21 g of monopotassium phosphate, 7.65 g of common salt, 1 L of distilled water, pH 7.2) and mixed such that the ratio of the antibody-producing cells/myeloma cells ranges from 5/1 to 10/1, and these cells are centrifuged at 1,200 rpm. for 5 minutes and the supernatant is discharged.

The cell pellet obtained as the precipitated fraction is well loosened, and a mixture containing of 2 g of polyethylene glycol-1000 (PEG-1000), 2 ml of MEM and 0.7 ml of dimethyl sulfoxide (DMSO) is added to the cells in a volume of 0.2 to 1 ml/$10^8$ antibody-producing cells with starring at 37° C., and 1 to 2 ml of MEM medium is added thereto several times at 1- to 2-minute intervals.

After addition, MEM medium is added to adjust the total volume to 50 ml.

The solution thus prepared is centrifuged at 900 rpm. for 5 minutes, and the supernatant is discarded.

The cells obtained in the precipitated fraction are gently loosened and suspended by pipetting in 100 ml of HAT medium [the medium prepared by adding hypoxanthine ($10^{-4}$ M), thymidine ($1.5 \times 10^{-5}$ M) and aminopterin ($4 \times 10^{-7}$ M) to the normal medium].

The suspension is divided into 96-well culture plates (100 µl/well) and is cultured at 37° C. in a 5% $CO_2$ incubator for 7 to 14 days.

After culturing, an aliquot of the supernatant is sampled and a hybridoma reacting specifically to a partial fragment of the polypeptide of the present invention is selected by enzyme immunoassays described in e.g. "Antibodies" [Antibodies, A Laboratory Manual, Cold Spring Harbor Laboratory, Chapter 14 (1988)].

Specifically, enzyme immunoassays are conducted as follows:

An appropriate plate is coated with a partial fragment of the polypeptide of the present invention, which was used as an antigen for immunization, followed by reaction with a culture supernatant of the hybridoma or with the purified antibody obtained in (d) below as a first antibody and then with anti-rat or anti-mouse immunoglobulin antibody as a second antibody labeled with biotin, an enzyme, a chemiluminescent substance or a radioisotope. Then, reaction depending on the labeling substance is conducted, and a hybridoma reacting specifically with the polypeptide of the present invention is selected as a hybridoma producing a monoclonal antibody against the polypeptide of the present invention.

Using the hybridoma, cloning is repeated two times by limiting dilution [for first dilution, HT culture medium (aminopterin-free HAT medium) is used; for second dilution, the normal medium is used]. A hybridoma showing a stable and strong antibody titer is selected as the hybridoma producing an antibody against the polypeptide of the present invention.

(d) Preparation of a Monoclonal Antibody

The hybridoma cells producing a monoclonal antibody against the polypeptide of the present invention, obtained in item (c) above, are injected at a dose of 5–20×10$^6$ cells/animal into the abdomens of 8 to 10-week-old mice or nude mice treated with 0.5 ml Pristane [animals raised for 2 weeks after intraperitoneal administration of 2,6,10,14-tetramethylpentadecane (Pristane)]. The hybridoma forms ascites tumor in 10 to 21 days.

From the mouse with the ascites tumor, the ascites is collected and centrifuged at 3,000 rpm for 5 minutes, to remove the solid matters from the fluid.

From the resulting supernatant, the monoclonal antibody can be purified and obtained according to the same method in the polyclonal antibody. Further, from the supernatant of the hybridoma which produces the monoclonal antibody, the monoclonal antibody can be purified and obtained according to the same method.

The class and subclass of the antibody are determined using a mouse monoclonal antibody typing kit or a rat monoclonal antibody typing kit. The protein content is determined by the Lowry method or calculated from absorbance at 280 nm.

(6) Use of the Antibody of the Present Invention (a) The antibody of the present invention can be used to detect the polypeptide of the present invention. Specifically, it is used in detection methods such as ELISA/fluorescent antibody method using a microtiter plate, Western blotting method etc.

(b) The antibody of the present invention can be used for immunostaining of tissues of cells expressing the polypeptide of the present invention.

(c) The antibody of the present invention can be used for diagnosis or treatment of diseases such as inflammations, cancers etc.

(7) Application to Screening Method

Because the polypeptide of the present invention has a novel α1,3-fucosyltransferase activity, when using a compound that enhances or inhibits this activity, it is possible to increase or decrease the amount of the Lewis x sugar chain, the Lewis y sugar chain or their modified sugar chains synthesized in cells.

In addition, the expression of the polypeptide can be controlled by a compound that promotes or supresses the transcription process of a gene encoding the polypeptide or the translation process of the transcript into a protein, resulting in a regulation of the amount of the Lewis x sugar chain, the Lewis y sugar chain or modified sugar chains thereof synthesized in cells.

Such compounds may be useful for treatment of diseases including brain diseases, renal diseases or cancers; or for synthesis of the Lewis x sugar chain, the Lewis y sugar chain or modified sugar chains thereof.

These compounds may be obtained according to the following procedures (a) to (e).

(a) The polypeptide of the present invention having a novel α1,3-fucosyltransferase activity (as a purified form, or cellular extract or culture supernatant of transformants expressing the polypeptide) prepared as mentioned in (2) above is used as an enzyme to determine the α1,3-fucosyltransferase activity in the presence of a test sample in a known manner [Methods in Enzymology, 83, 458; Methods in Enzymology, 179, 397; J. Biol. Chem., 269, 14730–14737 (1994); Japanese Patent Laid-Open Publication No. 06-823021], thereby selecting and obtaining the compound that has an activity to enhance or inhibit the α1,3-fucosyltransferase activity.

(b) Cells or the transformants mentioned in (2) above expressing the polypeptide of the present invention are cultured in the presence of a test sample for 2 hours to 1 week according to the culturing procedure mentioned in (2) above. Thereafter, the Lewis x sugar chain, the Lewis y sugar chain, or modified sugar chains thereof on the cell surface are detected with antibodies against these sugar chains, thereby selecting and obtaining the compound that has an activity to increase or decrease the amount of these sugar chains.

Examples of the detection method with antibodies include ELISA using a microtiter plate, a fluorescent antibody method, a Western blot method and immunohistological staining.

(c) Cells expressing the polypeptide of the present invention are cultured in the presence of a test sample for 2 hours to 1 week according to the culturing procedure mentioned in (2) above. Thereafter, an amount of the polypeptide in the cells is determined using the antibodies of the present invention mentioned in (5) above, thereby selecting and obtaining the compound that has an activity to increase or decrease the amount of the polypeptide.

Examples of the determination methods with antibodies include ELISA using a microtiter plate, a fluorescent antibody method, a Western blot method and immunohistological staining.

(d) Cells expressing the polypeptide of the present invention are cultured in the presence of a test sample for 2 hours to 1 week according to the culturing procedure mentioned in (2) above. Thereafter, an amount of the gene transcript encoding the polypeptide in the cells is determined by Northern hybridization method or PCR mentioned in (4) above, thereby selecting and obtaining the compound that has an activity to increase or decrease the amount of the transcript.

(e) A plasmid carrying a DNA insert containing a reporter gene linked downstream of the promoter obtained in (4) above is constructed in a known manner, and then transformed into the animal cells mentioned in (2) according to the procedure of (2), thereby obtaining transformants. The transformants are cultured in the presence of a test sample for 2 hours to 1 week according to the culturing procedures mentioned in (2) above. Thereafter, the expression level of the reporter gene in the cells is determined in a known manner [Department of Oncology, The Institute of Medical Science, The university of Tokyo ed., "New Experimental Protocols in Cell Technology," Shujunsha Co., Ltd. (1993); Biotechniques, 20, 914 (1996); J. Antibiotics, 49, 453 (1996); Trends in Biochemical Sciences, 20, 448 (1995); Cell Technology, 16, 581 (1997)], thereby selecting and obtaining the compound that has an ability to increase or decrease the expression level of the reporter gene expressed.

The reporter genes include chloramphenicol acetyltransferase gene, β-galactosidase gene, luciferase gene, and green fluorescent protein (GFP) gene.

(8) Creation of a Knockout Animal

A vector carrying the DNA of the present invention may be used for creation of a mutated clone, in which DNA encoding the polypeptide of the present invention on its chromosome is inactivated or replaced with any other sequence according to a known homologous recombination procedure [e.g., Nature, 326, 6110, 295 (1987); Cell, 51, 3, 503 (1987)], from an embryonic stem cell of a target animal, including cow, sheep, goat, pig, horse, chicken, or mouse. See, for example, Nature, 350, 6315, 243 (1991).

The embryonic stem cell clone thus created may be used for creation of a chimeric animal composed of the embryonic stem cell clones and normal cells by transferring the clone into the blastcyst of an animal's fertilized egg according to injection chimaera method or aggregation chimaera method. This chimeric animal may be mated with a normal animal to obtain an animal having any mutation in DNA encoding the polypeptide of the present invention on its chromosome in all cells of the entire body. Further, such animals may be mated with each other to obtain a homogeneous animal (knockout animal) having the mutation on both homologous chromosomes.

In this manner, a mutation may be introduced into any location in DNA encoding the polypeptide of the present invention on the chromosome in an animal individual. For example, a mutation such as base substitution, deletion or insertion may be introduced into the translated region of DNA encoding the polypeptide of the present invention on the chromosome, thereby resulting in a gene product having an altered activity. Introduction of a similar mutation into the expression control region can vary the level, stage and tissue specificity of the expression of the gene to be expressed. In addition, the combination with Cre-loxP system can more actively control the stage, site and level of the expression of the gene.

For example, the following cases are known: the deletion of a target gene in only a specific region of the brain using a promoter expressed in this region [Cell, 87, 7, 1317 (1996)], and the organ N-specific deletion of a target gene at a target stage using an adenovirus expressing Cre [Science, 278, 5335, (1997)].

Accordingly, an animal individual that allows the controlled expression of the DNA at any stage or in any tissue; or that has any insertion, deletion, or substitution in the translated region or the expression control region may be created for the DNA encoding the polypeptide of the present invention on the chromosome.

In such an animal, symptoms of various diseases caused by the polypeptide of the present invention may be induced at any stage, at any level, or at any site.

The knockout animal of the present invention is therefore a very useful animal model for treatment and prevention of various diseases caused by the polypeptide of the present invention. Particularly, it is very useful as an evaluation model for therapeutic or prophylactic agents against these diseases as well as functional foods or supplement foods.

This specification includes part or all of the contents as disclosed in the specification and/or drawings of Japanese Patent Application No. 10-213823 which is a priority document of the present application.

As control samples, the results regarding mouse Fuc-TIX transcript and mouse β-actin transcript are also shown.

A. is the figure showing the pattern of electrophoresis obtained by subjecting the RT-PCR samples to agarose gel electrophoresis (a. is concerned with the amount of Fuc-TIX transcripts and b. is concerned with that of Fuc-TIV.)

The bottom band in each gel represents one derived from internal control, whereas the upper band represents one derived from Fuc-TIX transcripts or Fuc-TIV transcript. B. is the figure showing the amounts of mouse Fuc-TIX transcripts, mouse Fuc-TIV transcripts or mouse β-actin transcripts, which were determined using calibration curves made by standard plasmids. The amount represents that in 1 μl of single stranded cDNA solution prepared according to the method described herein.

Standard DNA in A. represents the amount of the standard plasmids used for making the calibration curves. (1) is 40 fg, (2) is 20 fg, (3) is 10 fg, (4) is 5 fg, (5) is 2.5 fg and (6) is 1.25 fg.

Figure 6:
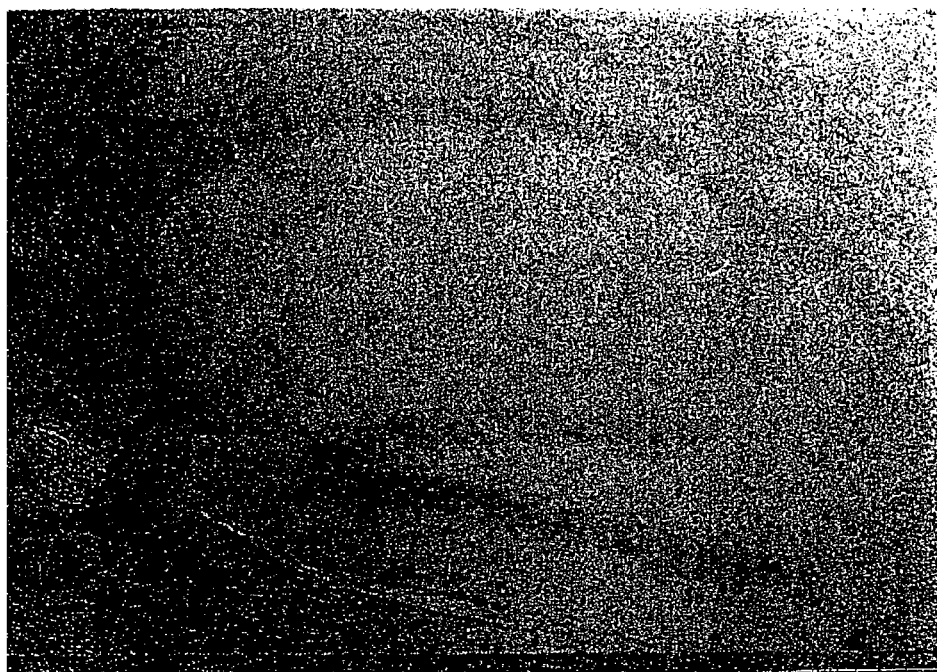
Figure 6:
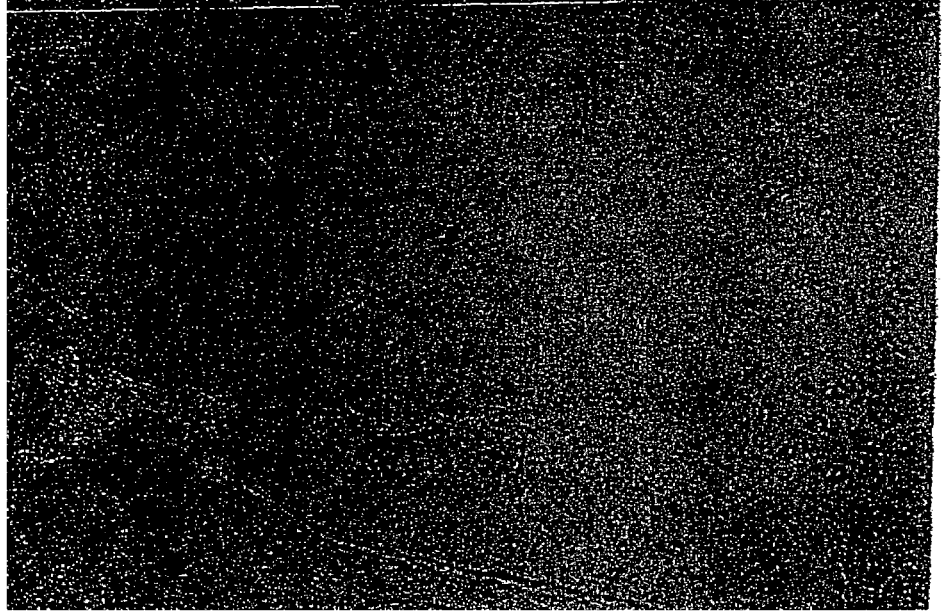

FIG. 6 shows photographs of in situ hybridization with slices of mouse brain tissues in order to determine the distribution of mouse Fuc-TIX transcripts. These results were obtained using a probe which was prepared with the primers represented by SEQ ID NO: 20 or 21. Using the antisense probe, Fuc-TIX transcripts was detected in perikaryon (A). On the other hand, using the sense probe as a negative control, no signal was exhibited (B).

Figure 7:
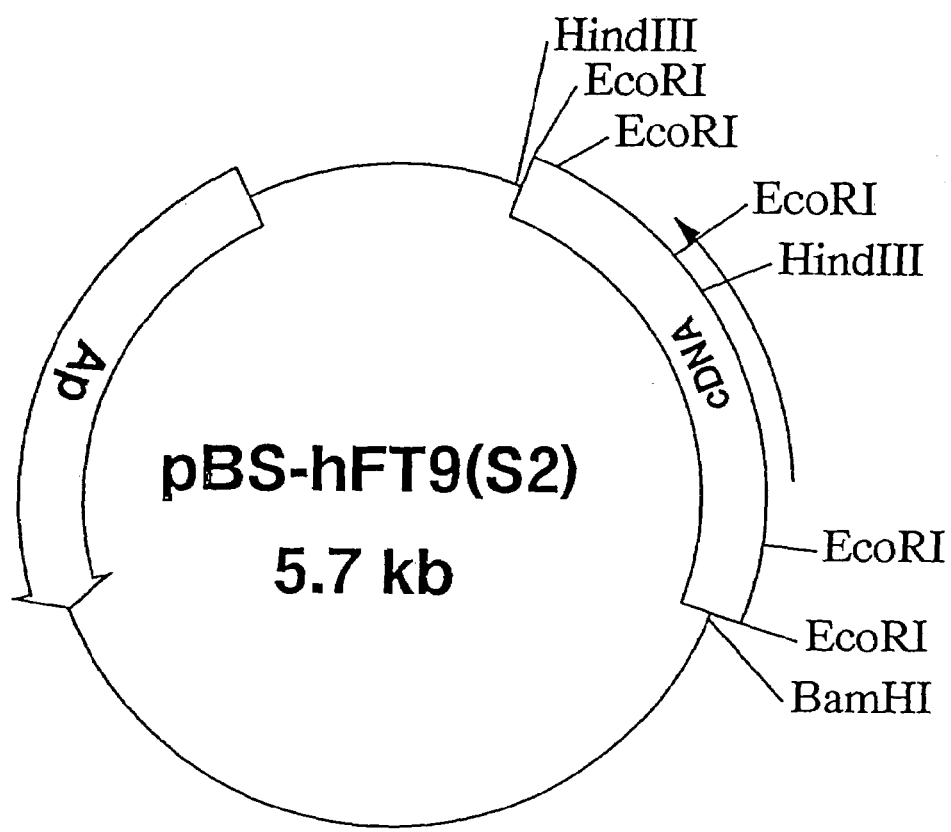

FIG. 7 shows the structure of a plasmid pBS-hFT9 (S2).

Both cDNA and Ap in the figure show a human Fuc-TIX cDNA and an ampicillin-resistance gene, respectively.

Figure 8:
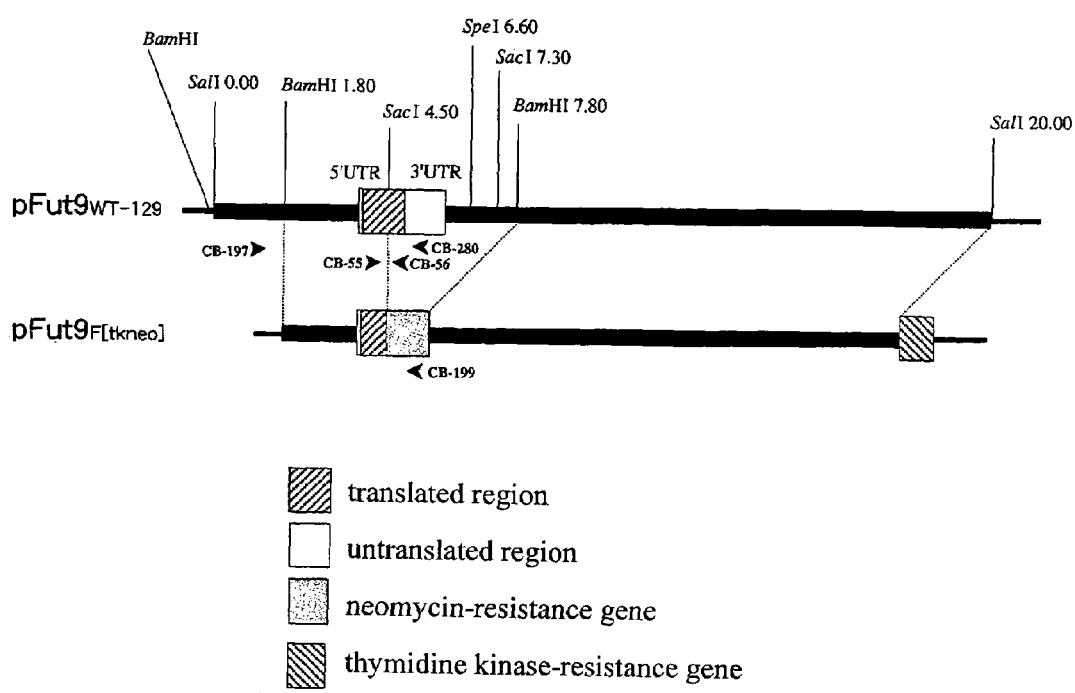

FIG. 8 shows the structure of a targeting vector pFut9F [tkneo]. For comparison, the structure of pFut9WT-129 is also shown, which is a plasmid obtained by subcloning the Fuc-TIX gene. Each description of various squares is as shown in the figure. Thick black lines represent both a portion of intron 2 of the Fuc-TIX gene and a chromosomal gene located downstream of the Fuc-TIX gene. Thin black lines represent pBluescript SK-portion. Furthermore, in this figure, 5'UTR represents 5' untranslated region and 3'UTR represents 3' untranslated region. Sites corresponding to primers used for PCR are also as shown in the figure.

Figure 9:
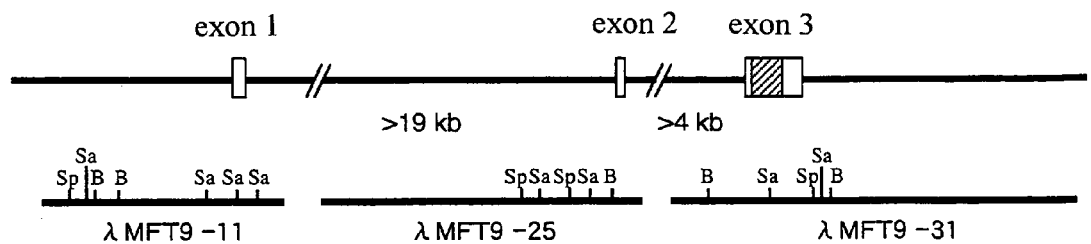

FIG. 9 shows the structure of mouse Fuc-TIX gene. The location of the mouse Fuc-TIX gene fragments contained in phage clones λMFT9-11, λMFT9-25 and λMFT9-31 is also shown herein. In the figure, B represents BamHI site, Sp represents SpeI site, and Sa represents SacI site.

Figure 10:
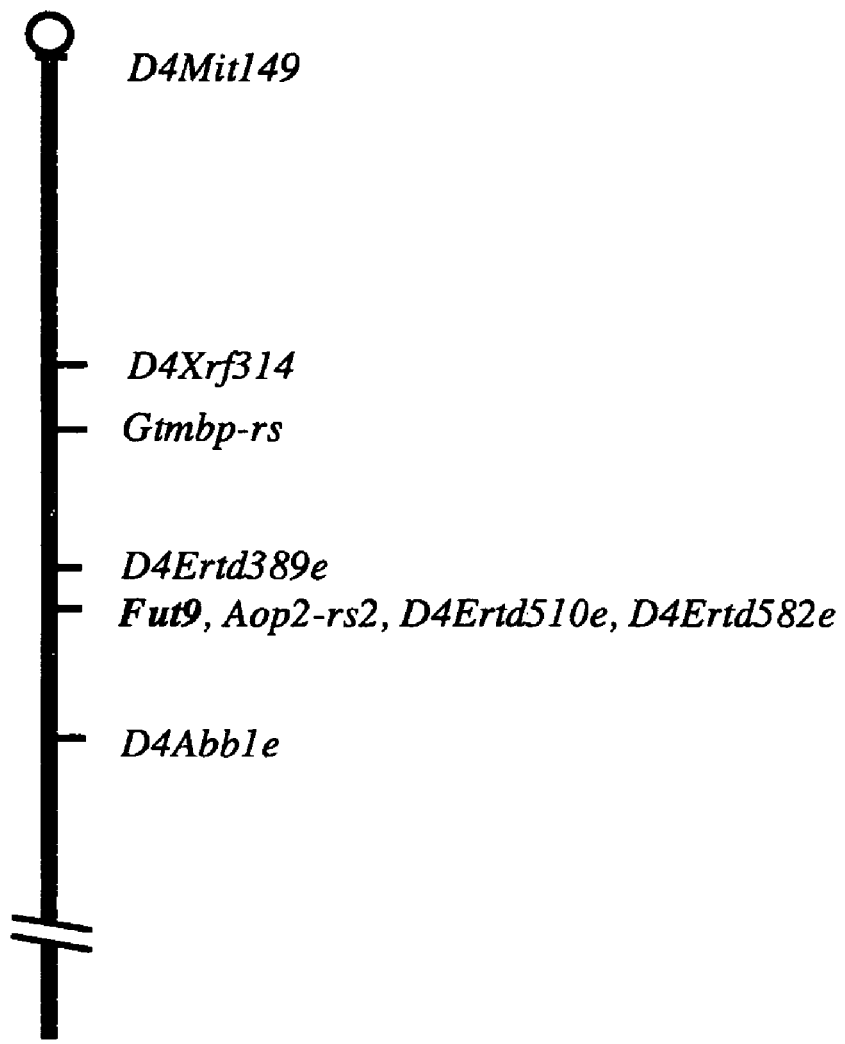

FIG. 10 shows the position of the mouse Fuc-TIX gene (which is shown as Fut9) on the mouse fourth chromosome. Other marker genes are also shown together with the mouse Fuc-TIX gene. In this figure, only a portion of the mouse fourth chromosome is shown.

Figure 11:
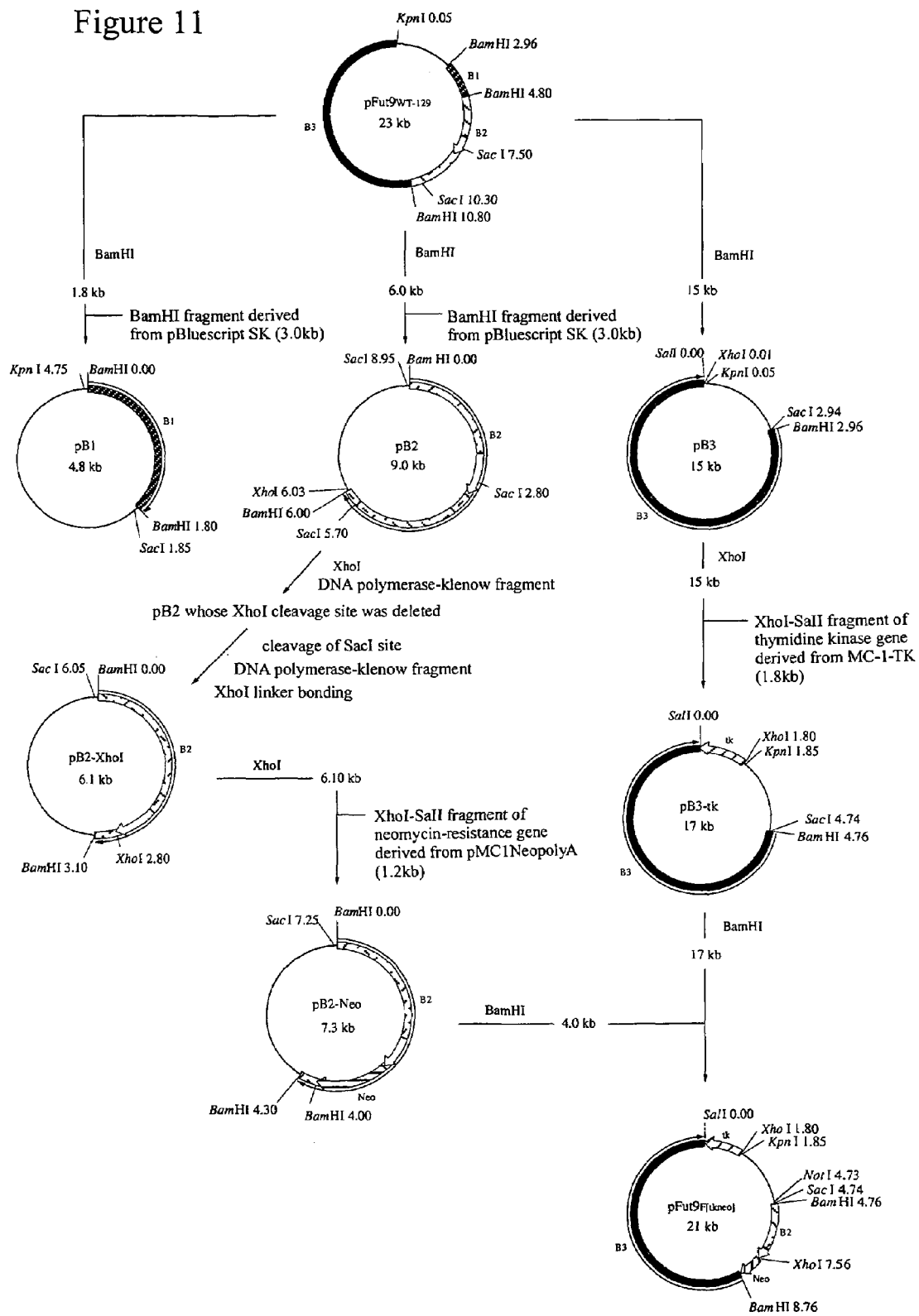

FIG. 11 shows a process of creating a targeting vector pFut9F[tkneo].

Figure 12:
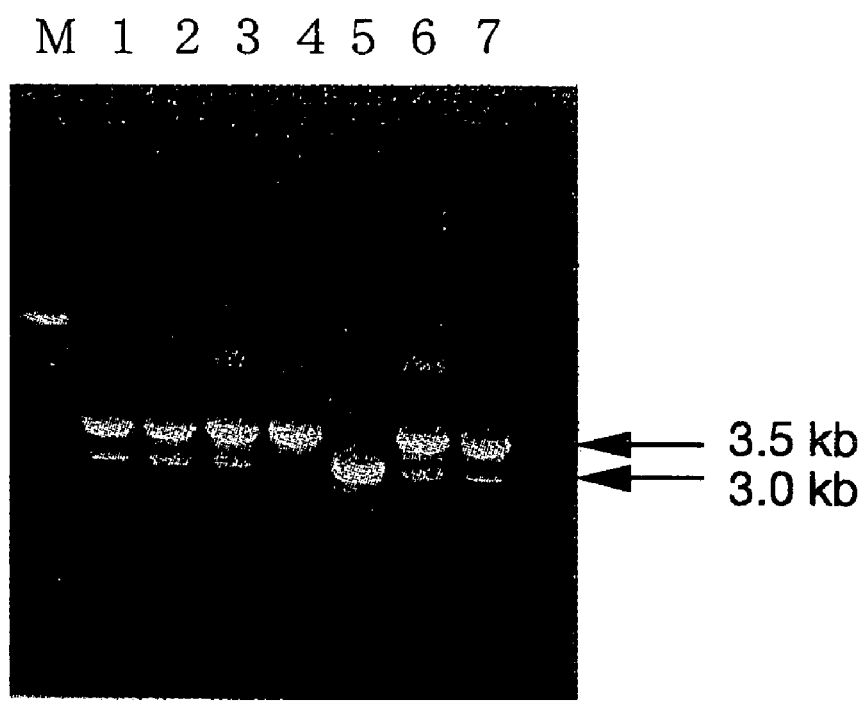

FIG. 12 shows the result of an electrophoresis to analyze the genotype of mice obtained by crossing two hetero mice. M represents molecular weight marker, and the numbers 1 to 7 represent the results of genotype analysis of each mouse.

Figure 13:
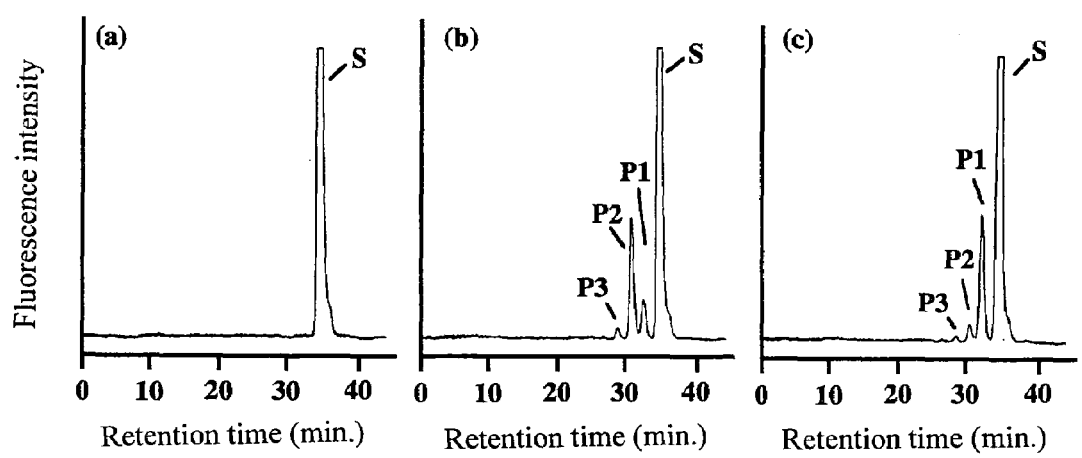

FIG. 13 shows the result of the reaction specificity of Fuc-TIX analyzed by HPLC. The shown result was obtained by adding the extract from Fuc-TIV expression cells (b) or Fuc-TIX expression cells (c) as an enzyme source to Galβ1-4GlcNAcβ1-3Galβ1-4GlcNAcβ1-3Galβ1-4GlcNAc-2AB (which is shown as S in the figure) and reacting the mixture, followed by detecting the obtained product by HPLC. (a) is the result of the reaction between S and the extract from a cell into which a control vector was introduced.

Figure 14:
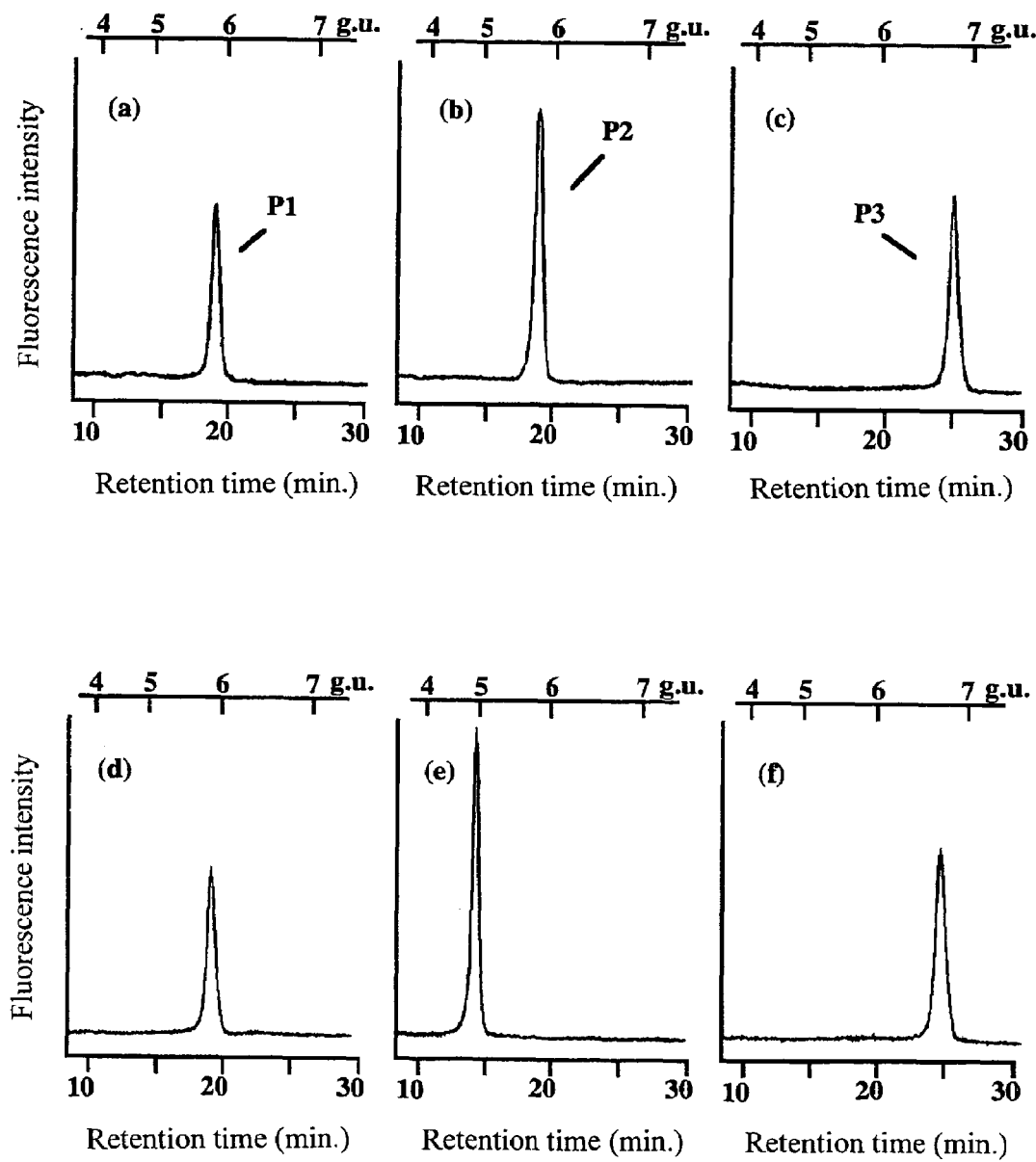

FIG. 14 shows the result obtained by reacting Fuc-TIX and a substrate Galβ1-4GlcNAcβ1-3Galβ1-4GlcNAcβ1-3Galβ1-4GlcNAc-2AB, followed by analyzing the obtained products (P1, P2 and P3) by HPLC. The elution positions of glucose homopolymer fluorescence-labeled with 2-aminobenzamide, which was used as a molecular weight marker, are shown at the top of the figure. The glucose unit of the glucose homopolymer is abbreviated as g.u. Each of (a) P1, (b) P2 and (c) P3 was treated with Jack bean β-galactosidase, and then each of the obtained products was analyzed by HPLC (The results were shown as (d), (e) and (f) respectively.)

Figure 15:
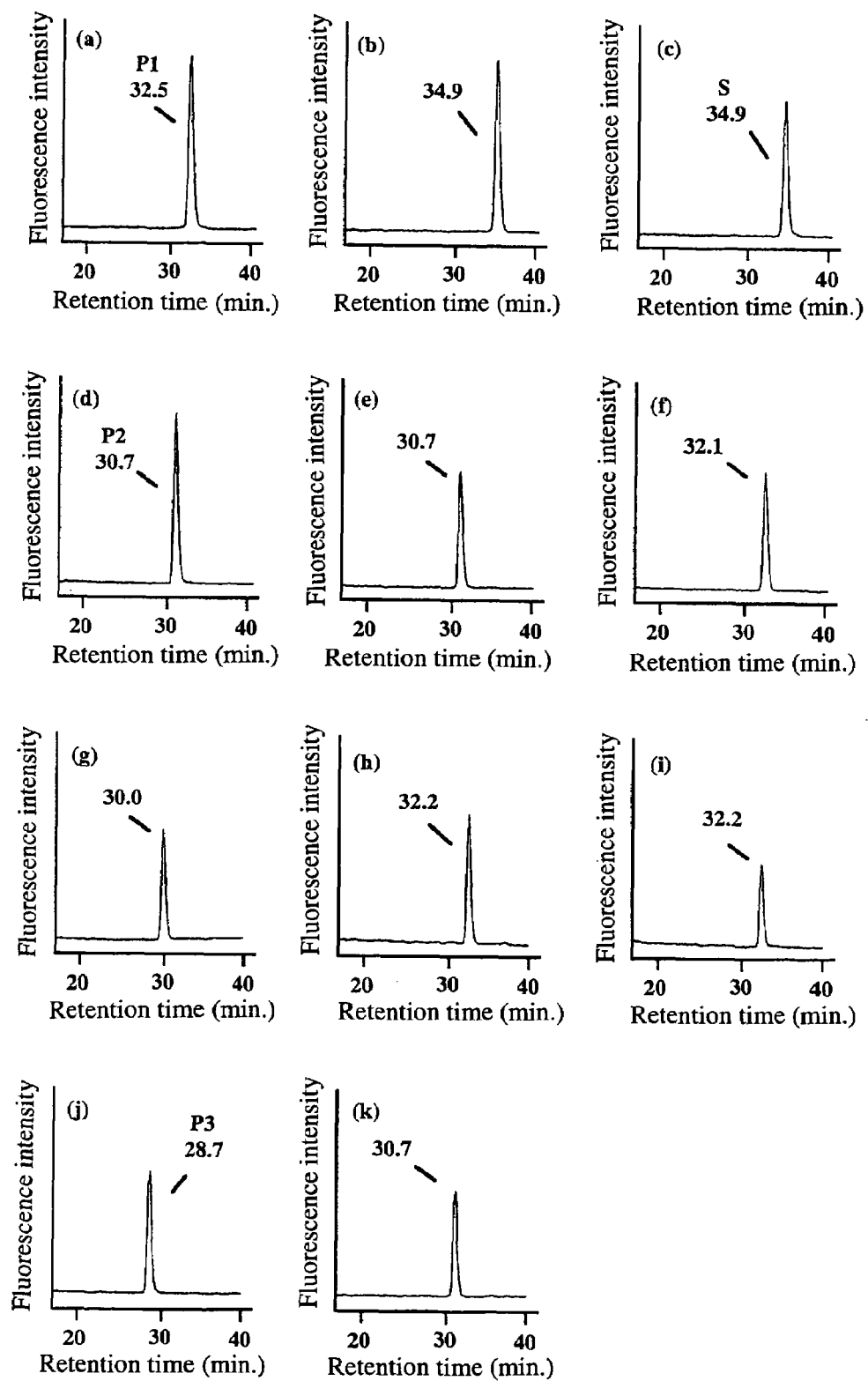

FIG. 15 shows the result obtained by treating the products (P1, P2 and P3) with various kinds of glycosidase and analyzing the obtained products by HPLC. (a) is the result of analysis of P1, (b) is the result of analysis of the product obtained by treating P1 with almond meal α1,3/4-fucosidase, (c) is the result of analysis of a substrate Galβ1-4GlcNAcβ1-3Galβ1-4GlcNAcβ1-3Galβ1-4GlcNAc-2AB (which is shown as S in the figure), (d) is the result of analysis of P2, and (e) is the result of analysis of the product obtained by treating P2 with almond meal α1,3/4-fucosidase. (f) is the result of analysis of the product obtained by treating P2 with Jack bean β-galactosidase, (g) is the result of analysis of the product obtained by treating P2 with Jack bean β-galactosidase and then with Jack bean β-N-acetylhexosaminidase, (h) is the result of analysis of the product obtained by treating P2 with Jack bean β-galactosidase, Jack bean β-N-acetylhexosaminidase and almond meal α1,3/4-fucosidase in sequence, (i) is the result of analysis of Galβ1-4GlcNAcβ1-3Galβ1-4GlcNAc-2AB, (j) is the result of analysis of P3, and (k) is the result of analysis of the product obtained by treating P3 with almond meal α1,3/4-fucosidase.

Figure 16:
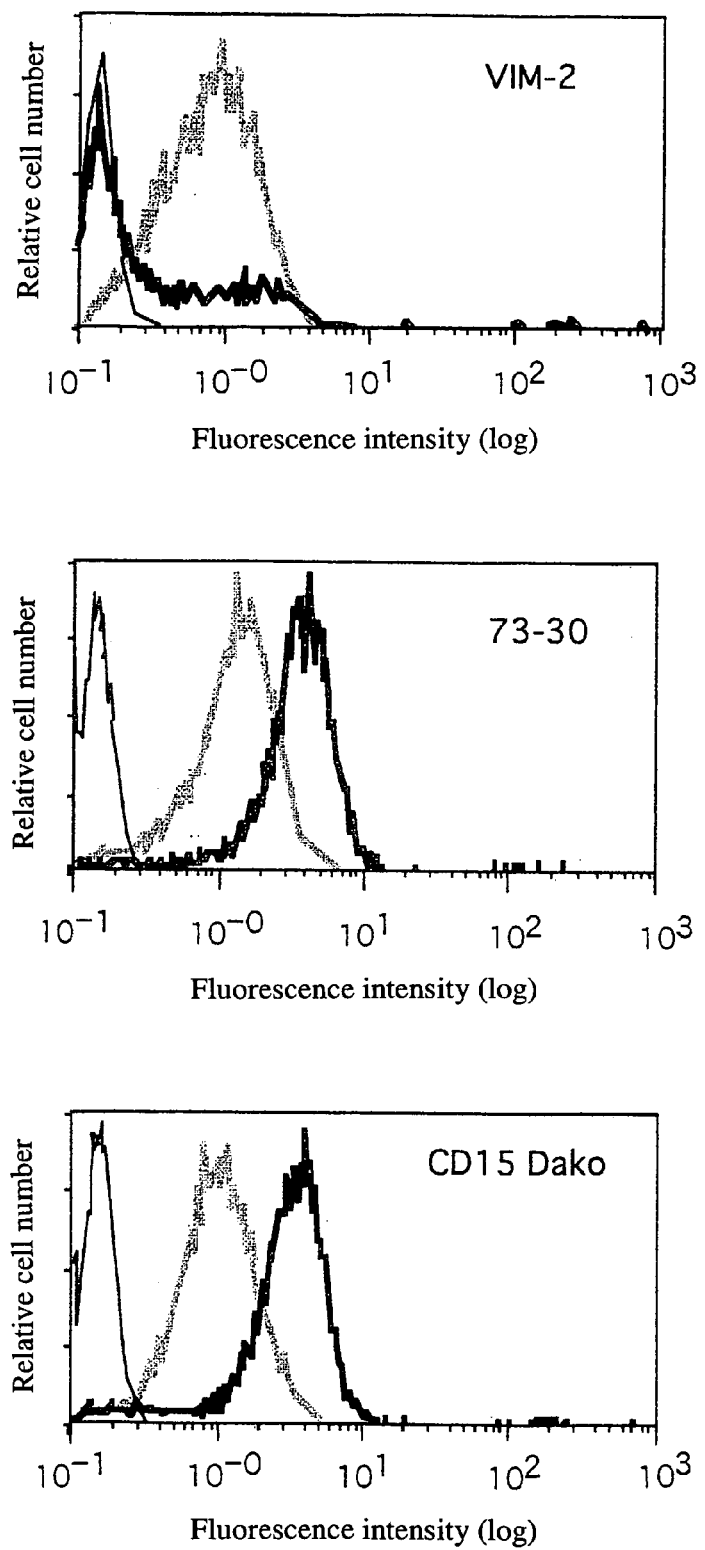

FIG. 16 shows the result of analysis of Namalwa cells by FACS, following an indirect fluorescent antibody straining of the Namalwa cells, into which a control vector, human Fuc-TIV expression plasmid or human Fux-TIX expression plasmid were introduced, using anti-VIM2 sugar chain antibody (which is denoted as VIX-2 in the figure), Le$^x$ sugar chain antibody 73-30(which is denoted as 73-30 in the figure), or anti-CD 15 antibody (which is denoted as CD-15 Dako in the figure). Thin black lines show the result of staining Namalwa cells into which a control vector was introduced, thick gray lines represent the result of staining Namalwa cells into which a human Fuc-TIV expression plasmid and thick black lines represent the result of staining Namalwa cells into which a human Fuc-TIX expression plasmid.

BEST MODE FOR CARRYING OUT THE INVENTION

Examples will now be shown as follows. Unless otherwise specified, genetic engineering techniques used herein are known techniques described in Molecular Cloning, $2^{nd}$ Edit.

Example 1

Cloning of a Novel Mouse α1,3-fucosyltransferase Gene (cDNA)

(1) Preparation of mRNA from Mouse Brain

About 30 μg of mRNA was prepared from BALB/c mouse brain using a mRNA extractor kit, Oligotex™-dT30<super> (manufactured by Roche). Reagents and methods were employed as described in the instructions attached to the kit.

(2) Construction of a Mouse Brain cDNA Library

Using 8 μg of mRNA obtained from the mouse brain in (1) above and a kit (SUPERSCRIPT Choice System for cDNA Synthesis manufactured by GIBCO BRL), double-stranded cDNAs were synthesized with oligo-dT as primers.

SfiI linkers were ligated to the both ends of the double-stranded cDNAs as described below.

[Addition of Sfi I Linker]

A single-stranded DNA represented by SEQ ID NO:6 and a single stranded DNA represented by SEQ ID NO:7 were synthesized using a 380A DNA synthesizer (manufactured by Applied Biosystems).

Each of the synthesized single-stranded DNAs 50 μg was independently dissolved in a separate 50 μl of buffer solution containing 50 mM Tris-HCl (pH 7.5), 10 mM $MgCl_2$, 5 mM dithiothreitol (hereinafter abbreviated as DTT), 0.1 mM EDTA and 1 mM ATP (hereinafter abbreviated as T4 kinase buffer). Then 30 units of T4 polynucleotide kinase (manufactured by Takara Shuzo Co., Ltd.) were added to each mixture, and allowed to carry out phosphorylation reaction for 16 hours at 37° C., thereby obtaining 11-bp and 8-bp linkers.

Four micrograms of the 11-bp linker, 2.9 μg of the 8-bp linker, and the double-stranded cDNAs synthesized as described above were dissolved in 45 μl of T4 ligase buffer. Then 1050 units of T4 DNA ligase were added to the mixture, and the mixture allowed to react for 16 hours at 16° C., so that the SfiI linkers were added to each of the double-stranded DNAs.

The resulting reaction mixture was subjected to agarose gel electrophoresis, and a DNA fragment of about a 1.5 kb or more was recovered.

Twenty four micrograms of expression cloning vector of pAMo [J. Biol. Chem., 268, 22782 (1993), also called pAMoPRC3Sc (Japanese Patent Laid Open Publication No. 05-336963)], expression cloning vector (Expression Cloning Vector), were dissolved in 590 μl of buffer containing 10 mM Tris-HCl (pH 7.5), 6 mM $MgCl_2$, 50 mM NaCl, 6 mM 2-mercaptoethanol (hereinafter abbreviated as Y-50 buffer).

Then 80 units of Sfi I (manufactured by Takara Shuzo Co., Ltd. Unless otherwise specified, restriction enzymes manufactured by Takara Shuzo Co. Ltd were used) were added to the mixture and allowed to digest for 16 hours at 37° C.

Forty units of BamH I were added to the reaction solution and allowed to digest for 2 hours at 37° C.

The reaction solution was then subjected to agarose gel electrophoresis, and a DNA fragment of about 8.8 kb was recovered.

DNAs (derived from 8 μg of mRNA) with Sfi I linkers prepared as described above was dissolved in 250 μl of T4 ligase buffer. Then 2 μg of about the ~8.8 kb DNA fragments and 2000 units of T4 DNA ligase were added to the solution, followed by ligation reaction for 16 hours at 16° C.

After the reaction, 5 μg of transfer RNA (tRNA) was added to the reaction solution. After ethanol precipitation, the precipitate was dissolved in 20 μl of a buffer containing 10 mM Tris-HCl (pH 8.0) and 1 mM EDTA (sodium ethylenediamine tetraacetic acid) (hereinafter abbreviated as TE buffer).

Using the reaction solution, *Escherichia coli* strain LE 392 (Molecular Cloning, $2^{nd}$ Edit) was transformed by the electroporation method [Nucleic Acids Res., 16, 6127 (1988)], and about a million ampicillin-resistant transformants were obtained, thereby constructing cDNA library.

(3) Cloning of a Gene (cDNA) Enhancing the Reactivity of Transformed Cells with an Anti-Lewis X Sugar Chain Antibody (PM-81)

Plasmids were prepared from the cDNA library (*E. coli*) as constructed in (2) above using a /plasmid/maxi kit, which is a plasmid preparation kit (merchandize No. 41031, manufactured by Qiagen).

After ethanol precipitation, the plasmids were dissolved in TE buffer to 1 μg/μl.

The plasmids (40 μg) were introduced into Namalwa cells by electroporation method [Cytotechnology, 3, 133 (1990)].

After introducing 4 μg of the plasmids per $1.6 \times 10^6$ cells, the cells were suspended in 8 ml of RPMI 1640 medium [the RPMI 1640 medium (manufactured by NISSUI PHARMACEUTICAL CO., LTD.) containing a 1/40 volume of 7.5% $NaHCO_3$, 3% of 200 mM L-glutamine solution (manufactured by GIBCO), 0.5% of penicillin/streptomycin solution (manufactured by GIBCO, 5000 units/ml of penicillin, 5000 μg/ml of streptomycin), and were cultured in a $CO_2$ incubator for 24 hours at 37° C.

After culturing, G418 (manufactured by GIBCO) was added to the medium to 0.5 mg/ml followed by culturing for 10 days, thereby obtaining stable transformants.

The transformants were cultured in RPMI1640 containing 0.5 mg/ml of G418. The resulting approximately $4 \times 10^7$ cells were subjected to indirect fluorescent antibody staining using PM-81, which was an antibody for the Lewis X sugar chain.

Detailed techniques employed are as shown below.

About $4 \times 10^7$ stable transformed cells were added to a 50 ml centrifugation tube (2059 tube: manufactured by Falcon) for centrifugation (130×g, 10 minutes), and the cells were collected.

The collected cells were washed with 20 ml of phosphate buffer PBS containing 0.1% sodium azide (A-PBS: 8 g/l NaCl, 0.2 g/l KCl, 1.15 g/l $Na_2HPO_4$ (anhydrous), 0.2 g/l $KH_2PO_4$, 0.1% sodium azide).

0.5 ml of the anti-Lewis x sugar chain antibody (PM-81) diluted to about 10 μg/ml using A-PBS was added to the washed cells for suspension, then allowed to react for 1 hour at 4° C.

After the reaction, the cells were washed once with 20 ml of A-PBS. Subsequently the cells were suspended in 300 μl of a solution, which had been prepared by diluting anti-mouse IgM antibodies (manufactured by CAPPEL) fluorescent-labeled with fluorescein isothiocyanate (FITC) at 1:16 with A-PBS. The suspension was allowed to react for 30 minutes at 4° C.

After the reaction, the cells were washed once with A-PBS, and then suspended in 1 ml of A-PBS. Cells with high fluorescent intensity (top 2.0%) were aseptically separated and collected using a fluorescence activated cell sorter (EPICS Elite Plow Cytometer; manufactured by COULTER).

The collected cells were cultured in RPMI1640 media, containing 0.5 mg/ml of G418. After growing, cells with high fluorescent intensity were aseptically separated and collected in the same manner as described above.

The above procedure was repeated to separate and concentrate cells with high fluorescent intensity.

In the second procedure, the cells with high fluorescent intensity (top 1.5%); in the third procedure, the cells with high fluorescent intensity (top 1.5%); and in the forth procedure, the cells with high fluorescent intensity (top 1.0%) were separated and collected.

Therefore, cells with enhanced fluorescent intensity, that is, cells, in which the amount of the Lewis x sugar chain was increased, were recovered by the above separation procedure.

After the cells were cultured in RPMI1640 medium containing 0.5 mg/ml of G418, plasmids were recovered from about $2 \times 10^6$ cells by Hirt procedure [(Mol. Cell. Biol., 8, 2837 (1988)].

The plasmids were introduced into *Escherichia coli* strain LE397 by electroporation method [(Nucleic Acids Res., 16, 6127, (1988)], thereby recovering ampicillin-resistant transformants.

Plasmids were prepared from 40 transformants obtained as described above. Each of the plasmids was excised with restriction enzymes (Hind III and Asp718) to examine the structure of the inserted cDNA.

The plasmids were subjected to phenol-chloroform extraction followed by ethanol precipitation, thereby recovering the plasmids.

The plasmids were dissolved in 10 μl of TE buffer. Then each of the plasmids was introduced into Namalwa cells by electroporation method [Cytotechnology, 3, 133 (1990)].

After introducing 3 μl of the plasmids prepared as described above or 4 μg of pAMo (control plasmid) per $1.0 \times 10^6$ to $1.6 \times 10^6$ cells (200 μl) by electroporation method, the cells were suspended in 8 ml of RPMI1640 media and then cultured in a $CO_2$ incubator for 24 hours at 37° C.

After culturing, the medium was supplemented with G418 (manufactured by GIBCO BRL) to 0.5 mg/ml followed by culturing for another 10 to 14 days, thereby obtaining transformed cells.

The resultant transformed cells were subjected to indirect fluorescent antibody staining using an anti-Lewis x sugar chain antibody (PM-81). In the cells into which a plasmid named pAMo-mFT9 had been introduced, reactivity (peak value of histogram) against the anti-Lewis x sugar chain antibody (PM-81) increased by about 20 times, compared with the cells into which pAMo had been introduced.

The above results reveal that cDNA inserted in the plasmid pAMo-mFT9 causes increased reactivity of the transformed cells against the anti-Lewis x sugar chain antibody (PM-81).

Indirect fluorescent antibody staining using the anti-Lewis x sugar chain antibody (PM-81) was performed as follows.

About 1×10⁶ transformed cells were added to a microtube (1.5 ml: manufactured by Eppendolf) and then the cells were collected by centrifugation (550×g, 7 minutes).

The cells were washed with 0.9 ml of A-PBS, suspended by adding 20 μl of the anti-Lewis x sugar chain antibody (PM-81) that had been diluted with A-PBS to about 10 μg/ml, and then allowed to react for 1 hour at 4° C.

After the reaction, the cells were washed once with 0.9 ml of A-PBS, suspended by adding 20 μl of a solution, which had been prepared by diluting anti-mouse IgM antibodies (manufactured by CAPPEL) fluorescent-labeled with FITC at 1:16 using A-PBS. Then the products were allowed to react for 30 minutes at 4° C.

After the reaction, the cells were washed once with 0.9 ml of A-PBS, and then suspended in 0.6 ml of A-PBS, followed by the analysis using a fluorescence activated cell sorter. In a control experiment, similar analysis was produced using A-PBS instead of the anti-Lewis x sugar chain antibody (PM-81).

(4) Determination of Nucleotide Sequence of a cDNA Inserted in a Plasmid pAMo-mFT9.

After making a restriction map of the cDNA contained in the plasmid pAMo-mFT9 obtained in (3) above, DNA fragments derived from the cDNA were subcloned into pBluescript II SK(−), and the whole nucleotide sequence of the cDNA was determined. The nucleotide sequences were determined using a DNA sequencer 377 and a kit (both manufactured by Perkin-Elmer) according to the instructions attached to the kit.

By assembling the results together, the whole nucleotide sequence (2170 bp) of the cDNA contained in the plasmid pAMo-mFT9 was determined.

The nucleotide sequence of the cDNA is shown in SEQ ID NO:3.

The cDNA encoded a polypeptide consisting of 359 amino acids having a structure characteristic to glycosyl transferases. The polypeptide shared 35% to 38% homology to five types of human α1,3-fucosyltransferases that had been cloned so far at the amino acid level, suggesting that the polypeptide was a novel α1,3-fucosyltransferase. The amino acid sequence of the polypeptide was shown in SEQ ID NO:1.

The polypeptide was considered to contain an N-terminal cytoplasmic region comprising 10 amino acids, which is followed by a transmembrane domain, rich in hydrophobicity, comprising 20 amino acids, a stem region comprising at least 25 amino acids, and a C-terminal region, which is most of the remaining part including catalytic region. It was estimated that the stem region comprised at least 25 amino acids based on the findings (J. Biol. Chem., 269, 14730–14737, 1994, J. Biol. Chem., 270, 8712–8722, 1995, Glycobiology, 7, 921–927, 1997) regarding comparison of the amino acid sequence homology between the novel and other α1,3-fucosyltransferases, and regarding the stem and catalytic regions of other α1,3-fucosyltransferases. Accordingly, a polypeptide containing a sequence of amino acid position 56 to 359 should contain the catalytic region.

Hereinafter the cDNA is called mouse Fuc-TIXcDNA, a polypeptide encoded by the cDNA is called mouse Fuc-TIX.

Example 2

Synthesis of the Lewis x Sugar Chain and the Lewis y Sugar Chain in a Human Culture Cell into which a Mouse Fuc-TIX Expression Plasmid obtained in Example 1 has been Introduced A control plasmid (pAMo) and a mouse Fuc-TIX expression plasmid (pAMo-mFT9) were separately dissolved in TE buffer to 1 μg/μl, introduced into Namalwa cells by eletroporation method, thereby obtaining transformed cells.

The transformed cells were subjected to indirect fluorescent antibody staining using an anti-Lewis x sugar chain antibodies (PM-81 or 73-30), an anti-Lewis y sugar chain antibody (AH-6), and an anti-sialyl Lewis x sugar chain antibody (KM93).

Indirect fluorescent antibody staining was performed according to the methods described in Example 1 (3). When compared to the cells into which pAMo had been introduced, the cells into which pAMo-mFT9 had been introduced showed an approximately 20-fold increase in reactivity (peak value of histogram) against each of the anti-Lewis x sugar chain antibodies (PM-81 and 73-30), and an approximately 7-fold increase in the reactivity against the anti-Lewis y sugar chain antibody (AH-6).

Figure 1:
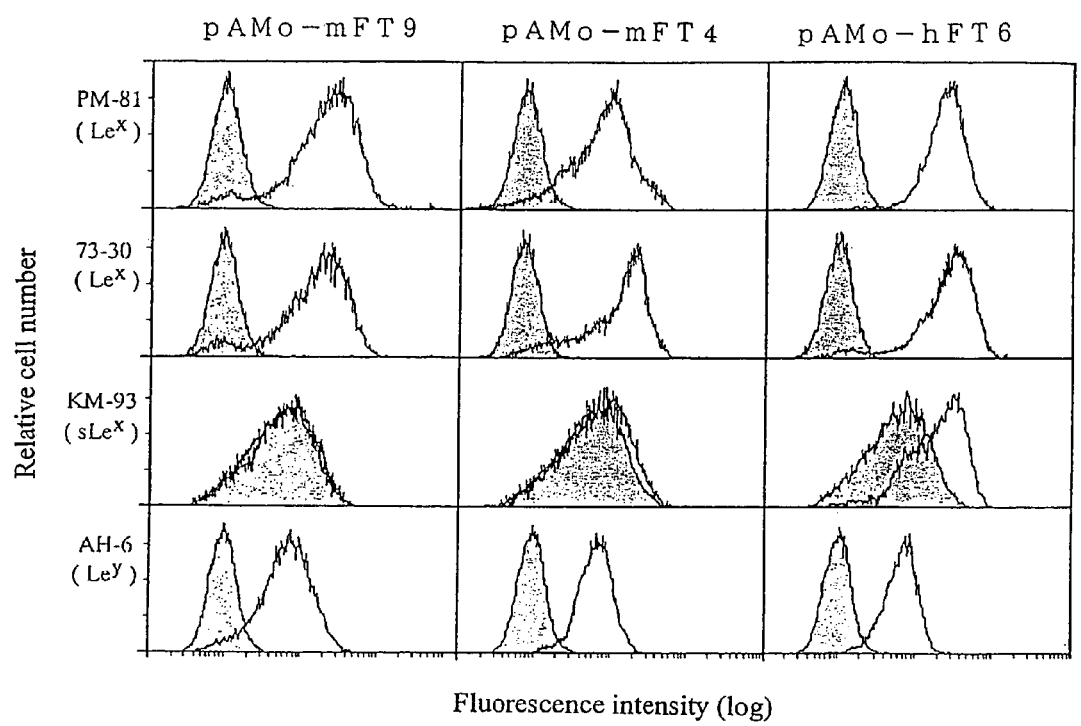
FIG. 1 shows the result obtained by FACS analysis of the Namalwa cells transfected with a control plasmid (pAMo), a mouse Fuc-TIX expression plasmid (pAMo-mFT9), a mouse Fuc-TIV expression plasmid (pAMo-mFT4), or a human Fuc-TVI expression plasmid (pAMo-hFT6), which were subjected to indirect fluorescent antibody straining with anti-Lewis x sugar chain antibody (PM-81, 73-30), anti-Lewis y sugar chain antibody (AH-6), or anti-sialyl Lewis x sugar chain antibody (KM93). Shaded histograms are of Namalwa cells transfected with a control plasmid.

On the other hand, almost no change was observed in the reactivity against the anti-sialyl Lewis x sugar chain antibody (KM93) (see FIG. 1).

For comparison, similar analyses were performed for Namalwa cells expressing other α1,3-fucosyltransferases (mouse Fuc-TIV or human Fuc-TVI). That is, Namalwa cells, into which a mouse Fuc-TIV expression plasmid (pAMo-mFT4) or a human Fuc-TVI expression plasmid (pAMo-hFT6) had been introduced, were prepared. Then the cells were examined for the reactivity against the above antibodies (see FIG. 1).

Figure 2:
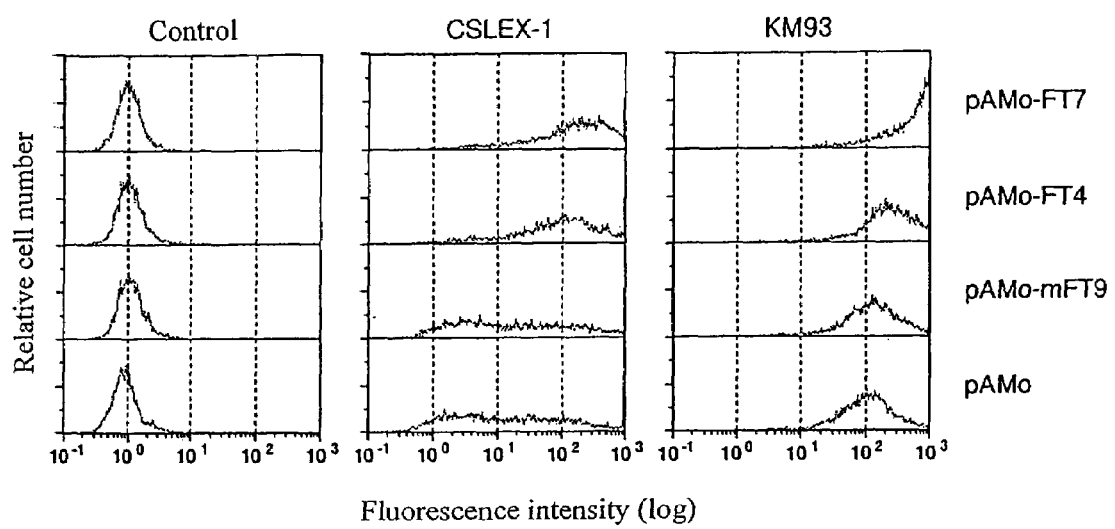
FIG. 2 shows the result obtained by FACS analysis of the Namalwa KJM-1 cells transfected with a control plasmid (pAMo), a mouse Fuc-TIX expression plasmid (pAMo-mFT9), a human Fuc-TIV expression plasmid (pAMo-FT4), or a human Fuc-TVII expression plasmid (pAMo-FT7) which were subjected to indirect fluorescent antibody straining with anti-sialyl Lewis x sugar chain antibody (CSLEX-1, KM93). For control sample, A-PBS was used instead of the first antibody.

Similarly, Namalwa KJM-1 cells, into which a control plasmid (pAMo), a mouse Fuc-TIX expression plasmid (pAMo-mFT9), a human Fuc-TIV expression plasmid (pAMo-FT4), or a human Fuc-TVII expression plasmid (pAMo-FT7) had been introduced, were obtained. The cells were subjected to indirect fluorescent antibody staining using the anti-Lewis x sugar chain antibody (KM380) and an anti-sialyl Lewis x sugar chain antibodies (CSLEX-1 or KM93) (see FIG. 2).

Figure 3:
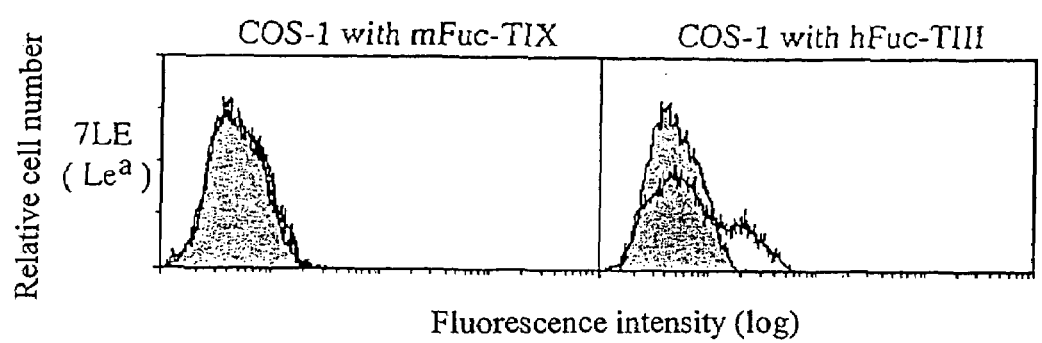
FIG. 3 shows the result obtained by FACS analysis of the COS-1 cells transfected with a control plasmid (pCDM8), a mouse Fuc-TIX expression plasmid (pCDM8-mFT9), or a human Fuc-TIII expression plasmid (pCDM8-Le), which were subjected to indirect fluorescent antibody straining with anti-Lewis a sugar chain antibody (7LE). Shaded histograms are of COS cells transfected with a control plasmid.

Further, COS-1 cells, into which a control plasmid (pCDM8), a mouse Fuc-TIX expression plasmid (pCDM8-mFT9), or a human Fuc-TIII expression plasmid (pCDM8-Le) had been introduced, were prepared. The cells were subjected to indirect fluorescent antibody staining using the anti-Lewis a sugar chain antibody (7LE, manufactured by SEIKAGAKU CORPORATION) (see FIG. 3).

Methods to construct each expression plasmid and methods to introduce it into COS-1 cells are described in Example 3.

The results suggest that Fuc-TIX can synthesize the Lewis x sugar chain and the Lewis y sugar chain in transformed cells but cannot synthesize the sialyl Lewis x sugar chain and the Lewis a sugar chain. This enzymatic property differs from that of any α1,3-fucosyltransferases that has been cloned so far. Therefore Fuc-TIX was found to be a novel α1,3-fucosyltransferase having novel substrate specificity.

The substrate specificity of Fuc-TIX is analogous to that of Fuc-TIV among α1,3-fucosyltransferases that have been cloned so far. However there is a clear difference between Fuc-TIV and Fuc-TIX in that Fuc-TIV synthesizes sialyl Lewis x sugar chain while Fuc-TIX does not synthesize it.

Moreover, these results show that by expressing Fuc-TIX in cells sugar chains containing the Lewis x sugar chain or the Lewis y sugar chain, and a complex sugar chains containing the said sugar chains can be newly synthesized.

Therefore, it is concluded that Fuc-TIX expressing cells are used as hosts to produce and secrete useful glycoproteins so that the Lewis x sugar chain or the Lewis y sugar chain can be added to the glycoproteins to be produced and secreted.

Example 3

In Vitro Substrate Specificity of Mouse Fuc-TIX

In vitro substrate specificity of Fuc-TIX encoded by the mouse Fuc-TIX cDNA obtained in Example 1 was examined as follows.

To express the mouse Fuc-TIX in animal cells, the mouse Fuc-TIX cDNA was subcloned into an expression vector pCDM8 for animal cells as described below.

That is, a 1.2-kb HindIII—AseI fragment containing an open reading frame (ORF) of the mouse Fuc-TIX cDNA was isolated from pAMo-mFT9. The cut ends were blunt-ended with T4 DNA polymerase, then subcloned into an EcoRV site of pBluescript SK(−).

A plasmid, in which the cDNA was subcloned in a direction such that the 5' and 3' sides of the cDNA was present near HindIII and PstI sites of the cloning sites, respectively, was selected. The plasmid was excised with HindIII and PstI to isolate a 1.2-kb fragment containing the mouse Fuc-TIX cDNA.

The 1.2-kb fragment was subcloned between HindIII and PstI of pCDM8 to construct a mouse Fuc-TIX expression plasmid pCDM8-mFT9.

To compare substrate specificity of the novel α1,3-fucosyltransferase with other α1,3-fucosyltransferases, expression plasmids pCDM8-Le (human Fuc-TIII), pCDM8-mFT4, and pCDM8-hFT6 were constructed (Glycoconjugate J., 12, 802–812, 1995, J. Biol. Chem., 269, 29271–29278, 1994), into which a human Fuc-TIII cDNA, a mouse Fuc-TIV cDNA, and a human Fuc-TVI cDNA were subcloned into pCDM8, respectively.

pCDM8-mFT4 was constructed as described below.

mRNAs were prepared from Balb/c mouse stomach in the same manner as described in Example 1, and cDNAs were synthesized.

PCR was performed for the cDNAs using primers shown in SEQ ID NOS:8 and 9, thereby amplifying ORF of the mouse Fuc-TIV cDNA.

The each primer used for the amplification has an EcoRI recognition site at its end. The amplified fragments were excised with EcoRI, then subcloned into an EcoRI site of a vector pBluescript SK(−) to constructpBS-mFT4.

On the other hand, the vector pCDM8 was excised with Hind III, and then the excised ends were blunt-ended with T4 DNA polymerase. Subsequently a vector in which the HindIII site was converted to an EcoRI site was constructed by ligating an EcoRI linker with the digested vector.

An EcoRI fragment containing the mouse Fuc-TIV cDNA of pBS-mFT4 was subcloned into the EcoR I site of the vector, thereby constructing pCDM8-mFT4.

Each α1,3-fucosyltransferase expression plasmid (15 µg) was introduced into 1×10$^7$ COS-1 cells.

This introduction was performed by electroporation method using a gene pulser (manufactured by Bio-Rad) according to the Bio-Rad's instructional manual attached thereto. At this time, 1 µg of a luciferase expression vector, which was constructed by inserting β-actin promoter into a Hind III site of a vector pSVOA/L [Experimental Medicine, 7, 96, (1989)] was co-introduced as an index of gene transfer efficiency.

After the gene introduction, COS-1 cells were dispensed into three dishes for cell culture with a diameter of 15 cm and then cultured for 48 hours.

Total RNA was extracted from the cells in one of the three dishes in the same manner as described in Example 4, subjected to quantitative RT-PCR, measuring the amount of transcription for each α1,3-fucosyltransferase gene.

The cells in the remaining two dishes were collected, suspended in a solution (20 mM HEPES (pH 7.4), 2% TrironX-100), then ultrasonicated for a short time period, thereby preparing cell lysate. The protein concentration of the cell lysate was measured using a micro BCA protein assay reagent kit (manufactured by PIERCE).

The enzymatic activities of luciferase and α1,3-fucosyltransferase were measured using the cell lysate.

Luciferase activity was measured by methods described in the document (J. Biol. Chem., 269, 29271–29278, 1994) to test the efficiency of the gene introduction.

In any COS-1 cells into which genes had been introduced, the luciferase activity was almost constant within an error margin of ±20%, and no significant difference was observed in gene introduction efficiency among the fucosyltransferase genes.

Moreover, the introduction efficiency and the expression level of each fucosyltransferase gene measured by RT-PCR were almost the same.

To normalize the gene introduction efficiency precisely, each cell lysate was diluted to give a constant luciferase activity per volume.

Preparation of pyridylaminated oligosaccharide substrates and measurement of the activity were performed according to a known technique (Japanese Patent Laid Open Publication No. 06-823021, J. Biol. Chem. 269, 14730–14737, 1994).

That is, the activity was measured by allowing reaction to occur in 10 µl of assay solution [50 mM cacodylic acid-HCl (pH 6.8), 5 mM ATP (SIGMA), 75 µM GDP-Fuc (SIGMA), 10 mM L-Fuc (SIGMA), 25 µM pyridylaminated oligosaccharide substrate, the above cell lysate] for 2 hours at 37° C., subjecting the products to high-performance liquid chromatography (HPLC) to identify the products.

Substrates used herein were the followings: Lacto-N-neotetraose (Galβ1-4GlcNAcβ1-3Galβ1-4Glc; hereinafter referred to as LNnT) and Lacto-N-tetraose (Gal β1-3GlcNAcβ1-3Galβ1-4Glc; hereinafter referred to as LNT), both manufactured by Oxford Glycosystem and fluorescent-labeled with aminopyridine; and Sialyllacto-N-neotetraose (NeuAcα2-3Galβ1-4GlcNAcβ1-3Galβ1-4Glc; hereinafter referred to as α2,3-sialyl LNnT) that had been fluorescent labeled with aminopyridine, which was prepared by the reaction using a secreted α2,3-sialyltransferase (ST3Gal IV) and LNnT fluorescent-labeled with aminopyridine as a substrate.

Standard substrates used herein were the followings: Lacto-N-fucopentaose II (Galβ1-3(Fucα1-4)GlcNAcβ1-3Galβ1-4Glc; hereinafter referred as LNFP-II) and Lacto-N-fucopentaose III, (Galβ1-4(Fucα1-3)GlcNAcβ1-3Galβ1-4Glc; hereinafter referred as LNFP-III, both manufactured by Oxford Glycosystem and fluorescent-labeled with aminopyridine; and Sialyllacto-N-fucopentaose III) (NeuAcα2-3Galβ1-4(Fucα1-3)GlcNAcβ1-3Galβ1-4Glc; α2,3-sialyl LNFP-III) that had been prepared by the reaction using a secreted enzyme of Fuc-TVI and α2,3-sialylLNnT fluorescent-labeled with aminopyridine as a substrate.

The substrates were fluorescent-labeled according to a conventional method (Agric. Biol. Chem., 54, 2169, 1990).

Each of the substrates was allowed to react in assay solution with or without GDP-Fuc (sugar donor), then analyzed with HPLC. The peaks that appeared only in the assay solution containing GDP-Fuc were considered to be products.

After completion of the reaction, the assay solution was treated for 3 minutes at 100° C., then centrifuged at 10,000×g for 5 minutes, obtaining the supernatant. An aliquot of the supernatant was subjected to HPLC.

HPLC was performed using a TSK-gel ODS-80Ts column (4.6×300 mm, TOSOH CORPORATION) under the following conditions: effluent was 0.02 M ammonium acetate buffer (pH 4.0), elution temperature was 35° C., and flow rate was 1 ml/min.

The products were detected using a fluorescent spectrum photometer FP-920 (JASCO Corporation) at excitation wavelength of 320 nm and emission wavelength of 400 nm.

Determination of the products were identified based on an index wherein elution time of a product is identical to that of a standard sugar chain.

The products were determined by comparing fluorescent intensities using pyridylaminated lactose as a standard.

The amount of reaction products was normalized based on the amount of transcription of each α1,3-fucosyltransferase gene measured as described above, and the result was determined as activity.

Relative activity of each α1,3-fucosyltransferase against each substrate was obtained, when the activity of human Fuc-TVI, to the substrate α2,3-sialylLNnT as a substrate, was taken as 100.

Table 1 shows the results. For COS-1 cells, to which a control plasmid (pCDM8) had been introduced, no activity was detected when any substrates were used.

TABLE 1

Relative activity of α1,3-fucosyltransferases for each substrate

| Substrate | Mouse Fuc-TIX | Mouse Fuc-TIV | Human Fuc-TIII | Human Fuc-TVI |
|---|---|---|---|---|
| LNT | 0 | 0 | 123.3 | 0 |
| LNnT | 83.8 | 51.6 | 32.3 | 63.7 |
| α2,3-sialyl LNnT | 0 | 4.5 | 16.4 | 100 |

Mouse Fuc-TIX showed strong activity for LNnT only.

Human Fuc-TIII showed activity for all substrates, LNT, LNnT, and α2,3-sialyl LNnT, with its strongest activity for LNT.

Mouse Fuc-TIV showed strong activity for LNnT, and weak activity for α2,3-sialyl LNnT.

Human Fuc-TVI showed activity for α2,3-sialyl LNnT and LNnT, with its strongest activity for α2,3-sialyl LNnT.

Since in vitro substrate specificity of Fuc-TIX differs from the substrate specificity of any α2,3-fucosyltransferases that had been purified or cloned so far, Fuc-TIX was proved to be an α1,3-fucosyltransferase having novel substrate specificity.

In vitro substrate specificity of Fuc-TIX matched well with that of Fuc-TIX in the cells shown in Example 2. Moreover, comparison with other α1,3-fucosyltransferases, revealed that Fuc-TIX showed strong activity to transfer fucose to GlcNAc residue of LNnT via α1,3-linkage. Therefore, it was demonstrated that Fuc-TIX was useful to synthesize the Lewis x sugar chains.

Example 4

Expression of the Fuc-TIX Gene in Various Organs (1) Northern Blot Analysis

Poly (A)+ RNA was isolated from each organ of a mouse (brain, thymus, stomach, liver, spleen, kidney, large intestine, uterus, ovary, lung, testis, small intestine, and epididymis) in the same manner as described in Example 1. Five μg of the isolated Poly (A)+ RNA was denatured by heating at 65° C. for 5 minutes in a denaturation solution (50% (v/v) formamide, 2.2 M formaldehyde, 20 mM MOPS (3-(N-morpholino) propanesulfonate (pH 7.0), 5 mM sodium acetate, 1 mM EDTA), and then subjected to electrophoresis with 1% agarose gel containing 2.2 M formaldehyde.

After electrophoresis, the RNAs in the gel were blotted on a nitrocellulose filter (Optimal BA-S85; Schleicher & Schuell), and then fixed by heating under reduced pressure for 1 hour at 80° C.

The filter was dipped in a hybridization solution [5×SSPE (750 mM NaCl, 50 mM NaH$_2$PO$_4$, 5 mM EDTA; pH 7.4), 5× Denhart's solution (0.1% ficoll, 0.1% poly(vinyl)pyrrolidone, 0.1% bovine serum albumin), 1% SDS (sodium dodecyl sulfate), 0.2 mg/ml of salmon sperm DNA (Pharmacia Biotech)] to perform pre-hybridization.

After pre-hybridization, a probe was added to the solution, followed by hybridization at 65° C.

The probe used herein was prepared by labeling a HindIII-AseI fragment containing ORF of mouse Fuc-TIX in pAMo-mFT9 with $^{32}$P using a multi prime DNA labelling system (Amersham).

After hybridization, the filter was washed twice with 0.1×SSC (15 mM NaCl, 1.5 mM sodium citrate) containing 0.1% SDS, followed by exposure of the filter to an imaging plate, by which bands of mouse Fuc-TIX mRNAs were detected using a Bio-imaging analyzer BAS2000 (FUJI PHOTO FILM CO.,LTD).

Figure 4:
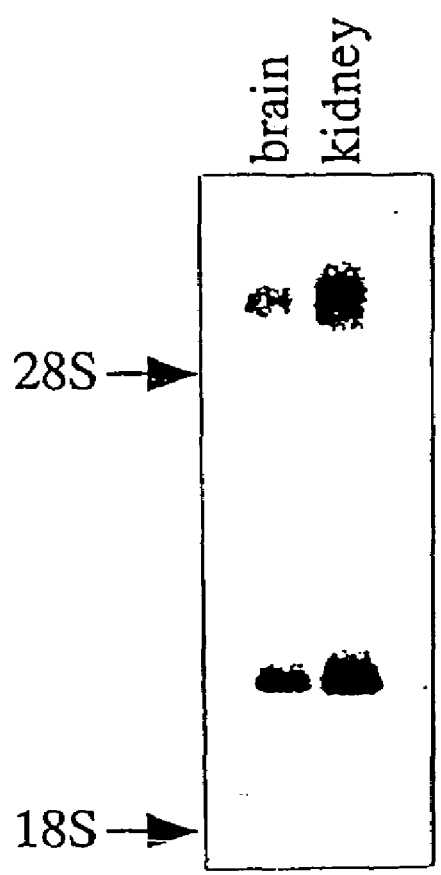
FIG. 4 shows the result of northern hybridization performed using Poly (A)$^+$ RNA from each mouse organ in order to determine the distribution of mouse Fuc-TIX transcripts. The results are shown only regarding brain and kidney which exhibited a signal.

Two types of bands, 5.5- and 3.0-kb bands, were detected in brain and kidney, but no band was detected in other organs. Therefore, it was found that the Fuc-TIX gene was mainly expressed in kidney and brain. FIG. 4 shows the result of Northern blot analysis for brain and kidney.

(2) Determination of Fuc-TIX Transcripts in Various Organs Using RT-PCR Quantitative RT-PCR was Conducted to Determine the Expression Level of the Fuc-TIX Gene in Each Organ.

The standard plasmid used to make a calibration curve was pBS-mFT9 which had been prepared by subcloning an approximately 1.8-kb HindIII-KpnI fragment containing the Fuc-TIX cDNA of pAMo-mFT9 into between HindIII and KpnI of a vector pBluescript SK(−).

pBS-mFT9d lacking 127 bp between XcmI and Bpu1120I in the Fuc-TIX cDNA was constructed by cleaving pBS-mFT9 with restriction enzymes XcmI and Bpu1120I, blunt-ending the product with T4 DNA polymerase, followed by re-ligation.

The resultant pBS-mFT9d was used as an internal control plasmid for normalization of samples in RT-PCR.

Mouse β-actin cDNA was obtained according to the method employed to obtain the mouse Fuc-TIV cDNA as described in Example 3. The mouse β-actin cDNA was used as control to be an index for cDNA synthesis.

Using single strand cDNAs derived from mRNA of mouse stomach as templates, PCR was performed with primers shown in SEQ ID NOS:10 and 11, thereby amplifying a mouse β-actin cDNA.

The primer of SEQ ID NO:10 used for the amplification had an EcoRI recognition sequence at its end; the primer of SEQ ID NO:11 had a HindIII recognition sequence at its end. The amplified fragments were excised with EcoRI and HindIII, subcloned into between EcoRI site and HindIII site of a vector pBluescript SK(−) to construct pBS-mβ-actin as a standard plasmid for β-actin gene.

pBS-mβ-actind lacking 208 bp between MscI-BstEII in the β-actin cDNA was constructed by excising pBS-mβ-actin with restriction enzymes MscI and BstEII, blunt-ending the ends with T4 DNA polymerase, followed by re-ligation. The obtained pBS-mβ-actind was used as an internal control plasmid.

For comparison, the distribution of expression of the mouse Fuc-TIV gene was also studied. pBS-mFT4 constructed in Example 3 was used as a standard plasmid. Further, pBS-mFT4d lacking 168 bp between EcoNI-Csp45I in the mouse Fuc-TIV cDNA was constructed by excising pBS-mFT4 with restriction enzymes EcoNI and Csp45I, blunt-ending the ends with T4 DNA polymerase, followed by re-ligation. The resultant pBS-mFT4d was used as an internal control plasmid.

Total RNA was extracted from each tissue of an adult BALB/c mouse (brain, thymus, stomach, liver, spleen, kidney, large intestine, uterus, ovary, lung, heart, testis, small intestine and epididymis) by the acid guanidium thiocyanate phenol—chloroform method (Anal. Biochem. 162,156–159).

Five units/ml each of deoxyribonuclease I (manufactured by Life Technologies) was added to 6 μg each of the total RNA and allowed to react for 5 minutes at room temperature.

After reaction, the enzyme was inactivated by heating the product for 15 minutes at 65° C.

cDNA was synthesized for each of the resulting total RNA by SUPERSCRIPT™ Preamplification System for First Strand cDNA System (Life Technologies) using oligo (dT) primers. After reaction in 20 μl of the reaction solution, the solution was diluted 50-fold with water and stored at −80° C. until use.

PCR was performed using DNA polymerase AmpliTaq Gold™ (Parkin Elmer) in 50 μl of reaction solution [10 mM Tris-HCl (pH 8.3), 50 mM KCl, 1.5 mM $MgCl_2$, 0.2 mM dNTP, 0.001% (w/v) gelatin, 0.2 μM gene specific primer] containing 10 μl of the abovementioned cDNA derived from each tissue and 10 μl (10 fg) of the internal control plasmid.

The nucleotide sequences of Fuc-TIX specific primers are shown in SEQ ID NOS: 12 and 13, those of β-actin specific primers are shown in SEQ ID NOS: 14 and 15, and those of Fuc-TIV specific primers are shown in SEQ ID NOS: 16 and 17.

Using these primers, a 530-bp fragment can be amplified for the Mouse Fuc-TIX cDNA, a 403-bp fragment from pBS-mFT9d, a 792-bp fragment for the β-actin cDNA, and a 584-bp fragment from pBS-mβ-actind. Moreover, a 511-bp fragment can be amplified for the mouse Fuc-TIV cDNA, and a 343-bp fragment from pBS-mFT4d.

PCR reaction was performed by 38 to 42 cycles for Fuc-TIX and Fuc-TIV; 22 to 26 cycles for β-actin. Each of the reaction cycles consisted of heating for 11 minutes at 95° C., 1 minute at 95° C., 1 minute at 65° C., and then 2 minutes at 72° C.

After 10 μl of the reaction solution was subjected to electrophoresis with 1% agarose gel, the gel was stained with ethidium bromide, and then photographed. The picture was then scanned by NIH image system to measure the intensity of the staining of the amplified fragments, thereby determining the level of amplification.

PCR was performed using 1.25 fg, 2.5 fg, 5 fg, 10 fg, 20 fg, or 40 fg of the standard plasmids instead of cDNA derived from the tissues. The amount of the amplified fragments was measured, then the amount of cDNA and the amount of the corresponding amplified fragment were plotted so as to make a calibration curve.

The amount of the cDNA in each of the tissues was calculated from the calibration curve and the amount of the fragments amplified with cDNA in each tissue, and the obtained the amount of the cDNA in each tissue is considered to be transcription level of mRNA in each tissue. Since the β-actin gene is thought to be generally expressed in each tissue, its expression level should be at the same level in any tissues. That is, differences in the expression level of the β-actin gene among the tissues may be due to differences in efficiency of the cDNA synthetic reaction. Therefore, the expression level of the β-actin gene was also taken into consideration upon comparison of the expression level of the Fuc-TIX gene.

Figure 5:
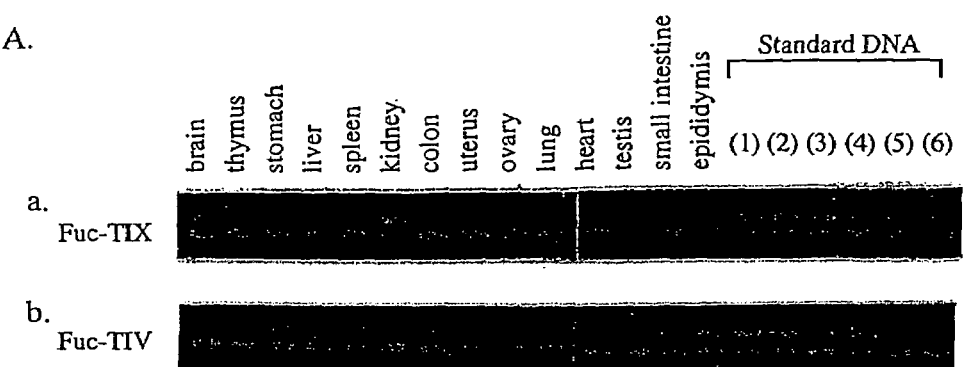
FIG. 5 shows the amount of mouse Fuc-TIX transcripts in each mouse organ which was detected by quantitative RT-PCR.
Figure 5:
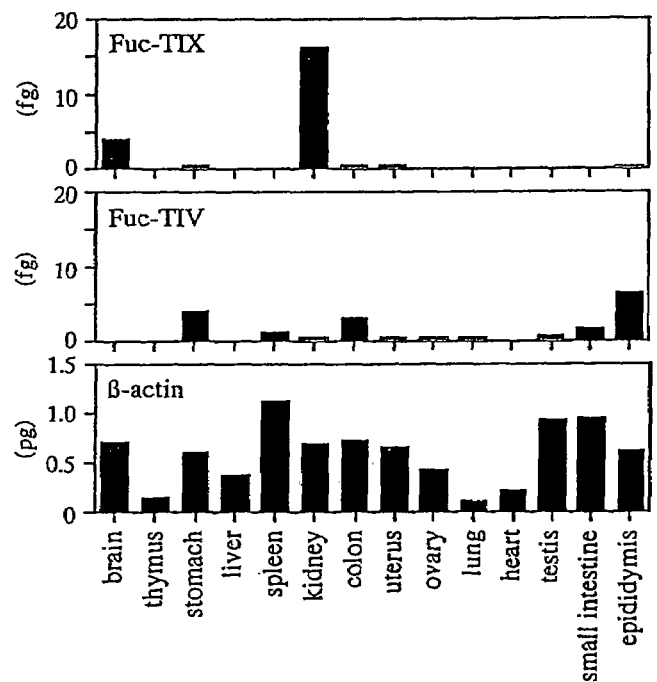

FIG. 5 shows the results.

It was found that the Fuc-TIX gene is expressed most abundantly in kidney, followed by brain. Further, the Fuc-TIX gene was also expressed in stomach, large intestine, uterus, and epididymis. However, no expression was observed in thumus, liver, spleen, ovary, lung, heart, testis, and small intestine. The expression pattern of the mouse Fuc-TIX gene differed clearly from that of the mouse Fuc-TIV gene (see FIG. 5).

Example 5

Analysis of the Expression Pattern of the Mouse Fuc-TIX Gene in Brain by In Situ Hybridization A part of the mouse Fuc-TIX cDNA was amplified using primer sets whose nucleotide sequences are shown in SEQ ID NOS: 18 and 19. Then the amplified fragment was subcloned into a vector pCR3 for TA cloning (Invitrogen).

Similarly, a partial fragment of the mouse Fuc-TIX cDNA was amplified using other primer sets whose nucleotide sequences are shown in SEQ ID NOS:20 and 21, and then subcloned into pCR3.

After checking the directions of the amplified fragments in the plasmids, these plasmids were excised with HindIII. Next using digoxigenin-labled mix (Boehringer Manheim), in vitro transcription was conducted with SP6 RNA polymerase to make digoxigenin-labeled antisense or sense riboprobe. Whether a riboprobe is an antisense or sense riboprobe depends on the direction of the inserted fragment. Further, digoxigenin-labeled antisense or sense probe was made by in vitro transcription with T7 RNA polymerase in the same manner as described above, after excising these plasmids with XhoI. Again, whether a riboprobe is an antisense or sense riboprobe depends on the direction of the inserted fragment.

The brain tissue of an adult BALB/c mouse was treated in 4% paraformaldehyde overnight to immobilize, then embedded in paraffin.

The brain tissue embedded in the paraffin was dissected into sections. Then the paraffin was removed from the sections, and the sections were hydrated.

The sections of the brain tissue were treated with 0.2 M hydrochloric acid for 20 minutes so as to inactivate alkaline phosphatase, which had originally been present in the tissue. Subsequently 4 µg/ml of protease K (Boehringer Mannheim) was added to the sections, and the mixture was allowed to react for 15 minutes at 37° C.

Next the sections were treated in 4% paraformaldehyde/PBS (w/v) for 10 minutes for immobilization, and immersed in 0.2% glycine/PBS (w/v) for 10 minutes to avoid non-specific staining.

After dehydrating the sections, the riboprobes were hybridized on the sections in a hybridization solution [50% formaldehyde, 10% dextran sulfate, 1× Denhardt's solution, 10 mM Tris-HCl (pH 7.5), 1 mM EDTA, 0.6 M NaCl, 200 µg/ml yeast tRNA] for 16 hours at 50° C.

The sections were washed twice with 2×SSC for 15 minutes at room temperature, then washed with 0.1×SSC for 30 minutes at 50° C.

Signals showing the hybridization with the probes were detected using anti-digoxigenin antibodies and NBT/BCIP solution (Boehringer Mannheim).

FIG. 6 shows an example of the results.

When anti-sense probes were used, staining of neuron cell bodies of the neurons in hippocampus were observed, that is, expression of Fuc-TIX mRNA was detected, whereas no expression was detected in glial cells.

On the other hand, when sense probes were used as negative control, no stained cells were observed Accordingly, it was suggested that the mouse Fuc-TIX gene was expressed in cell bodies of the neurons, but not in the glial cells.

Example 6

Cloning of Human Fuc-TIX Chromosomal DNA

Human Fuc-TIX chromosomal DNA corresponding to mouse Fuc-TIX cDNA was cloned.

First, clones containing human Fuc-TIX chromosomal DNA were obtained by screening a human chromosomal DNA library (PAC library) with PCR using primers, specific to the mouse Fuc-TIX gene, whose nucleotide sequences are shown in SEQ ID NOS: 22 and 23.

Each of 405,504 clones derived from the PAC library was cultured, one clone per well, in 1,056 384-well plates (16 wells long, 24 wells wide). Next the 1,056 plates were piled: 12 plates long (X axis: 1 to 12), 8 plates wide (Y axis: A to H), and 11 plates high (Z axis: 1 to 11). Finally 88 pools were prepared by mixing all clones in each row of 12 plates in the X axis per (Z, Y) coordinates.

In addition, 132 pools were separately prepared by mixing all clones in each row of 8 plates in the direction of the Y axis per (Z, X) coordinates.

PCR was performed for the 88 pools using the above primers so as to find out which pools of the (Z, Y) coordinates used as templates resulted in the amplification of human Fuc-TIX gene fragments. As a result, clones containing the human Fuc-TIX gene were confirmed to be present in a pool of the (Z, Y) coordinates: (8, H).

Similarly, PCR was performed for 12 pools of the specified Z axis 8 containing coordinates (8, 1–12), which were selected from the above 132 pools. Thus clones containing the human Fuc-TIX gene were found to exist in a pool of the (Z, X) coordinates: (8, 12).

These results revealed that clones containing the human Fuc-TIX gene were present in a pool the (Z, Y, X) coordinates: (8, H, 12).

Each of 384 clones present on the plate of the specified coordinates (8, H, 12) was picked simultaneously with a needle point holder for 384-well (16 wells long, 24 wells wide) plate. Then the clones were inoculated both in a vertical slot plate consisting of 24 vertical slots (each of vertical 16 wells of a 384 well plate are connected, forming 24 vertical slots) and in a horizontal slot plate consisting of 16 horizontal slots (each of horizontal 24 wells of a 384 well plate are connected, forming 16 horizontal slots), both containing 2×TY media; and cultured overnight.

Similarly, PCR was performed using 1 µl of culture fluid derived from each of the 40 types of slots as a template. Next the coordinates of an intersection of vertical and horizontal slots showing the amplification of human Fuc-TIX gene fragments were determined to specify the coordinates on which clones containing human Fuc-TIX genes were present.

A plasmid DNA was isolated from the clones of the specified coordinates, excised with HindIII or EcoRI, then subjected to Southern hybridization using a mouse Fuc-TIX cDNA fragment as a probe. How to prepare the probe is as described below.

PCR was performed using the mouse Fuc-TIX cDNA as a template and primers shown in SEQ ID NOS: 24 and 25, thereby amplifying mouse Fuc-TIX cDNA fragments.

Subsequently, the fragment was labeled with $^{32}P$ using a multi prime DNA labeling system (Amersham) to make a probe.

As a result of Southern hybridization, an approximately 2.7-kb HindIII fragment and an approximately 1.5-kb EcoRI fragment hybridized to the mouse Fuc-TIX cDNA.

Based on the result of hybridization, it was deduced that these fragments had been derived from the human Fuc-TIX chromosome DNA. About the 2.7-kb Hind III fragment was subcloned into HindIII site of a vector pBluescript SK (−) to construct pBS-hgFT9H.

Further, about the 1.5-kb EcoRI fragment was subcloned into EcoRI site of a vector pBluesript SK (−), thereby constructing pBS-hgFT9E.

The nucleotide sequence of the human Fuc-TIX chromosomal DNA (2,822 bp) was determined by assembling the nucleotide sequences of pBS-hgFT9H and pBS-hgFT9E, which were determined in the same way as in Example 1. The obtained nucleotide sequence was shown in SEQ ID NO:4.

The human Fuc-TIX chromosome DNA possessed an ORF encoding a polypeptide consisting of 359 amino acids. This amino acid sequence showed 99.2% homology to that of mouse Fuc-TIX (as shown in SEQ ID NO:2): that is, 356 out of 359 amino acids were identical to each other. Therefore, it was concluded that a region of $1289^{th}$ to $2368^{th}$ in SEQ ID NO:4 was a nucleotide sequence encoding human Fuc-TIX with no intron.

The amino acid sequence of human Fuc-TIX is shown in SEQ ID NO:2.

Example 7

Cloning of Human Fuc-TIX cDNA cDNA was synthesized from Poly $(A)^+$ RNA of human gastric mucosa using a cDNA synthesis system (manufactured by GIBCO BRL). An EcoRI-NotI-SalI adaptor (SuperScript Choice System for cDNA Synthesis; manufactured by GIBCO BRL) was added to the both ends. Next the product was inserted into EcoRI site of a cloning vector λZAP II (λZAP II/EcoRI/CIAP Cloning Kit, manufactured by STRATAGENE), followed by in vitro packaging with a Gigapack III Gold Packaging Extract (manufactured by Stratagene) to construct a cDNA library.

PCR was performed using the PAC clone containing the human Fuc-TIX chromosome DNA obtained in Example 6 as a template and primers shown in SEQ ID NOS:26 and 27, thereby amplifying human Fuc-TIX chromosome DNA fragments.

The fragments were labeled with $^{32}$P using a multi prime DNA labeling system (Amersham) to make a probe.

Using the probe, plaque hybridization was performed for $5 \times 10^5$ clones of the cDNA library constructed as described above.

In this hybridization, filters were washed twice in a buffer containing SSPE at a 2-fold concentration [SSPE at a 1-fold concentration contained 180 mM sodium chloride, 10 mM sodium dihydrogenphosphate, 1 mM ethylenediaminetetraacetic acid (EDTA), pH 7.4] and 0.1% SDS at 65° C. by immersing in this buffer for 10 minutes, washed once in a buffer containing SSPE at a 1-fold concentration and 0.1% SDS at 65° C. by immersing in this buffer for 15 minutes, and washed twice in a buffer containing 0.2×SSPE and 0.1% SDS at 65° C. by immersing in this buffer for 10 minutes.

As a result of the plaque hybridization, four independent clones capable of hybridizing to the probe were obtained. Plasmids were obtained from each of the clones by in vivo excision according to Stratagene's manual, and subjected to analysis with restriction enzymes and determination of the nucleotide sequences.

Determination of the sequences revealed that one of the obtained plasmids, pBS-hFT9 (S2) contained about a 2.7-kb cDNA shown in SEQ ID NO:5.

The cDNA encoded a polypeptide having the same amino acid sequence (shown in SEQ ID NO:2) as that of the polypeptide encoded by human Fuc-TIX chromosome.

The *Escherichia coli* SOLR™ Strain/pBS-hFT9 (S2) containing pBS-hFT9 (S2) was deposited with National Institute of Bioscience and Human Technology, Agency of Industrial Science and Technology (1–3, Higashi 1-chome, Tsukuba-shi, Ibaraki-ken, Japan) on Jul. 10, 1998; and the assigned accession number was FERM BP-6416.

FIG. 7 shows the structure of pBS-hFT9 (S2).

Example 8

Generation of Fuc-TIX Gene Knockout Mouse (1) Isolation of Mouse Fuc-TIX Gene

λFIXII/129 genomic library (manufactured by Stratagene) was screened by plaque hybridization using the probe used in Example 4 (1). Thus about $6 \times 10^4$ clones were screened to detect four positive clones.

After the second and the third screening, respective single clones were obtained. Then PCR was performed using a primer (CB-55) having the nucleotide sequence represented by SEQ ID NO:12 and a primer (CB-56) having the nucleotide sequence represented by SEQ ID NO:13, both specific to mouse Fuc-TIX gene, followed by analysis with cleavage by restriction enzymes. Thus it was confirmed that the four clones were all identical to each other and each contained the whole coding region and the whole 3' un-translated region of the Fuc-TIX cDNA. This phage clone is called λMFT9-31.

λMFT9-31 DNA was digested with SalI to prepare chromosomal DNA containing the Fuc-TIX gene. The chromosomal DNA was subcloned into SalI site of pBluescript SK–, thereby constructing a plasmid pFut9WT-129.

The chromosomal DNA containing the Fuc-TIX gene was about 20 kb in length. The nucleotide sequence of the chromosomal DNA was determined. The chromosomal DNA contained part of intron 2 of the mouse Fuc-TIX gene (about 4-kb), exon 3 of the mouse Fuc-TIX gene (consisting of 8-bp 5' non-translation region, the whole coding region, and the whole 3' untranslated region), and about 14-kb chromosome region following the exon 3. The structure of the chromosomal DNA in the plasmid pFut9WT-129 is shown in FIG. 8. Further, the clone contained almost no 5' untranslated region region.

The following experiments were conducted to obtain 5' untranslated region of the gene.

A DNA fragment containing 5' untranslated region of mouse Fuc-TIX cDNA was obtained using 5' RACE method. λFIXII/129 genomic library was screened using the DNA as a probe to obtain two independent positive clones (hereinafter referred to as λMFT9-11 and λMFT9-25).

Chromosomal DNAs containing Fuc-TIX gene were excised from DNAs derived from λMFT9-11 and λMFT9-25 by digestion with SalI, and were subcloned respectively into SalI site of pBluescript SK(–). The chromosomal DNAs contained in λMFT9-11 and λMFT9-25 were about 12 kb and about 16 kb in length, respectively. As a result of determination of the nucleotide sequences, it was shown that λMFT9-11 and λMFT9-25 contained exon 1 and exon 2, respectively.

These results revealed that the mouse Fuc-TIX gene consisted of three exons. The sequences of exon/intron boundary sites followed the GT-AG rule. The upstream region of exon 1 was thought to contain a promoter region of the mouse Fuc-TIX gene. The sequences of exons 1 to 3, and the nucleotide sequence of the region upstream of exon 1 expected to contain the promoter region, are shown in SEQ ID NOS:28 to 31, respectively. The structure of the mouse Fuc-TIX gene is shown in FIG. 9.

The chromosomal localization of the mouse Fuc-TIX gene (which was shown as Fut 9 in FIG. 10) was examined by PCR using interspecific backcross DNA panel as a template according to a conventional method (Mamm. Genome, 5, 253, 1994).

DNA having a nucleotide sequence represented by SEQ ID NO: 13 (CB-56) and DNA having a nucleotide sequence represented by SEQ ID NO:32 (CB-197) were used as primers (See FIG. 8). CB-197 is a primer set in intron 2.

PCR reaction was performed by 35 cycles, each consisting of 1 minute at 94° C., 1 minute at 64° C., and 3 minutes at 72° C.; using 50 µl of a reaction solution panel [10 mM Tris-HCl (pH 8.3), 50 mM KCl, 1.5 mM MgCl$_2$, 0.2 mM dNTP, 0.001% (w/v) gelatin, 0.2 µM gene specific primers, 1 µl of DNA polymerase AmpliTaq Gold™ (Perkin Elmer)] containing chromosomal DNA (10 ng) of interspecific backcross DNA.

As a result of this PCR, it was shown that the mouse Fuc-TIX gene was located on the chromosome 4 (FIG. 10) and present neighboring to marker genes (Aop2-rs2, D4Ertd519e, D4Ertd582e). Moreover, the mouse Fuc-TIX gene was located 1.1±1.1 cM distal to D4Mitl49 than the marker gene D4Ertd389e and 4.25±2.1 cM proximal to D4Abble.

(2) Construction of a Targeting Vector for Homologous Recombination

The 3' half of the coding region and the whole 3' untranslated region of the mouse Fuc-TIX gene were replaced by a neomycin-resistant gene to make a targeting vector pFut9F

[tkneo] for generating a knockout mouse lacking the mouse Fuc-TIX gene as described below (FIGS. 8 and 11).

The chromosomal DNA containing the Fuc-TIX gene, which was inserted in the plasmid pFut9WT-129, was separated to three fragments (B1, B2, and B3), and each fragment was subcloned.

A BamHI fragment (about 1.8 kb) was prepared by digestion of the plasmid pFut9WT-129 with BamHI. The fragment was inserted into BamHI site of pBluescript SK(−) to construct a plasmid pB1.

A BamHI fragment (about 6.0 kb) was prepared by digestion of the plasmid pFut9WT-129 was excised with BamHI. The fragment was inserted into BamHI site of pBluescript SK(−) to construct a plasmid pB2.

A BamHI fragment (15 kb) was prepared by digestion of the plasmid pFut9 wt-129 with BamHI. The ends of this fragment were joined to form a ring, constructing a plasmid pB3.

Using the resulting pB2, the 3' half of the coding region and the whole 3' untranslated region of the mouse Fuc-TIX gene were replaced by a neomycin-resistant gene to construct a plasmid pB2-Neo.

The plasmid pB2 was cleaved with XhoI, thereby obtaining a 9.0-kb XhoI fragment. The DNA fragment was treated with DNA polymerase Klenow fragment for blunting the XhoI-cleaved ends, followed by self-ligation to construct a plasmid pB2 lacking XhoI cleavage site.

The plasmid was partially digested with SacI, thereby obtaining SacI fragment (about 6.0-kb). The DNA fragment was treated with DNA polymerase Klenow fragment for blunting the SacI-cleaved ends, and self-ligated after addition of XhoI linkers to construct pB2-XhoI.

pB2-XhoI was excised with XhoI, thereby obtaining a 6.1-kb XhoI fragment. In addition, pMC1NeopolyA (manufactured by Stratagene) was excised with XhoI and SalI, obtaining a 1.2-kb XhoI—SalI fragment containing a neomycin-resistant gene. The 6.1-kb XhoI fragment derived from pB2-XhoI and the 1.2-kb XhoI—SalI fragment derived from pMC1NeopolyA were ligated to construct a plasmid pB2-Neo.

Moreover, a thymidine kinase gene, which is a marker for negative selection, was ligated to the 3' terminal of the B3 fragment in pB3 to construct a plasmid pBS as described below.

pB3 was cleaved with XhoI, thereby obtaining a 15-kb XhoI fragment. In addition, a plasmid MC-1-TK (Nature, 336, 348, 1988) was cleaved with XhoI and SalI to prepare a 1.8-kb XhoI—SalI fragment containing a thymidine kinase gene. The 15-kb XhoI fragment derived from pB3 and the 1.8-kb XhoI—SalI fragment derived from MC-1-TK were ligated to make a plasmid pB3-tk.

pB2-Neo and pB3-tk, both constructed as described above, were excised with BamHI, obtaining a 4.0-kb BamHI fragment and a 17-kb BamHI fragment, respectively. The 4.0-kb BamHI fragment derived from pB2-Neo and the 17-kb BamHI fragment derived from pB3-tk were ligated to construct a plasmid pFut9F[tkneo].

(3) Preparation of Homologously Recombined Embryonic Stem Cell (ES Cell) Clones

The plasmid pFut9F[tkneo] constructed in (2) above was cleaved with NotI. The resulting DNA fragment (25 µg) was mixed with 0.8 ml of ES cells that had been prepared with PBS to $2.5 \times 10^7$ cells/ml.

The NotI-cleaved DNA fragment was introduced into ES cells by electroporation using a Gene Pulser (manufactured by BioRad) under conditions of 0.35 kV and 950 µF.

The ES cells were inoculated $1 \times 10^7$ cells per 10 cm culture dish on which feeder cells had previously been inoculated. Then the cells were cultured in 15% FBS-DMEM media containing $10^3$ units/ml of ESGRO (manufactured by GIBCO), 100 mM β-mercaptoethanol, 100 units/ml of penicillin (manufactured by GIBCO), and 100 µg/ml of streptomycin (manufactured by GIBCO). From day 2,200 µg/ml of G418 (manufactured by GIBCO) and 2 µM Gancyclovir (manufactured by Syntex) were added to the media, followed by selection of cells with introduced genes.

Colonies appeared 8 to 10 days after starting the selection were isolated. A total of 144 types of ES cell clones were isolated. Next, chromosomal DNAs were isolated from 39 types of the ES cells according to a conventional method, and then cells containing the targeting vectors integrated by homologous recombination were selected by PCR.

Chromosomal DNAs were isolated as described below.

The cells cultured in a 24-well plate were lysed by adding 500 µl of a lysis buffer [10 mM Tris-HCl (pH 7.8), 1 mM EDTA, 0.1 M NaCl, 0.1% SDS], followed by phenol extraction and ethanol precipitation to isolate chromosomal DNAs.

PCR was performed using DNA (CB-197) having a nucleotide sequence shown in SEQ ID NO:32 that had been set in the region upstream of the mouse Fuc-TIX gene inserted in the targeting vector, and DNA (CB-199) having a nucleotide sequence shown in SEQ ID NO:33 that had been set in neomycin-resistant gene as primers (See FIG. 8).

PCR was performed under the following conditions.

That is, PCR was performed by 30 cycles, each consisting of heating at 94° C. for 1 minute, at 98° C. for 20 seconds, at 68° C. for 8 minutes; using 50 µl of a reaction solution [1×LA PCR™ buffer II ($Mg^{2+}$ free), 2.5 mM $MgCl_2$, dNTPs (0.4 mM each), the above primer (0.2 µM each), 2 units of Takara LA Taq™] containing the chromosomal DNA isolated from the ES cells.

As for ES cells in which the latter half of the exon 3 of the mouse Fuc-TIX gene is disrupted by homologous recombination of the mouse Fuc-TIX gene and the targeting vector, about a DNA fragment (about 3 kb) would be amplified. Analysis of the 39 types of the ES cell clones confirmed the amplification of the about 3-kb DNA fragment in 3 types of the ES cell clones. Therefore, it was concluded that in these 3 types of the ES cell clones, the mouse Fuc-TIX gene was disrupted as expected.

(4) Generation of Knockout Mouse Lacking the Mouse Fuc-TIX Gene

The uterus was excised from C57BL/6 mice (4 weeks old female) on day 3.5 after crossing, followed by collection of blastocysts. The 3 types of the ES cells having the disrupted mouse Fuc-TIX gene were introduced respectively into the blastocysts (about 15 ES cells per blastocyst) using a micromanipulator. Subsequently the blastocysts were transplanted, to the both sides of the uterus (10 blastocysts per side) of surrogate mice (ICR) in which false pregnancy had been induced.

Consequently, 95 progeny were obtained, 44 of which (31 male mice, 13 female mice) were determined to be chimeric mice based on their coat color. Heterozygous mice were obtained by crossing these chimeric mice with normal C57BL/6 mice, followed by crossing these hetero mice with each other, thereby obtaining knockout mice.

Chromosomal DNAs were extracted from tails of the progeny obtained by crossing the heterozygous mice, and subjected to PCR to determine the genetic type.

Long PCR was performed using simultaneously primers CB-197 and CB-199, and DNA (CB-280) having a nucleotide sequence shown in SEQ ID NO:34 (See FIG. 8). As for wild type mice, only an approximately 3.5-kb band that is amplified by CB-197 and CB-280 was detected; as for mice with the deficient Fuc-TIX gene homozygously, only an approximately 3.0-kb band that is amplified by CB-197 and CB-199 was detected; as for heterozygous mice, both of the approximately 3.5-kb band that is amplified by CB-197 and CB-280, and the approximately 3.0-kb band that is amplified by CB-197 and CB-199 were detected.

FIG. 12 shows an example of the result of PCR analysis. The No. 5 mouse was demonstrated to be a mouse with the deficient Fuc-TIX gene (Fuc-TIX gene knockout mouse).

Thirty-four progeny were obtained by crossing the heterozygous mice. The progeny consisted of 11 wild type mice, 17 heterozygous mice, and 6 Fuc-TIX gene knockout mice (4 male and 2 female mice).

The Fuc-TIX gene knockout mice are extremely useful in analysis of physiological and pathological functions of the Fuc-TIX gene.

Example 9

Analysis of Reaction Specificity of Fuc-TIX

Poly-N-acetyllactosamine sugar chain is a sugar chain with the structure having N-acetyllactosamine as repeating unit bound via a β1,3-linkage [(Galβ1-4GlcNAcβ1-3) n;n represents 2 or more], and appears not only in N-glycoside linked and O-glycoside linked sugar chains of glycoproteins, but also in sugar chains of glycolipids and in oligosaccharides.

Using a poly-N-acetyllactosamine sugar chain, it was examined that to which GlcNAc in the sugar chains, human Fuc-TIX and 5 types of human α1,3-fucosyltransferase (Fuc-TIII, Fuc-TIV, Fuc-TV, Fuc-TVI, and Fuc-TVII) that had been cloned so far transferred fucose.

pBS-hFT9(S2) obtained in Example 7 was excised with PstI and HindIII, followed by blunt-ending with DNA polymerase Klenow fragment. After blunt ending, SfiI linkers prepared in Example 1 (2) were added to the product, thereby obtaining a fragment of about 1.6 kb.

The expression vector pAMo was cleaved with SfiI, obtaining an approximately 8.7-kb SfiI fragment.

The fragment of the about 1.6 kb derived from pBS-hFT9 (S2) and the SfiI fragment of about 8.7 kb derived from pAMo were ligated to make pAMo-FT9, an expression plasmid for human Fuc-TIX.

Control plasmid (pAMo) and the human Fuc-TIX expression plasmid pAMo-FT9 were introduced into Namalwa cells according to the method shown in Example 1 (3), thereby obtaining stable transformants.

Namalwa cells expressing each of the other 5 types of human α1,3-fucosyltransferases (Fuc-TIII, Fuc-TIV, Fuc-TV, Fuc-TVI, and Fuc-TVII) were obtained according to the previous report (Glycoconjugate J., 13, 802–812, Biochem. Biophys. Res. Commun., 237, 131–137, 1997).

The resultant transformants (about $1\times10^7$) were collected in microtubes (1.5 ml, manufactured by Eppendolf), followed by centrifugation at 550×g for 7 minutes to collect the cells.

The collected cells were washed with 0.9 ml of PBS. The washed cells were suspended in 100 μl of a solution which consisted of 20 mM HEPES (pH 7.2) and 1% TrironX-100, then allowed to stand at 4° C. for 10 minutes. Subsequently the cells were disrupted using a ultrasonicator (Bioruptor; manufactured by COSMO BIO CO., LTD.)

After disruption of the cells, each supernatant was obtained by centrifugation at 550×g for 7 minutes and used as an enzyme sample.

A poly-N-acetyllactosamine sugar chain (Galβ1-4GlcNAcβ1-3 Galβ1-4GlcNAc β1-3Galβ1-4GlcNAc) consisting of 6 sugars was fluorescently labeled with 2-aminobenzamide to make a sugar chain (Galβ1-4GlcNAcβ1-3Galβ1-4GlcNAcβ1-3Galβ1-4GlcNAc-2AB: abbreviated as S in FIGS. 13 and 15, and table 3), which was used as a substrate Florescent labeling was performed using a Signal™ 2-AB glycan labeling kit (manufactured by Oxford GlycoScience). A poly-N-acetyllactosamine sugar chain (Galβ1-4GlcNAcβ1-3Galβ1-4GlcNAcβ1-3Galβ1-4GlcNAc) was prepared according to WO98/03524.

The activity was measured as follows.

Samples were allowed to react in 20 μl of an assay solution [50 mM cacodylate (pH 6.8), 5 mM ATP, 10 mM L-fucose, 75 μM UDP-Fuc (manufactured by SIGMA), 25 mM MnCl$_2$, 15 μM fluorescently labeled sugar chain substrate, 6 μl of the cell lysate above] at 37° C. for 2 hours, followed by treatment at 100° C. for 3 minutes to stop the reaction. Next 200 μl of water was added to the samples, and the supernatant was obtained by centrifugation at 10,000×g for 5 minutes. Using an aliquot of the supernatant (10 μl), products were analyzed by HPLC under the following conditions.

HPLC:

Column—TSK-gel ODS-80TsQA column (4.6×250 mm; TOSOH CORPORATION)

Eluate—0.02 M ammonium acetate (pH 4.0) containing 7% methanol

Elution temperature—50° C.

Flow rate—1.0 ml/min.

Detection—Fluorescence spectrum photometer FB-920 (manufactured by JASCO Corporation) (excitation wavelength: 330 nm, radiation wavelength: 420 nm)

An example of the result of HPLC analysis is shown in FIG. 13. In FIG. 13 (a), an extract derived from the cells containing control plasmid introduced thereto was used as an enzyme sample; in FIG. 13 (b), an extract derived from the cells expressing Fuc-TIV was used as an enzyme sample; and in FIG. 13 (c), an extract derived from the cells expressing Fuc-TIX was used as an enzyme sample.

It was shown that three types of products (P1, P2 and P3) were produced when the extract derived from the cells expressing Fuc-TIV or Fuc-TIX was used as an enzyme sample.

Fluorescent labeling with 2-aminobenzamide resulted in ring opening of the reduced terminal GlcNAc, so that possible products were the following three types:

Galβ1-4(Fucα1-3)GlcNAcβ1-3Galβ1-4GlcNAcβ1-3Galβ1-4GlcNac-2AB, Galβ1-4GlcNAcβ1-3Galβ1-4(Fucα1-3)GlcNAcβ1-3Galβ1-4GlcNAc-2AB, and Galβ1-4(Fucα1-3)GlcNAcβ1-3Galβ1-4(Fucα1-3)GlcNAcβ1-3Galβ1-4GlcNAc-2AB.

Structure of the products was confirmed in the manner as described below.

Each product (P1, P2 or P3) was collected and dried completely using SpeedVac (manufactured by SAVANT). Subsequently the dried product was dissolved in water, followed by centrifugation to remove insoluble fraction, then subjected to the following analysis.

The molecular weight of each of the products (P1, P2 and P3) were compared by HPLC analyzing under the following conditions.

HPLC:
Column—GlycoSep™ N HPLC column (4.6×250 mm, manufactured by Oxford GlycoScience)
Eluate—0.25 M ammonium formate buffer (pH 4.4) containing 65% acetonitrile
Elution temperature—30° C.
Flow rate—1.0 ml/min.
Detection—Fluorescence spectrum photometer FP-920 (manufactured by JASCO Corporation) (excitation wavelength: 330 nm, radiation wavelength: 420 nm)
Molecular weight marker—glucose homo polymer fluorescnetly labeled with 2-aminobenzamide (manufactured by Oxford GlycoScience)

The results are shown in FIGS. 14 (a) to (c).

P1 and P2 were eluted at the same position (see FIGS. 14 (a) and (b)). Based on the elution time of P3, it was demonstrated that P3 was larger than P1 or P2 by about one glucose (See FIG. 14 (c)).

Accordingly, P1 and P2 were thought to correspond to either Galβ1-4(Fucα1-3)GlcNAcβ1-3Galβ1-4GlcNAcβ1-3Galβ1-4GlcNAc-2AB or Galβ1-4GlcNAcβ1-3Galβ1-4(Fucα1-3)GlcNAcβ1-3Galβ1-4GlcNAc-2AB and P3 to correspond to Galβ1-4(Fucα1-3)GlcNAcβ1-3Galβ1-4(Fucα1-3)GlcNAcβ1-3Galβ1-4GlcNAc-2AB.

Each of the collected products (P1, P2 and P3) was treated in 50 mM sodium citrate buffer (pH 3.5) containing 300 mU/ml of Jack bean β-galactosidase (manufactured by Oxford GlycoScience) at 37° C. for 15 hours. Then the reaction solution was analyzed by HPLC using a GlycoSep™ N HPLC column (4.6×250 mm; manufactured by Oxford GlycoScience) in the same manner as described above.

The results are shown in FIGS. 14 (d) to (f).

The elution positions of the products P1 and P3 were not changed before and after the treatment with Jack bean β-galactosidase (see FIGS. 14 (a) and (d), or (c) and (f)). However, the product P2 showed a decrease in molecular weight by about one glucose after treatment with Jack bean β-galactosidase (see FIGS. 14 (b) and (e)). These results suggested that the structure of the product P2 was Galβ1-4GlcNAcβ1-3Galβ1-4(Fucα1-3)GlcNAcβ1-3Galβ1-4GlcNAc-2AB. Therefore, it was concluded that the structure of the product P1 was Galβ1-4(Fucα1-3) GlcNAcβ1-3Galβ1-4GlcNAcβ1-3Galβ1-4GlcNAc-2AB.

Various types of glycosidase were used to confirm the structure configurations of the products in detail.

Each of the collected products (P1, P2 and P3) was treated in 50 mM sodium citrate buffer (pH 5.0) containing 0.2 mU/ml of almond meal α1,3/4-fucosidase (manufactured by Oxford GlycoScience) at 37° C. for 15 hours. Then the reaction solution was analyzed by HPLC using a TSK-gel ODS-80Ts QA column (4.6×250 mm; TOSOH CORPORATION) in the same manner as described above (FIG. 15).

As a result, the elution position of the product P1 changed before and after treatment with almond meal α1,3/4-fucosidase (see FIGS. 15 (a) and (b)), and the elution position after treatment with the enzyme was same as that of the substrate (see FIGS. 15 (b) and (c)).

The elution position of the product P2 remained unchanged before and after treatment with almond meal α1,3/4-fucosidase (see FIGS. 15 (d) and (e)).

The elution position of the product P3 changed before and after treatment with almond meal α1,3/4-fucosidase (see FIGS. 15 (j) and (k)), and the elution position after treatment with the enzyme was same as that of the product P2 (see FIGS. 15 (k) and (d)).

These results indicated that the structure of the products P1, P2 and P3 were Galβ1-4(Fucα1-3)GlcNAcβ1-3Galβ1-4GlcNAcβ1-3Galβ1-4GlcNAc-2AB, Galβ1-4GlcNAcβ1-3Galβ1-4(Fucα1-3) GlcNAcβ1-3Galβ1-4GlcNAc-2AB, and Galβ1-4(Fucα1-3)GlcNAcβ1-3Galβ1-4(Fucα1-3)GlcNAcβ1-3Galβ1-4GlcNAc-2AB, respectively.

To further confirm the structure of the product P2, the product P2 was treated in order with Jack bean β-galactosidase, Jack bean β-N-acetylhexosaminidase, and almond meal α1,3/4-fucosidase. Then the reaction solution was analyzed by HPLC using a TSK-gel ODS-80TsQA column (4.6×250 mm, TOSOH CORPORATION) under the same conditions as described above.

The product P2 was treated in 50 mM sodium citrate buffer (pH 5.0) containing 600 mU/ml of Jack bean β-galactosidase (manufactured by Oxford GlycoScience) at 37° C. for 15 hours, followed by treatment at 100° C. for 5 minutes to stop the reaction.

Ten U/ml of Jack bean β-N-acetylhexosaminidase (manufactured by Oxford GlycoScience) was added to an aliquot of the resulting reaction solution, and allowed to react at 37° C. for 15 hours, followed by treatment at 100° C. for 5 minutes to stop the reaction.

Moreover 0.2 mU/ml of almond meal α1,3/4-fucosidase (manufactured by Oxford GlycoScience) was added to the resultant reaction solution, and allowed to react at 37° C. for 15 hours, followed by treatment at 100° C. for 5 minutes to stop the reaction.

FIG. 15 (f) shows the HPLC pattern obtained when the product P2 was treated only with Jack bean β-galactosidase; FIG. 15 (g) shows the HPLC pattern when the product P2 was treated in order with Jack bean β-galactosidase and Jack bean β-N-acetylhexosaminidase; and FIG. 15 (h) shows the HPLC pattern when the product P2 was treated in order with Jack bean β-galactosidase, Jack bean β-N-acetylhexosaminidase, and almond meal α1,3/4-fucosidase.

The elution position of the product P2 treated in order with Jack bean β-galactosidase, Jack bean β-N-acetylhexosaminidase, and almond meal α1,3/4-fucosidase (See FIG. 15 (h)) was the same as that of a sugar chain (Galβ1-4GlcNAcβ1-3Galβ1-4GlcNAc-2AB), which was prepared from a poly-N-acetyllactosamine sugar chain consisting of 4 sugars (Galβ1-4GlcNAcβ1-3Galβ1-4GlcNAc) by fluorescent labeling with 2-aminobenzamide (see FIG. 15 (i)).

Therefore, it was confirmed that the structure of the product P2 was Galβ1-4GlcNAcβ1-3Galβ1-4(Fucα1-3)GlcNAcβ1-3Galβ1-4GlcNAc-2AB.

The poly-N-acetyllactosamine sugar chain consisting of 4 sugars was prepared by fluorescent labaling using Signal™ 2-AB glycan labelling kit (manufactured by Oxford GlycoScience) according to WO98/03524.

After treatment with almond meal α1,3/4-fucosidase, the product P3 was treated in order with Jack bean β-galactosidase, Jack bean β-N-acetylhexosaminidase and almond meal α1,3/4-fucosidase under the same conditions as that employed for the product P2. Therefore, it was confirmed that the structure of P3 was Galβ1-4(Fucα1-3)GlcNAcβ1-3Galβ1-4(Fucα1-3)GlcNAcβ1-3Galβ1-4GlcNAc-2AB.

The enzyme reaction was performed using the poly-N-acetyllactosamine sugar chain (S) as a substrate. When an extract derived from Namalwa cells expressing Fuc-TIV was used as an enzyme, the major product was P2 (the VIM-2 sugar chain) (see FIG. 13 (b) and Table 2); and when an extract derived from Namalwa cells expressing Fuc-TIX was used as an enzyme, the major product was P1 (the Le$^x$ sugar chain) (see FIG. 13 (c) and Table 2).

Similar analysis revealed that when an extract derived from Namalwa cells expressing Fuc-TIII, Fuc-TV, or Fuc-TVI was used as an enzyme, the major product was P2 (VIM 2 sugar chain) (Table 2). The use of an extract derived from Namalwa cells expressing Fuc-TVII as an enzyme resulted in no product (Table 2).

TABLE 2

Enzyme activity for a Poly-N-acetyllactosamine sugar chain

| | Production (%) | | |
|---|---|---|---|
| Enzyme | P1 | P2 | P3 |
| Fuc-TIII | 2.0 | 98.0 | 0.0 |
| Fuc-TIV | 22.2 | 72.0 | 5.8 |
| Fuc-TV | 7.5 | 92.5 | 0.0 |
| Fuc-TVI | 8.3 | 88.7 | 3.0 |
| Fuc-TVII | 0.0 | 0.0 | 0.0 |
| Fuc-TIX | 82.7 | 13.4 | 3.9 |

The production of each of the products is shown as a relative value when total amount of products (P1, P2 and P3) produced by each enzyme is assumed to be 100%.

These results demonstrated that Fuc-TIII, Fuc-TIV, Fuc-TV, and Fuc-TVI fucosylated the inner GlcNAc residue in the poly-N-acetyllactosamine sugar chain, and had strong activity to synthesize VIM-2 sugar chain synthesis; whereas Fuc-TIX fucosylated to the distal GlcNAc residue, and had strong activity to synthesize the Le$^x$ sugar chain. Fuc-TIX was shown to be α1,3-fucosyltransferase having activity clearly different from that of other an α1,3-fucosyltransferase. Furthermore, it was found that the Le$^x$ sugar chain can be efficiently synthesized on the terminal of the poly-N-acetyllactosamine sugar chain using Fuc-TIX.

The enzymatic activities of Fuc-TIV, Fuc-TVI and Fuc-TIX were measured using the product P1 or P2 as a substrate in addition to the above substrate (S).

Table 3 shows the results.

Fuc-TIV and Fuc-TVI synthesized the product P3 using the product P1 as a good substrate, while Fuc-TIX synthesized the product P3 using the product P2 as a good substrate.

Therefore, it was concluded that the product P3 (the dimeric Le$^x$ sugar chain) was efficiently produced by cooperation of Fuc-TIX and the other α1,3-fucosyltransferases (for example, Fuc-TIV or Fuc-TVI).

TABLE 3

Enzymatic activity for the Poly-N-acetyllactosamine sugar chain and the Monofucosylpoly-N-acetyllactosamine sugar chains

| Substrate | Product | Fuc-TIV | Fuc-TVI | Fuc-TIX |
|---|---|---|---|---|
| S | P1 | 1.6 | 2.3 | 7.2 |
| S | P2 | 4.1 | 16.4 | 1.6 |
| S | P3 | 0.5 | 0.8 | 0.7 |
| P1 | P3 | 2.8 | 7.6 | 1.0 |
| P2 | P3 | 1.0 | 1.0 | 5.0 |

Enzymatic activities of Fuc-TIV and of Fuc-TVI are shown as relative activities with the activity for P2 assumed to be 1. Enzymatic activity of Fuc-TIX is shown as relative activity with the activity for P1 assumed to be 1.

Example 10

Synthesis of the VIM-2 Sugar Chain in Human Culture Cells Transfected with a Human Fuc-TIX Expression Plasmid Using an anti-VIM-2 sugar chain antibody (anti-CDw65 antibody, manufactured by Serotec) and anti-Le$^x$ sugar chain antibodies [73-30 (manufactured by SEIKAGAKU CORPORATION) and anti-CD15 anibody (C3D-1, manufactured by Dako)], indirect fluorescent antibody staining was performed for Namalwa cells expressing human Fuc-TIV or human Fuc-TIX, and for Namalwa cells transfected with the control vector pAMo, which were constructed in Example 9. The VIM-2 sugar chain is a sugar chain having the structure consisting of Galβ1-4GlcNAcβ1-3Galβ1-4(Fucα1-3)GlcNAc on non-reduced terminal of a sugar chain.

Indirect fluorescent antibody staining was performed according to the method described in Example 1 (3). Anti-VIM-2 sugar chain antibodies, 73-30 and C3D-1 were used after dilution at 1:50, 1:100, and 1:50.

FIG. 16 shows the results.

Namalwa cells expressing Fuc-TIV showed a significant increase in reactivity against the anti-VIM-2 sugar chain antibody compared to Namalwa cells transfected with pAMo, whereas Namalwa cells expressing Fuc-TIX showed a slight increase in reactivity against the antibody. In contrast, reactivity against the anti-Le$^x$ sugar chain antibodies [73-30 and anti-CD15 antibody] was greater for Namalwa cells expressing Fuc-TIX than those expressing Fuc-TIV.

These results demonstrated that Fuc-TIV had possessed strong activity for synthesizing VIM-2 sugar chain in the transformed cells. Further, Fuc-TIX was found to have strong activity for synthesizing Le$^x$ sugar chain, but weak activity for VIM-2 sugar chain synthesis in the transformed cells. These results are well consistent with the data of in vitro activity in Example 9.

It was shown that reaction specificity of Fuc-TIV and Fuc-TIX in the cells were also different from each other evidently.

INDUSTRIAL APPLICABILITY

This invention relates to a novel polypeptide having an α1,3-fucosyltransferase activity with a novel substrate specificity, that is characterized by the activity to synthesize the Lewis x sugar chains and Lewis y sugar chains, but not the sialyl Lewis x sugar chains; a method for producing the polypeptide; a DNA encoding the polypeptide; a method for producing the DNA; a recombinant vector obtained by inserting the DNA thereto; a transformant having the recombinant vector; an antibody recognizing the polypeptide; a method for determining or immunostaining the polypeptide of the present invention using the antibody; a method for producing a fucose-containing sugar chain using the polypeptide; a method for producing a fucose-containing sugar chain using the transformant containing the recombinant vector; a method for screening a substance that changes the expression of a gene encoding the polypeptide; a method for screening a substance that changes the activity of the polypeptide; a method for diagnosing diseases, such as encephalopathy, renal diseases, cancers, and so on using the DNA or the antibody; and a therapy for diseases, such as encephalopathy, renal diseases, cancers, and so on using the DNA, a substance that changes the expression of a gene encoding, the polypeptide, or a substance that changes the activity of the polypeptide.

Sequence Listing Free Text

SEQ ID NO:6—explanation of artificial sequence: synthetic DNA
SEQ ID NO:7—explanation of artificial sequence: synthetic DNA
SEQ ID NO:8—explanation of artificial sequence: synthetic DNA
SEQ ID NO:9—explanation of artificial sequence: synthetic DNA
SEQ ID NO:10—explanation of artificial sequence: synthetic DNA
SEQ ID NO:11—explanation of artificial sequence: synthetic DNA
SEQ ID NO:12—explanation of artificial sequence: synthetic DNA
SEQ ID NO:13—explanation of artificial sequence: synthetic DNA
SEQ ID NO:14—explanation of artificial sequence: synthetic DNA
SEQ ID NO:15—explanation of artificial sequence: synthetic DNA
SEQ ID NO:16—explanation of artificial sequence: synthetic DNA
SEQ ID NO:17—explanation of artificial sequence: synthetic DNA
SEQ ID NO:18—explanation of artificial sequence: synthetic DNA
SEQ ID NO:19—explanation of artificial sequence: synthetic DNA
SEQ ID NO:20—explanation of artificial sequence: synthetic DNA
SEQ ID NO:21—explanation of artificial sequence: synthetic DNA
SEQ ID NO:22—explanation of artificial sequence: synthetic DNA
SEQ ID NO:23—explanation of artificial sequence: synthetic DNA
SEQ ID NO:24—explanation of artificial sequence: synthetic DNA
SEQ ID NO:25—explanation of artificial sequence: synthetic DNA
SEQ ID NO:26—explanation of artificial sequence: synthetic DNA
SEQ ID NO:27—explanation of artificial sequence: synthetic DNA
SEQ ID NO:32—explanation of artificial sequence: synthetic DNA
SEQ ID NO:33—explanation of artificial sequence: synthetic DNA
SEQ ID NO:34—explanation of artificial sequence: synthetic DNA All of publications, patents, and patent applications cited in this specification are all incorporated as references into this specification in their entirety.

What is claimed is:

1. A polypeptide selected from the group consisting of the following (a) and (b):
   (a) a polypeptide comprising the amino acid sequence SEQ ID NO:1 or 2, and
   (b) a polypeptide comprising the amino acid residues 56 to 359 of SEQ ID NO:1 or 2,
   wherein said polypeptide has an activity to transfer fucose to an N-acetylglucosamine residue in an N-acetyllactosamine (Galβ1-4GlcNAc) structure existing in a nonreducing terminus of a sugar chain via an α1,3-linkage, but not an activity to transfer fucose to an α2,3-sialyl N-acetyllactosamine (NeuAcα2-3Galβ1-4GlcNAc) structure existing in a nonreducing terminus of a sugar chain via an α1,3-linkage.

2. The polypeptide according to claim 1, wherein the activity of transferring fucose to an N-acetylglucosamine residue in the Galβ1-4GlcNAc structure existing in a nonreducing terminus of a sugar chain via an α1,3-linkage is the Lewis x sugar chain [Galβ1-4(Fucα1-3)GlcNAc] and the Lewis y sugar chain [Fuc α1-2Galβ1-4(Fucα1-3)GlcNAc] synthesizing activity, and the activity of transferring fucose to an N-acetylglucosamine residue in the NeuAcα2-3Galβ1-4GlcNAc structure existing in a nonreducing terminus of a sugar chain via an α1,3-linkage is the sialyl Lewis x sugar chain [NeuAcα2-3Galβ1-4(Fucα1-3)GlcNAc] synthesizing activity.

3. A DNA selected from the following (a), (b), (c), (d), (e), (f), (g) and (h):
   (a) a DNA encoding the polypeptide according to claim 1 or 2,
   (b) a DNA having nucleotides 280 to 1194 of SEQ ID NO: 3,
   (c) a DNA having nucleotides 115 to 1194 of SEQ ID NO: 3,
   (d) a DNA having nucleotides 1454 to 2368 of SEQ ID NO: 4,
   (e) a DNA having nucleotides 1289 to 2368 of SEQ ID NO: 4,
   (f) a DNA having nucleotides 460 to 1374 of SEQ ID NO: 5,
   (g) a DNA having nucleotides 295 to 1374 of SEQ ID NO: 5,
   (h) a full length complement of a DNA hybridizing with DNA selected from a), (b), (c), (d), (e), (f) and (g) using a filter with colony- or plaque-derived DNA immobilized thereon at 65° C. in the presence of 0.7–1.0 M of NaCl, followed by washing the filter at 65° C. with 0.1 standard concentration of SSC (saline-sodium citrate) solution (one standard concentration of SSC solution consists of 150 mM sodium chloride and 15 mM sodium citrate), wherein all of said DNA encode a polypeptide having an activity to transfer fucose to an N-acetylglucosamine residue in an N-acetyllactosamine (Galβ1-4GlcNAc) structure existing in a nonreducing terminus of a sugar chain via an α1,3-linkage, but not having an activity to transfer fucose to an α2,3-sialyl N-acetyllactosamine (NeuAcα2-3Galβ1-4GlcNAc) structure existing in a nonreducing terminus of a sugar chain via an α1,3-linkage.

4. A recombinant DNA obtained by integrating the DNA according to claim 3 into a vector.

5. The recombinant DNA according to claim 4 wherein the recombinant DNA is plasmid pBS-hFT9 (S2).

6. A transformant having the recombinant DNA according to claim 4 or 5, wherein the transformant is selected from the group consisting of microorganisms, animal cells, and insect cells.

7. The transformant according to claim 6, wherein the transformant is a microorganism belonging to *Escherichia*.

8. The transformant according to claim 6, wherein the transformant is an animal cell selected from the group consisting of mouse myeloma cells, rat myeloma cells, mouse hybridoma cells, CHO cell, BHK cell, African green monkey kidney cells, Namalwa cell, Namalwa KJM-1 cell, human fetal kidney cells, and human leukemia cells.

9. The transformant according to claim 6, wherein the transformant is an insect cell selected from the group consisting of *Spodoptera frugiperda* ovarian cells, *Trichoplusia ni* ovarian cells, and silkworm ovarian cells.

10. A method for producing a polypeptide selected from the group consisting of (a) a polypeptide comprising the amino acid sequence SEQ ID NO: 1 or 2, and (b) a polypeptide comprising amino acid residues 56 to 359 of SEQ ID NO: 1 or 2, wherein said polypeptide has an activity to transfer fucose to an N-acetylglucosamine residue in an N-acetyllactosamine (Galβ1-4GlcNAc) structure existing in a nonreducing terminus of a sugar chain via an α1,3-linkage, but not an activity to transfer fucose to an α2,3-sialyl N-acetyllactosamine (NeuAcα2-3Galβ1-4GlcNAc) structure existing in a nonreducing terminus of a sugar chain via an α1,3-linkage, which comprises the steps of:
    culturing in a medium a transformant according to claim 6;
    producing and accumulating said polypeptide in said medium; and
    isolating said polypeptide from the medium.

11. A method for producing a polypeptide according to claim 1 or 2, which comprises the steps of:
    using a DNA encoding the polypeptide, and
    synthesizing said polypeptide by an in vitro transcription-translation system.

12. A method for producing a polypeptide selected from the group consisting of (a) a polypeptide comprising the amino acid SEQ ID NO: 1 or 2, and (b) a polypeptide comprising amino acid residues 56 to 359 of SEQ ID NO: 1 or 2, wherein said polypeptide has Lewis x sugar chain [Galβ1-4(Fucα1-3)GlcNAc]and Lewis y sugar chain [Fucα1-2Galβ1-4(Fucα1-3)GlcNAc]synthesizing activities, but not sialyl Lewis x sugar chain [NeuAcα2-3Galβ1-4(Fucα1-3)GlcNAc]synthesizing activity, which comprises the steps of:
    culturing in a medium a transformant according to claim 6;
    producing and accumulating said polypeptide in said medium; and
    isolating said polypeptide from the medium.

13. A method for producing a reaction product wherein fucose is added to an N-acetylglucosamine residue in the N-acetyllactosamine structure of an acceptor substrate via an α1,3-linkage, using a polypeptide selected from a polypeptide according to claim 1 or 2 as an enzyme source, which comprises the steps of:
    placing in an aqueous medium (a) said enzyme source, (b) an acceptor substrate selected from (i) N-acetyllactosamine(Galβ1-4GlcNAc), (ii) oligosaccharides having the N-acetyllactosamine structure in a nonreducing terminus thereof, (iii) complex carbohydrates having the N-acetyllactosamine structure in a nonreducing terminus of sugar chains, (iv) their derivatives wherein the N-acetyllactosamine structure is modified by sulfate group, and (v) their derivatives wherein the N-acetyllactosamine structure is modified by sugar, but a galactose residue in the N-acetyllactosamine structure is not modified by sialic acid via an α2,3-linkage, and (c) guanosine-5'-diphosphate fucose;

producing and accumulating the reaction product, in the aqueous medium; and collecting said reaction product from said aqueous medium.

14. The method for producing the reaction product according to claim 13, wherein a derivative is selected from sugar chains having, in a nonreducing terminus thereof, any one of the following oligosaccharide structures: Fuc α1-2Galβ1-4GlcNAc, Galα1-3Galβ1-4GlcNAc, Galα1-3 (Fucα1-2)Galβ1-4GlcNAc, GalNAcα1-3 (Fucα1-2)Galβ1-4GlcNAc, Galα1-4Galβ1-4GlcNAc, Galβ1-4GlcNAc (6SO$_3^-$); and complex carbohydrates containing said sugar chains.

15. The production method according to claim 13, wherein the complex carbohydrate is selected from the group consisting of glycoproteins, glycolipids, proteoglycans, glycopeptides, lipopolysaccharides, peptideglycans and glycosides wherein a sugar chain binds to compounds such as steroids.

16. The production method according to claim 14, wherein the complex carbohydrate is selected from the group consisting of glycoproteins, glycolipids, proteoglycans, glycopeptides, lipopolysaccharides, peptideglycans and glycosides wherein a sugar chain binds to steroids.

* * * * *

```
                          SEQUENCE LISTING

<160> NUMBER OF SEQ ID NOS: 34

<210> SEQ ID NO 1
<211> LENGTH: 359
<212> TYPE: PRT
<213> ORGANISM: Mouse

<400> SEQUENCE: 1

Met Thr Ser Thr Ser Lys Gly Ile Leu Arg Pro Phe Leu Ile Val Cys
 1               5                  10                  15

Ile Ile Leu Gly Cys Phe Met Ala Cys Leu Leu Ile Tyr Ile Lys Pro
             20                  25                  30

Thr Asn Ser Trp Val Phe Ser Pro Met Glu Ser Ala Ser Ser Val Leu
         35                  40                  45

Lys Met Lys Asn Phe Phe Ser Thr Lys Thr Asp Tyr Phe Asn Glu Thr
     50                  55                  60

Thr Ile Leu Val Trp Val Trp Pro Phe Gly Gln Thr Phe Asp Leu Thr
 65                  70                  75                  80

Ser Cys Gln Ala Met Phe Asn Ile Gln Gly Cys His Leu Thr Thr Asp
                 85                  90                  95

Arg Ser Leu Tyr Asn Lys Ser His Ala Val Leu Ile His His Arg Asp
            100                 105                 110

Ile Ser Trp Asp Leu Thr Asn Leu Pro Gln Gln Ala Arg Pro Pro Phe
        115                 120                 125

Gln Lys Trp Ile Trp Met Asn Leu Glu Ser Pro Thr His Thr Pro Gln
    130                 135                 140

Lys Ser Gly Ile Glu His Leu Phe Asn Leu Thr Leu Thr Tyr Arg Arg
145                 150                 155                 160

Asp Ser Asp Ile Gln Val Pro Tyr Gly Phe Leu Thr Val Ser Thr Asn
                165                 170                 175
```

```
Pro Phe Val Phe Glu Val Pro Ser Lys Glu Lys Leu Val Cys Trp Val
            180                 185                 190

Val Ser Asn Trp Asn Pro Glu His Ala Arg Val Lys Tyr Tyr Asn Glu
        195                 200                 205

Leu Ser Lys Ser Ile Glu Ile His Thr Tyr Gly Gln Ala Phe Gly Glu
    210                 215                 220

Tyr Val Asn Asp Lys Asn Leu Ile Pro Thr Ile Ser Thr Cys Lys Phe
225                 230                 235                 240

Tyr Leu Ser Phe Glu Asn Ser Ile His Lys Asp Tyr Ile Thr Glu Lys
                245                 250                 255

Leu Tyr Asn Ala Phe Leu Ala Gly Ser Val Pro Val Val Leu Gly Pro
            260                 265                 270

Ser Arg Glu Asn Tyr Glu Asn Tyr Ile Pro Ala Asp Ser Phe Ile His
        275                 280                 285

Val Glu Asp Phe Asn Ser Pro Ser Glu Leu Ala Lys Tyr Leu Lys Glu
    290                 295                 300

Val Asp Lys Asn Asn Lys Leu Tyr Leu Ser Tyr Phe Asn Trp Arg Lys
305                 310                 315                 320

Asp Phe Thr Val Asn Leu Pro Arg Phe Trp Glu Ser His Ala Cys Leu
                325                 330                 335

Ala Cys Asp His Val Lys Arg His Gln Glu Tyr Lys Ser Val Gly Asn
            340                 345                 350

Leu Glu Lys Trp Phe Trp Asn
        355

<210> SEQ ID NO 2
<211> LENGTH: 359
<212> TYPE: PRT
<213> ORGANISM: human

<400> SEQUENCE: 2

Met Thr Ser Thr Ser Lys Gly Ile Leu Arg Pro Phe Leu Ile Val Cys
1               5                   10                  15

Ile Ile Leu Gly Cys Phe Met Ala Cys Leu Leu Ile Tyr Ile Lys Pro
                20                  25                  30

Thr Asn Ser Trp Ile Phe Ser Pro Met Glu Ser Ala Ser Ser Val Leu
            35                  40                  45

Lys Met Lys Asn Phe Phe Ser Thr Lys Thr Asp Tyr Phe Asn Glu Thr
        50                  55                  60

Thr Ile Leu Val Trp Val Trp Pro Phe Gly Gln Thr Phe Asp Leu Thr
65                  70                  75                  80

Ser Cys Gln Ala Met Phe Asn Ile Gln Gly Cys His Leu Thr Thr Asp
                85                  90                  95

Arg Ser Leu Tyr Asn Lys Ser His Ala Val Leu Ile His His Arg Asp
            100                 105                 110

Ile Ser Trp Asp Leu Thr Asn Leu Pro Gln Gln Ala Arg Pro Pro Phe
        115                 120                 125

Gln Lys Trp Ile Trp Met Asn Leu Glu Ser Pro Thr His Thr Pro Gln
    130                 135                 140

Lys Ser Gly Ile Glu His Leu Phe Asn Leu Thr Leu Thr Tyr Arg Arg
145                 150                 155                 160

Asp Ser Asp Ile Gln Val Pro Tyr Gly Phe Leu Thr Val Ser Thr Asn
                165                 170                 175

Pro Phe Val Phe Glu Val Pro Ser Lys Glu Lys Leu Val Cys Trp Val
```

```
                180                 185                 190
Val Ser Asn Trp Asn Pro Glu His Ala Arg Val Lys Tyr Tyr Asn Glu
            195                 200                 205

Leu Ser Lys Ser Ile Glu Ile His Thr Tyr Gly Gln Ala Phe Gly Glu
        210                 215                 220

Tyr Val Asn Asp Lys Asn Leu Ile Pro Thr Ile Ser Ala Cys Lys Phe
225                 230                 235                 240

Tyr Leu Ser Phe Glu Asn Ser Ile His Lys Asp Tyr Ile Thr Glu Lys
                245                 250                 255

Leu Tyr Asn Ala Phe Leu Ala Gly Ser Val Pro Val Val Leu Gly Pro
            260                 265                 270

Ser Arg Glu Asn Tyr Glu Asn Tyr Ile Pro Ala Asp Ser Phe Ile His
        275                 280                 285

Val Glu Asp Tyr Asn Ser Pro Ser Glu Leu Ala Lys Tyr Leu Lys Glu
    290                 295                 300

Val Asp Lys Asn Asn Lys Leu Tyr Leu Ser Tyr Phe Asn Trp Arg Lys
305                 310                 315                 320

Asp Phe Thr Val Asn Leu Pro Arg Phe Trp Glu Ser His Ala Cys Leu
                325                 330                 335

Ala Cys Asp His Val Lys Arg His Gln Glu Tyr Lys Ser Val Gly Asn
            340                 345                 350

Leu Glu Lys Trp Phe Trp Asn
        355

<210> SEQ ID NO 3
<211> LENGTH: 2170
<212> TYPE: DNA
<213> ORGANISM: Mouse
<220> FEATURE:
<221> NAME/KEY: CDS
<222> LOCATION: (115)..(1191)

<400> SEQUENCE: 3
ctttccctcg ctgggatcgc tttagaatgt gataactcac gcatctgata gcaccgtgga      60
gtagttcagc actcatctct gctttccatg ctatgttctc tacactgaaa aatt atg     117
                                                                Met
                                                                1 aca tca aca tcc aaa ggc att ctt cgc cca ttt cta atc gtc tgc atc     165
Thr Ser Thr Ser Lys Gly Ile Leu Arg Pro Phe Leu Ile Val Cys Ile
            5                  10                  15 atc ctg ggc tgc ttc atg gca tgt ctg ctc att tat atc aag ccc acc     213
Ile Leu Gly Cys Phe Met Ala Cys Leu Leu Ile Tyr Ile Lys Pro Thr
        20                  25                  30 aac agc tgg gtc ttc agt cca atg gag tct gca agt tct gtg ctg aaa     261
Asn Ser Trp Val Phe Ser Pro Met Glu Ser Ala Ser Ser Val Leu Lys
    35                  40                  45 atg aaa aat ttc ttc tcc aca aaa act gat tat ttt aac gaa act acc     309
Met Lys Asn Phe Phe Ser Thr Lys Thr Asp Tyr Phe Asn Glu Thr Thr
50                  55                  60                  65 att ctg gtt tgg gta tgg cca ttt ggg cag acc ttt gac ctt aca tcc     357
Ile Leu Val Trp Val Trp Pro Phe Gly Gln Thr Phe Asp Leu Thr Ser
                70                  75                  80 tgc caa gca atg ttc aat atc caa ggg tgc cat ctc aca aca gac cgc     405
Cys Gln Ala Met Phe Asn Ile Gln Gly Cys His Leu Thr Thr Asp Arg
            85                  90                  95 tca ttg tac aac aaa tcc cat gcg gtc ctg att cac cat aga gac atc     453
Ser Leu Tyr Asn Lys Ser His Ala Val Leu Ile His His Arg Asp Ile
        100                 105                 110
```

```
agc tgg gat ctg act aac tta cct cag cag gcc agg cca ccc ttt cag    501
Ser Trp Asp Leu Thr Asn Leu Pro Gln Gln Ala Arg Pro Pro Phe Gln
    115                 120                 125 aaa tgg att tgg atg aat tta gag tca ccc act cac acc ccc caa aag    549
Lys Trp Ile Trp Met Asn Leu Glu Ser Pro Thr His Thr Pro Gln Lys
130                 135                 140                 145 agt ggc att gaa cac ttg ttc aac ctg act cta act tat cgc cgt gat    597
Ser Gly Ile Glu His Leu Phe Asn Leu Thr Leu Thr Tyr Arg Arg Asp
                150                 155                 160 tca gat atc caa gtg cct tat ggc ttc ttg acg gtg agc aca aat ccc    645
Ser Asp Ile Gln Val Pro Tyr Gly Phe Leu Thr Val Ser Thr Asn Pro
        165                 170                 175 ttt gtg ttt gaa gtg cca agc aag gag aag ttg gtg tgc tgg gtt gtg    693
Phe Val Phe Glu Val Pro Ser Lys Glu Lys Leu Val Cys Trp Val Val
            180                 185                 190 agt aac tgg aac cct gag cat gcc agg gtc aag tat tac aac gag ctc    741
Ser Asn Trp Asn Pro Glu His Ala Arg Val Lys Tyr Tyr Asn Glu Leu
195                 200                 205 agc aag agt att gaa atc cac acc tat ggc caa gca ttc gga gaa tac    789
Ser Lys Ser Ile Glu Ile His Thr Tyr Gly Gln Ala Phe Gly Glu Tyr
210                 215                 220                 225 gtg aac gat aaa aat ctg att ccc acc ata tct act tgt aaa ttt tat    837
Val Asn Asp Lys Asn Leu Ile Pro Thr Ile Ser Thr Cys Lys Phe Tyr
                230                 235                 240 ctt tca ttt gaa aac tca att cac aaa gat tac atc aca gaa aag ctc    885
Leu Ser Phe Glu Asn Ser Ile His Lys Asp Tyr Ile Thr Glu Lys Leu
            245                 250                 255 tac aat gca ttt ttg gct ggt tca gta cct gtt gtc ctg ggt cca tct    933
Tyr Asn Ala Phe Leu Ala Gly Ser Val Pro Val Val Leu Gly Pro Ser
            260                 265                 270 agg gaa aac tat gag aat tat att cca gct gat tca ttc att cat gtg    981
Arg Glu Asn Tyr Glu Asn Tyr Ile Pro Ala Asp Ser Phe Ile His Val
275                 280                 285 gaa gat ttt aac tct ccc agt gag tta gca aaa tat ctg aag gaa gtt   1029
Glu Asp Phe Asn Ser Pro Ser Glu Leu Ala Lys Tyr Leu Lys Glu Val
290                 295                 300                 305 gac aaa aac aat aag ttg tac ctt agt tac ttt aac tgg aga aag gat   1077
Asp Lys Asn Asn Lys Leu Tyr Leu Ser Tyr Phe Asn Trp Arg Lys Asp
                310                 315                 320 ttt act gta aac cta cca cgg ttt tgg gaa tca cat gca tgc ctg gca   1125
Phe Thr Val Asn Leu Pro Arg Phe Trp Glu Ser His Ala Cys Leu Ala
            325                 330                 335 tgc gac cat gta aaa agg cat caa gaa tat aag tct gtt ggt aat tta   1173
Cys Asp His Val Lys Arg His Gln Glu Tyr Lys Ser Val Gly Asn Leu
            340                 345                 350 gag aaa tgg ttt tgg aat taaagtgtcc atcattgtca cagtgaaaaa          1221
Glu Lys Trp Phe Trp Asn
355 gattaatgag acataattca gtttttcagg ataagaagaa acacgctgca tttggggcac  1281 cgtttaattt tcctgccctc ccttgaggac catgtatatt ttggtgaaat ttttaagaga  1341 tcagaattag caatcactca atttggtttt aaattatcct gtatatatgt gataacgagc  1401 actggaaata atttatttgt cactctcatt tataaacatt gtttttacat tttatagttg  1461 actgtaaagt aaatttatga tttacttgtt tctacatcaa tcagatcttt aatctatttg  1521 ggagataaaa atacatatcc taaaatatga gggactttt gccaagtatt ataaagtata  1581 gattctagct tgtataatgc taacaaagaa gaattattga atcacttaat tcttaatctc  1641
```

-continued

```
tttgacttca aagttgaaca ctactgacaa ctgatagagt ttttacttgt accacatttg    1701
tgaaggggag ctaattgatg tagcaaataa gaaagatatg aagcagaaat gttattagac    1761
ttcacattca tttttattaa gttgtttagc aaatgtagat tcccaatatt ttaagttaaa    1821
gaaaacaaga attttcagat aaacaattta tatggtttta gggagatttg attgtttgtt    1881
ttgtgggttt agtccctaat aatacctaag agaatctttt gatagttccc tttcaaatca    1941
tgaagataac cactatttta aaaataaata atttcctctt ataacaataa aaaaatgata    2001
tcttcaaata caaataaatg tataaattat accatttata gaacgctagt tacttcattc    2061
atttgaaata ttttttccaa agcatccata tttaagtttt attttactgt atttgttaat    2121
aaatagaagt aaaacttgaa aaaaaaaaa aaaaaaaaa aaaaaaaa                   2170
```

```
<210> SEQ ID NO 4
<211> LENGTH: 2822
<212> TYPE: DNA
<213> ORGANISM: human
<220> FEATURE:
<221> NAME/KEY: CDS
<222> LOCATION: (1289)..(2365)

<400> SEQUENCE: 4
```

```
aagctttgct actcagagag tctcatatgc tttaagaaaa actacatagc aaaagaaggt     60
gcttttttta atgttcacat atatttaggt aattaaatga aggataattt ctcccgtttt    120
ttggaaggaa acatctaatg tttctatgct agtttctgtc aaaatttcaa atactttaa    180 tgagtctgaa atttataggc catattattt tcgtaagaga agcaacatga atttcaaatg    240
acccgtgaga atttatcaa taaacagttt ttgcaaatat attttgtgt tcatagccat     300 aaagaggcat gaatgccgaa gagaaaaaaa cttgaaaaca cttttttctt taaaaaaaa    360 gccttcactc atctttttag ccacaatctg ctaaaattca tgacatcaaa gttgttcttc    420
atgaaatata gcccttttt gagaatttgt ttattttta ataccgata tcatcttaat      480 acaaagaaaa acttttttaa agcccttagg ctatgtaagt gagaacgttt ttccaatgca    540
aatagaacat ttgattatta catcttggta gatatcggat gtactaacaa attattaaaa    600
gtaaacaaag aaaactgtaa gaaaatata taaataaaa caaaacactg tgagttttga     660
atttataaaa tttgcctgag tgtacttgtt ttttaaaat gtatcaaatc aagagttgcc    720 attttttac cagatgatta tactaatgca tttgcaaact gtgaaggtaa atttataacg    780 agaaaacaa aaacataacg ttttttaaaaa cagtttagtt ttctaacgaa ttccatctga    840
accacaaagt tatggtacag tctcaatatg cgagtaaata agtgattata tcaactggga    900
gatgttcaca aatctgatgt ggttacaaaa tactaaaaat tttagtcatg gctttagcga    960
tgacagtcta ggttgtgcca cttttctaca agcaaataaa agtagaactg ttaaggatag   1020
cattgaaaaa aacgttactt ggtttgaaga tatgctggta cttttagaag agttttttggg   1080 aaacttcctt ttgaaagctg tttcttggct ttgaggaaag ttctgtttct ctcaatggtt    1140
tgataacact gaaaaggaaa atgctgttga ttactacttg tttatctcat atttatgatt    1200
ttaaatatat ctccaatata tttatgattt tctcttcatt cccaccgcta cctccccttc    1260
tgtctttctc tatttcgtag gaaaaatt atg aca tca aca tcc aaa gga att    1312
                              Met Thr Ser Thr Ser Lys Gly Ile
                                   1                5 ctt cgc cca ttt tta att gtc tgc att atc ctg ggc tgt ttc atg gca    1360
Leu Arg Pro Phe Leu Ile Val Cys Ile Ile Leu Gly Cys Phe Met Ala
     10              15                  20
```

-continued

```
tgt ctt ctc att tac atc aaa cct acc aac agc tgg atc ttc agt cca     1408
Cys Leu Leu Ile Tyr Ile Lys Pro Thr Asn Ser Trp Ile Phe Ser Pro
 25              30                  35                  40 atg gaa tca gcc agc tct gtg ctg aaa atg aaa aac ttc ttt tcc acc     1456
Met Glu Ser Ala Ser Ser Val Leu Lys Met Lys Asn Phe Phe Ser Thr
                 45                  50                  55 aaa act gat tat ttt aat gaa act act att ctg gtg tgg gtg tgg cca     1504
Lys Thr Asp Tyr Phe Asn Glu Thr Thr Ile Leu Val Trp Val Trp Pro
                     60                  65                  70 ttt ggg cag acc ttt gac ctt aca tcc tgc caa gca atg ttc aac atc     1552
Phe Gly Gln Thr Phe Asp Leu Thr Ser Cys Gln Ala Met Phe Asn Ile
         75                  80                  85 caa gga tgc cat ctc aca acg gac cgt tca ctg tac aac aaa tcc cat     1600
Gln Gly Cys His Leu Thr Thr Asp Arg Ser Leu Tyr Asn Lys Ser His
     90                  95                 100 gca gtt ctg atc cat cac cga gac atc agt tgg gat ctg aca aat tta     1648
Ala Val Leu Ile His His Arg Asp Ile Ser Trp Asp Leu Thr Asn Leu
105                 110                 115                 120 cct cag caa gct agg cca ccc ttc cag aaa tgg att tgg atg aat ttg     1696
Pro Gln Gln Ala Arg Pro Pro Phe Gln Lys Trp Ile Trp Met Asn Leu
                125                 130                 135 gaa tca cca act cac act ccc caa aag agt ggc att gag cac ttg ttt     1744
Glu Ser Pro Thr His Thr Pro Gln Lys Ser Gly Ile Glu His Leu Phe
                140                 145                 150 aac ctg act ctg act tac cgc cgt gat tca gat atc caa gtg cct tat     1792
Asn Leu Thr Leu Thr Tyr Arg Arg Asp Ser Asp Ile Gln Val Pro Tyr
            155                 160                 165 ggc ttc ttg acg gta agc aca aat ccc ttc gtg ttt gaa gtg cca agc     1840
Gly Phe Leu Thr Val Ser Thr Asn Pro Phe Val Phe Glu Val Pro Ser
170                 175                 180 aaa gag aaa ttg gtg tgc tgg gtt gtg agt aac tgg aac cct gag cat     1888
Lys Glu Lys Leu Val Cys Trp Val Val Ser Asn Trp Asn Pro Glu His
185                 190                 195                 200 gcc aga gtc aag tat tac aat gag cta agc aaa agc att gaa atc cat     1936
Ala Arg Val Lys Tyr Tyr Asn Glu Leu Ser Lys Ser Ile Glu Ile His
                205                 210                 215 acc tac ggg caa gca ttt gga gaa tat gtc aat gat aaa aat ttg att     1984
Thr Tyr Gly Gln Ala Phe Gly Glu Tyr Val Asn Asp Lys Asn Leu Ile
                220                 225                 230 cct acc ata tct gct tgt aaa ttt tat ctt tcc ttt gaa aat tca atc     2032
Pro Thr Ile Ser Ala Cys Lys Phe Tyr Leu Ser Phe Glu Asn Ser Ile
            235                 240                 245 cac aag gat tac atc acg gaa aag cta tac aat gct ttt ctg gct ggc     2080
His Lys Asp Tyr Ile Thr Glu Lys Leu Tyr Asn Ala Phe Leu Ala Gly
250                 255                 260 tct gta cct gtt gtt ctg gga cca tct agg gaa aac tat gag aat tat     2128
Ser Val Pro Val Val Leu Gly Pro Ser Arg Glu Asn Tyr Glu Asn Tyr
265                 270                 275                 280 att cca gca gat tca ttc att cat gtg gaa gat tat aac tct ccc agt     2176
Ile Pro Ala Asp Ser Phe Ile His Val Glu Asp Tyr Asn Ser Pro Ser
                285                 290                 295 gag cta gca aag tat ctg aag gaa gtc gac aaa aac aat aag tta tac     2224
Glu Leu Ala Lys Tyr Leu Lys Glu Val Asp Lys Asn Asn Lys Leu Tyr
                300                 305                 310 ctt agt tac ttt aac tgg agg aag gat ttc act gta aat ctt cca cga     2272
Leu Ser Tyr Phe Asn Trp Arg Lys Asp Phe Thr Val Asn Leu Pro Arg
            315                 320                 325 ttt tgg gaa tca cat gca tgt ttg gct tgc gat cat gtg aaa agg cat     2320
Phe Trp Glu Ser His Ala Cys Leu Ala Cys Asp His Val Lys Arg His
330                 335                 340
```

-continued

```
caa gaa tat aag tct gtt ggt aat tta gag aaa tgg ttt tgg aat       2365
Gln Glu Tyr Lys Ser Val Gly Asn Leu Glu Lys Trp Phe Trp Asn
345                 350                 355 taaaatttt catcacttgc acacttgata aatattttga tgagatatca tccaagtatt   2425
gaggataaga agagatgcaa catactactt ttgtgtcaca atttatttt atcaccctct   2485 ctagggtaac gtgtatattt tggtggagat ttttaaaagc tcagcatgag caatcattcc  2545
attcggtttt aaattatcct gtatatacct aattatgtgc actggagagt aatttattct  2605
tcattatcat ttgtaaacat tgcttttca cattttgta gttgtccata atgtaagctt    2665
gtggtttgat tattgtttcc acactgatca gctgtttaat ctatttggga aatgaagatg  2725
cacatcttaa agtatgaaaa attttcacta agtattacaa tgtctagttc caactttgca  2785
tactataaca gaggaagaac atgttgcgat tgaattc                          2822

<210> SEQ ID NO 5
<211> LENGTH: 2676
<212> TYPE: DNA
<213> ORGANISM: human
<220> FEATURE:
<221> NAME/KEY: CDS
<222> LOCATION: (295)..(1371)

<400> SEQUENCE: 5
gcgcgcgcgg cgcagcagct ccagattcac tgctctcccc tgcagctccc cgcgccccg    60 ccgctgtcgc tgcctcggtg tcccccagcc ccagtcgcgc tcttaggaca gcgccgccac  120
cgccgcctgg ccctgcctgc tcctgcgcc gcgcagccct cgcgagcgcc ccggatggcg   180 ctttaccccct aggaccgatt tagaatgtaa taactcaagg atttgataat acagtgaagt  240
agtataacaa ctgtctacgt gcttccatg atatgttctc tatattgaaa aatt atg     297
                                                               Met
                                                                 1 aca tca aca tcc aaa gga att ctt cgc cca ttt tta att gtc tgc att    345
Thr Ser Thr Ser Lys Gly Ile Leu Arg Pro Phe Leu Ile Val Cys Ile
            5                   10                  15 atc ctg ggc tgt ttc atg gca tgt ctt ctc att tac atc aaa cct acc    393
Ile Leu Gly Cys Phe Met Ala Cys Leu Leu Ile Tyr Ile Lys Pro Thr
        20                  25                  30 aac agc tgg atc ttc agt cca atg gaa tca gcc agc tct gtg ctg aaa    441
Asn Ser Trp Ile Phe Ser Pro Met Glu Ser Ala Ser Ser Val Leu Lys
    35                  40                  45 atg aaa aac ttc ttt tcc acc aaa act gat tat ttt aat gaa act act    489
Met Lys Asn Phe Phe Ser Thr Lys Thr Asp Tyr Phe Asn Glu Thr Thr
50                  55                  60                  65 att ctg gtg tgg gtg tgg cca ttt ggg cag acc ttt gac ctt aca tcc    537
Ile Leu Val Trp Val Trp Pro Phe Gly Gln Thr Phe Asp Leu Thr Ser
                70                  75                  80 tgc caa gca atg ttc aac atc caa gga tgc cat ctc aca acg gac cgt    585
Cys Gln Ala Met Phe Asn Ile Gln Gly Cys His Leu Thr Thr Asp Arg
            85                  90                  95 tca ctg tac aac aaa tcc cat gca gtt ctg atc cat cac cga gac atc    633
Ser Leu Tyr Asn Lys Ser His Ala Val Leu Ile His His Arg Asp Ile
        100                 105                 110 agt tgg gat ctg aca aat tta cct cag caa gct agg cca ccc ttc cag    681
Ser Trp Asp Leu Thr Asn Leu Pro Gln Gln Ala Arg Pro Pro Phe Gln
    115                 120                 125 aaa tgg att tgg atg aat ttg gaa tca cca act cac act ccc caa aag    729
Lys Trp Ile Trp Met Asn Leu Glu Ser Pro Thr His Thr Pro Gln Lys
130                 135                 140                 145
```

```
agt ggc att gag cac ttg ttt aac ctg act ctg act tac cgc cgt gat      777
Ser Gly Ile Glu His Leu Phe Asn Leu Thr Leu Thr Tyr Arg Arg Asp
            150                 155                 160 tca gat atc caa gtg cct tat ggc ttc ttg acg gta agc aca aat ccc      825
Ser Asp Ile Gln Val Pro Tyr Gly Phe Leu Thr Val Ser Thr Asn Pro
        165                 170                 175 ttc gtg ttt gaa gtg cca agc aaa gag aaa ttg gtg tgc tgg gtt gtg      873
Phe Val Phe Glu Val Pro Ser Lys Glu Lys Leu Val Cys Trp Val Val
    180                 185                 190 agt aac tgg aac cct gag cat gcc aga gtc aag tat tac aat gag cta      921
Ser Asn Trp Asn Pro Glu His Ala Arg Val Lys Tyr Tyr Asn Glu Leu
195                 200                 205 agc aaa agc att gaa atc cat acc tac ggg caa gca ttt gga gaa tat      969
Ser Lys Ser Ile Glu Ile His Thr Tyr Gly Gln Ala Phe Gly Glu Tyr
210                 215                 220                 225 gtc aat gat aaa aat ttg att cct acc ata tct gct tgt aaa ttt tat     1017
Val Asn Asp Lys Asn Leu Ile Pro Thr Ile Ser Ala Cys Lys Phe Tyr
            230                 235                 240 ctt tcc ttt gaa aat tca atc cac aag gat tac atc acg gaa aag cta     1065
Leu Ser Phe Glu Asn Ser Ile His Lys Asp Tyr Ile Thr Glu Lys Leu
        245                 250                 255 tac aat gct ttt ctg gct ggc tct gta cct gtt gtt ctg gga cca tct     1113
Tyr Asn Ala Phe Leu Ala Gly Ser Val Pro Val Val Leu Gly Pro Ser
    260                 265                 270 agg gaa aac tat gag aat tat att cca gca gat tca ttc att cat gtg     1161
Arg Glu Asn Tyr Glu Asn Tyr Ile Pro Ala Asp Ser Phe Ile His Val
275                 280                 285 gaa gat tat aac tct ccc agt gag cta gca aag tat ctg aag gaa gtc     1209
Glu Asp Tyr Asn Ser Pro Ser Glu Leu Ala Lys Tyr Leu Lys Glu Val
290                 295                 300                 305 gac aaa aac aat aag tta tac ctt agt tac ttt aac tgg agg aag gat     1257
Asp Lys Asn Asn Lys Leu Tyr Leu Ser Tyr Phe Asn Trp Arg Lys Asp
            310                 315                 320 ttc act gta aat ctt cca cga ttt tgg gaa tca cat gca tgt ttg gct     1305
Phe Thr Val Asn Leu Pro Arg Phe Trp Glu Ser His Ala Cys Leu Ala
        325                 330                 335 tgc gat cat gtg aaa agg cat caa gaa tat aag tct gtt ggt aat tta     1353
Cys Asp His Val Lys Arg His Gln Glu Tyr Lys Ser Val Gly Asn Leu
    340                 345                 350 gag aaa tgg ttt tgg aat taaaattttt catcacttgc acacttgata            1401
Glu Lys Trp Phe Trp Asn
355 aatattttga tgagatatca tccaagtatt gaggataaga agagatgcaa catactactt   1461 ttgtgtcaca atttattttt atcaccctct ctagggtaac gtgtatattt tggtggagat   1521 ttttaaaagc tcagcatgag caatcattcc attcggtttt aaattatcct gtatatacct   1581 aattatgtgc actggagagt aatttattct tcattatcat ttgtaaacat tgctttttca   1641 cattttgta gttgtccata atgtaagctt gtggtttgat tattgtttcc acactgatca    1701 gctgtttaat ctatttggga aatgaagatg cacatcttaa agtatgaaaa attttcacta   1761 agtattacaa tgtctagttc caactttgca tactataaca gaggaagaac atgttgcgat   1821 tgaattctaa cctctttgac tcctaagatg aatgaagtgt ataactgtct ctatttgatc   1881 tatttttttt acctgtttat cacatttgtg aaggtgaaat tattcatgga gtgaataaga   1941 aagatatgaa gcagaactgt tctattcagg aagctattag acttctcatt tatttttcatt  2001 aagctgattt gcagctactt attctcatgg tcttaaatta aattattcaa gtattttaa   2061
```

-continued

| | |
|---|---|
| atatccaatt tgttgtgatt ttcagcacct gggaagtaat cccaataata ctttagaaaa | 2121 |
| tctaagacag ttctttctgc tactgatgac actcattgtc ataataaaac aaataatttc | 2181 |
| ctcaaataac aaagaaaaat gatacctata aatatattta taaatggtgt catttatgaa | 2241 |
| caatgtttaa ttatgtatca atttaagatt tttttctgaa gccctaatat ttaaaatggc | 2301 |
| cttattttac catatggata taagatttgg ctcataatga tgagccctat catttgattt | 2361 |
| gagttctatc atttaagaga gcctaaataa aattatcatc aagtattaa atataagacg | 2421 |
| ttaaatataa taaagtgggg atatatagaa aacacacagt gttagcacag agtaagatct | 2481 |
| caatgcacat ttgttggatg aataaataaa tgcaattgaa ttcccagaaa aatgattgtt | 2541 |
| tcaaggaagt gacagttcta ctttagaagt actaattgga gatgactttt atatcccatt | 2601 |
| ttggtaatta ttcatacata gcacatatga ccatgatgtt cagggcttta tagaaccaaa | 2661 |
| taaacctacc attac | 2676 |

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 6
ctttagagca c                                                          11

<210> SEQ ID NO 7
<211> LENGTH: 8
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 7 ctctaaag                                                              8

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 8
ctggattcta tccagtgcaa ggcgagggtt tg                                   32

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 9
ctgaattctc atcgctggaa ccagtctgcc aag                                  33

<210> SEQ ID NO 10
<211> LENGTH: 31
<212> TYPE: DNA
<213> ORGANISM: Artificial Sequence

```
<220> FEATURE:
<223> OTHER INFORMATION: Description of Artificial Sequence: synthetic
      DNA

<400> SEQUENCE: 10
ctgaattcac agcttctttg cagctccttc g                                    31

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 11
ctaagcttgt gtaaaacgca gctcagtaac ag                                   32

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 12
cagctgggat ctgactaact tacc                                            24

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 13
ccacatgaat gaatgaatca gctgg                                           25

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 14
gatatcgctg cgctggtcgt cgac                                            24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 15
caagaaggaa ggctggaaaa gagc                                            24

<210> SEQ ID NO 16
<211> LENGTH: 24
<212> TYPE: DNA
<213> ORGANISM: Artificial Sequence
<220> FEATURE:
```

```
<223> OTHER INFORMATION: Description of Artificial Sequence: synthetic
      DNA

<400> SEQUENCE: 16
gcttcttgac ggtgagcaca aatc                                          24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 17
tgcttggcca taggtgtgga tttc                                          24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 18
gcttcttgac ggtgagcaca aatc                                          24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 19
tgcttggcca taggtgtgga tttc                                          24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 20
gattcccacc atatctactt gtaa                                          24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 21
tgaatcagct ggaatataat tctc                                          24

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: synthetic
```

-continued

DNA

<400> SEQUENCE: 22
aggccaccct ttcagaaatg                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 23
agttttccct agatggaccc                                                    20

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 24
ctgaattctg gctgggatcg ctttagaatg tg                                      32

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 25
ctgaattcaa atgaatgaag taactagcgt tc                                      32

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 26
aaattatgac atcaacatcc aaagg                                              25

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 27
ccaacagact tatattcttg atgcc                                              25

<210> SEQ ID NO 28
<211> LENGTH: 891
<212> TYPE: DNA
<213> ORGANISM: Mouse

<400> SEQUENCE: 28

-continued

| | |
|---|---|
| ctttagctgg tcaaccccag tgaagaacaa acacagccag cagatacaag ggactggaga | 60 |
| aggttgcctg cattgagctc cctgctgtcg ccttctggct ggacagtccg tgccaaatag | 120 |
| cgcctggggg ggtggggggtg ggggacagca ataaggaact gacagaagcg gttgctgcaa | 180 |
| gtccacagtt tgacctaaaa ggagagtgga ggagggtggc agactaagag tctgcatatc | 240 |
| ggagacgcag caatggaacc agtggctatg tgtgcgcgca caggtgccac aggcctggag | 300 |
| agcaatgctg tgtctctgca gcctcccgac tcaacacacg cggtggcttg ctgaaactgc | 360 |
| atccgcagcc gagcgtgggt actcccaggc acagtcaccg gaggaagagc caaaggaaag | 420 |
| ggcgcgaagg gggttagcat ggagcggcag ggtattgggg caagacccac aggctcattt | 480 |
| tggagctcct ctggtgggaa cctgtacccg gctgctatgc tcctcccttc tcttcccaac | 540 |
| tctcggtgat catctccatc tccctcgcg catcccttcc ccctccctg ctttctttgc | 600 |
| tctccctccc tgccgcgtgc ctgctccct ccccctctcc ctggctgctc tgggcagcag | 660 |
| caacctcggc agcccgggag atgggaagag agcgcgcggg gcgctgcagc tctggagccc | 720 |
| tggatctttc ctcacccggt gccttgagac cccgccgccg ctctcgcctc ttggctaccc | 780 |
| ccggactccg gctacgctac taggacacg ccgccaccac cgccagccct cgtcccgccc | 840 |
| gcgccgcgct gccctcccgc gccctggatg gagctttcct cgctgggatc g | 891 |

<210> SEQ ID NO 29
<211> LENGTH: 87
<212> TYPE: DNA
<213> ORGANISM: Mouse

<400> SEQUENCE: 29

| | |
|---|---|
| ctttagaatg tgataactca cgcatctgat agcaccgtgg agtagttcag cactcatctc | 60 |
| tgctttccat gctatgttct ctacact | 87 |

<210> SEQ ID NO 30
<211> LENGTH: 2036
<212> TYPE: DNA
<213> ORGANISM: Mouse

<400> SEQUENCE: 30

| | |
|---|---|
| gaaaaattat gacatcaaca tccaaaggca ttcttcgccc atttctaatc gtctgcatca | 60 |
| tcctgggctg cttcatggca tgtctgctca tttatatcaa gcccaccaac agctgggtct | 120 |
| tcagtccaat ggagtctgca agttctgtgc tgaaaatgaa aaatttcttc tccacaaaaa | 180 |
| ctgattattt taacgaaact accattctgg tttgggtatg gccatttggg cagacctttg | 240 |
| accttacatc ctgccaagca atgttcaata tccaagggtg ccatctcaca acagaccgct | 300 |
| cattgtacaa caaatcccat gcggtcctga ttcaccatag agacatcagc tgggatctga | 360 |
| ctaacttacc tcagcaggcc aggccaccct ttcagaaatg gatttggatg aatttagagt | 420 |
| cacccactca caccccccaa aagagtggca ttgaacactt gttcaacctg actctaactt | 480 |
| atcgccgtga ttcagatatc caagtgcctt atggcttctt gacggtgagc acaaatccct | 540 |
| ttgtgtttga agtgccaagc aaggagaagt tggtgtgctg ggttgtgagt aactggaacc | 600 |
| ctgagcatgc cagggtcaag tattacaacg agctcagcaa gagtattgaa atccacacct | 660 |
| atggccaaga attcggagaa tacgtgaacg ataaaaatct gattcccacc atatctactt | 720 |
| gtaaattta tctttcattt gaaaactcaa ttcacaaaga ttacatcaca gaaaagctct | 780 |
| acaatgcatt tttggctggt tcagtacctg ttgtcctggg tccatctagg gaaaactatg | 840 |
| agaattatat tccagctgat tcattcattc atgtggaaga ttttaactct cccagtgagt | 900 |

-continued

```
tagcaaaata tctgaaggaa gttgacaaaa acaataagtt gtaccttagt tactttaact    960
ggagaaagga ttttactgta aacctaccac ggttttggga atcacatgca tgcctggcat   1020
gcgaccatgt aaaaaggcat caagaatata agtctgttgg taatttagag aaatggtttt   1080
ggaattaaag tgtccatcat tgtcacagtg aaaaagatta atgagacata attcaagttt   1140
tcaggataag aagaaacacg ctgcatttgg ggcaccgttt aattttcctg ccctcccttg   1200
aggaccatgt atattttggt gaaattttta agagatcaga attagcaatc actcaatttg   1260
gttttaaatt atcctgtata tatgtgataa cgagcactgg aaataattta tttgtcactc   1320
tcatttataa acattgtttt tacattttat agttgactgt aaagtaaatt tatgatttac   1380
ttgtttctac atcaatcaga tctttaatct atttgggaga taaaaataca tatcctaaaa   1440
tatgagggac ttttttgccaa gtattataaa gtatagattc tagcttgtat aatgctaaca   1500
aagaagaatt attgaatcac ttaattctta atctctttga cttcaaagtt gaacactact   1560
gacaactgat agagttttta cttgtaccac atttgtgaag gggagctaat tgatgtagca   1620
aataagaaag atatgaagca gaaatgttat tagacttcac attcattttt attaagttgt   1680
ttagcaaatg tagattccca atattttaag ttaaagaaaa caagaatttt cagataaaca   1740
atttatatgg ttttagggag atttgattgt tgtttttgtg ggtttagtcc ctaataatac   1800
ctaagagaat cttttgatag ttcccttttca aatcatgaag ataaccacta ttttaaaaat   1860
aaataatttc ctcttataac aataaaaaaa tgatatcttc aaatacaaat aaatgtataa   1920
attataccat ttatagaacg ctagttactt cattcatttg aaatatttttt tccaaagcat   1980 ccatatttaa gttttatttt actgtatttg ttaataaata gaagtaaaac ttgaaa       2036
```

<210> SEQ ID NO 31
<211> LENGTH: 2056
<212> TYPE: DNA
<213> ORGANISM: Mouse

<400> SEQUENCE: 31

```
ggtaccaaac atcaaatttt ttgcatgacc ccttcagtcc tgggccatca actgcaattg     60
aggctgtacc ttcactaatg gctgttgctg gccttttaca gtgtcaggcc ttagctgctc    120
tccatgacca ctttgtgtct tcaaatccag taccatctca aactagaggc aagaggcaga    180
gagcacacta tagatggtag aagatttttt taaaacctca tgcccaccct tactaacatg    240
cctcatctaa caaggtcata ttccttaatt ctccccctaat agttgcaacc actggcaccc    300
aacaaaattt attagcctaa ggaggttcct ctcacttaaa ctactacact tataaaaaca    360
caatcaaagg atatgaaatt gaggtgggga taggttttaga ttatgaaagg atttaggagg    420
tagggggtaa tatacatata tgtataaagc ccaaragtct caactatatg arrattatat    480
aatcactaca ttaaagtcgg ggatayccta atcatatatg aggaaatttg ttttttgttg    540
ttattttatt tatttacatt taaaatgtaa atctgcccat gtgattccct ctcccctttg    600
tctggaagtt tgtactttat taattctcag taaccacaat taattaaaca gttactgcca    660
tttgcaaact tcatgattca tctctgagta agagtgctga gtgggatatt atgcttcatc    720
aatcattacc tttccatgtt ctttaaatga ttaataatcg gtgggtctac ctggtgtact    780
gctgtgtgta catgctggac acagcaacat gtgctctaga agctgaggcg tctggcccat    840
tggcccttac tgaatagatg gtcctcttat tctgatcatc aaaagacat gaaaccaaat    900 gttttcattg gcatgcatgc tgaacatgaa agagtctaac aagttagaga cactgtcaaa    960
```

```
tagtaactta tcactaaaat ttaactttta tttttcttca agtaaaacaa tacaggaaga    1020
gatagaagtt tttcaataat atgtaaggct gacttgttgc agtaaaaatg tttttcacac    1080
tgcattcata actgagacag catttatttt aatatgagta catttgttat ataaggcata    1140
attatgtaaa gtaaaatgtc taaattattt tagagactaa gaccctttag cacatgaaga    1200
tttctacatt cagaaaagca gtgtgagccc atggacacat gcttggtgca catacacaca    1260
cacacacaca cacacacccc agaacttcct ttctccagtg ctctgctaag aagtacaggg    1320
atacttactg tatcatttga agagagttta actagactac tttttctacc tgtatcatta    1380
cacacatcat ccacttgctt cctgtctgct gcctatttcc aatcagaatg cgaagattat    1440
gaaacaaaat gcaaggttca cagaaataca gtacagcgat actctgattg tcgttatatt    1500
tactaaatgt gtgaatttat tccttgattc ttgagtgtaa gaggagcccc taaatatact    1560
ttctatatgt atttgaatcg tagtctaaaa gtaatttcg aggattgact tgtagtccaa    1620
caaaataaac aaaaactttg caagtggag ctctatctat ctatctatct atctatccat    1680
ccatctatcc tttctttctc tctcttcctt cttccttcct tcctt ccttc cttccttcct    1740 tccttccttc cttccttcct cccttctttt ctccctacca ttctttctgt cgttctatct    1800
attacacaca tgtagtctat ctatacatct catcatctct actgtgtgtc atctacccca    1860
tgtagaatat atattttatg tggcgcttca gagaaagaga gctaaaatct gtagacgcaa    1920
acaacatgtg cccc ttctac cacatttatc acaaaccctt ccccaaaaaa ctacatcgta    1980
gagaatttgg gtccacagac aactctgccc ctcctatttt agtttaattt taatcacccc    2040 ccacc ttgac cccgga                                                  2056

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 32
aagcctaatg cttgctctca gtcg                                            24

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 33
acattgggtg gaaacattcc ag                                              22

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 34
tttgctacat caattagctc ccct                                            24
```